United States Patent
Nishio et al.

(10) Patent No.: US 10,519,106 B2
(45) Date of Patent: Dec. 31, 2019

(54) UREA DERIVATIVE AND USE THEREFOR

(71) Applicant: Toray Industries, Inc., Tokyo (JP)

(72) Inventors: Yukihiro Nishio, Kamakura (JP); Masashi Yamamoto, Kamakura (JP); Yuko Kubota, Kamakura (JP); Hideyuki Tsutsui, Otsu (JP); Tomohide Masuda, Kamakura (JP); Keiichi Okimura, Kamakura (JP); Syuji Udagawa, Kamakura (JP); Mie Kaino, Kamakura (JP); Hiroyuki Meguro, Kamakura (JP); Yumiko Sekiya, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/753,594

(22) PCT Filed: Aug. 31, 2016

(86) PCT No.: PCT/JP2016/075497
§ 371 (c)(1),
(2) Date: Feb. 20, 2018

(87) PCT Pub. No.: WO2017/038871
PCT Pub. Date: Mar. 9, 2017

(65) Prior Publication Data
US 2019/0010117 A1    Jan. 10, 2019

(30) Foreign Application Priority Data

Aug. 31, 2015   (JP) .................. 2015-170014

(51) Int. Cl.
*C07C 275/34* (2006.01)
*C07C 275/30* (2006.01)
*A61P 35/02* (2006.01)

(52) U.S. Cl.
CPC .......... *C07C 275/34* (2013.01); *C07C 275/30* (2013.01); *A61P 35/02* (2018.01)

(58) Field of Classification Search
None
See application file for complete search history.

(56) References Cited

U.S. PATENT DOCUMENTS

| | | | |
|---|---|---|---|
| 5,922,767 | A | 7/1999 | Kanamaru et al. |
| 2012/0184735 | A1 | 7/2012 | Kaneko et al. |
| 2015/0141400 | A1 | 5/2015 | Murata et al. |
| 2015/0152047 | A1 | 6/2015 | Murata et al. |

FOREIGN PATENT DOCUMENTS

| | | |
|---|---|---|
| CN | 101367769 A | 2/2009 |
| JP | 10-182588 A | 7/1998 |
| JP | 10-306078 A | 11/1998 |
| WO | 2011/040509 A1 | 4/2011 |
| WO | 2012/000304 A1 | 1/2012 |
| WO | 2012/094451 A1 | 7/2012 |
| WO | 2013/020014 A1 | 2/2013 |
| WO | 2013/161851 A1 | 10/2013 |
| WO | 2013/161853 A1 | 10/2013 |
| WO | 2014/032755 A2 | 3/2014 |

OTHER PUBLICATIONS

Ford, C. E. et al., "Expression and mutation analysis of the discoidin domain receptors 1 and 2 in non-small cell lung carcinoma", *British Journal of Cancer*, 2007, vol. 96, pp. 808-814.
Vogel, W. F. et al., "Sensing extracellular matrix: An update on discoidin domain receptor function", *Cellular Signalling*, 2006, vol. 18, Issue 8, pp. 1108-1116 (Abstract only).
Vogel, W., "Discoidin domain receptors: structural relations and functional implications", *The FASEB Journal*, 1999, vol. 13, No. 9001, pp. S77-S82.
Valiathan, R. R. et al., "Discoidin domain receptor tyrosine kinases: new players in cancer progression", *Cancer and Metastasis Reviews*, 2012, vol. 31, Issue 1-2, pp. 295-321 (Abstract only).
Vogel, W. et al., "The Discoidin Domain Receptor Tyrosine Kinases Are Activated by Collagen", *Molecular Cell*, 1997, vol. 1, pp. 13-23.
Valencia, K. et al., "Inhibition of Collagen Receptor Discoidin Domain Receptor-1 (DDR1) Reduces Cell Survival, Homing, and Colonization in Lung Cancer Bone Metastasis", *Clinical Cancer Research*, 2012, vol. 18, No. 4, pp. 969-980.
Barker, K. T. et al., "Expression patterns of the novel receptor-like tyrosine kinase, DDR, in human breast tumours", *Oncogene*, 1995, vol. 10, No. 3, pp. 569-575 (Abstract only).
Yamanaka, R. et al., "Identification of expressed genes characterizing long-term survival in malignant glioma patients", *Oncogene*, 2006, vol. 25, pp. 5994-6002.
Miao, L. et al., "Discoidin domain receptor 1 is associated with poor prognosis of non-small cell lung cancer and promotes cell invasion via epithelial-to-mesenchymal transition", *Medical Oncology*, 2013, vol. 30, Article 626 (Abstract only).
Kim, H.-G. et al., "DDR1 Receptor Tyrosine Kinase Promotes Prosurvival Pathway through Notch1 Activation", *The Journal of Biological Chemistry*, 2011, vol. 286, No. 20, pp. 17672-17681.

(Continued)

*Primary Examiner* — Sudhakar Katakam
*Assistant Examiner* — Jennifer C Sawyer
(74) *Attorney, Agent, or Firm* — DLA Piper LLP

(57) ABSTRACT

A compound has inhibitory activity on Discoidin Domain Receptor 1. The compound includes a urea derivative represented by the formula below or a pharmaceutically acceptable salt thereof.

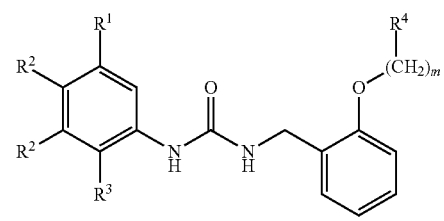

8 Claims, No Drawings

(56) References Cited

OTHER PUBLICATIONS

Gao, M. et al., "Discovery and Optimization of 3-(2-(Pyrazolo[1,5-α]pyrimidin-6-yl)ethynyl) benzamides as Novel Selective and Orally Bioavailable Discoidin Domain Receptor 1 (DDR1) Inhibitors", *J. Med. Chem.*, 2013, vol. 56, No. 8, pp. 3281-3295 (Abstract only).
Kim, H.-G. et al., "Discovery of a Potent and Selective DDR1 Receptor Tyrosine Kinase Inhibitor", *ACS Chemical Biology*, 2013, vol. 8, pp. 2145-2150.
Yupeng Li et al., "Small Molecule Discoidin Domain Receptor Kinase Inhibitors and Potential Medical Applications", *J. Med Chem.*, Jan. 8, 2015, vol. 58, No. 8, pp. 3287-3301.
Extended European Search Report dated Mar. 8, 2019, of counterpart European Application No. 16841901.8.

UREA DERIVATIVE AND USE THEREFOR

TECHNICAL FIELD

This disclosure relates to a urea derivative and use thereof.

BACKGROUND

Discoidin Domain Receptor 1 (hereinafter referred to as DDR1) is a receptor-type tyrosine kinase activated by its ligand, collagen, and carries a discoidin domain capable of binding to collagen in its extracellular region, and a receptor-type tyrosine kinase domain in its intracellular region, respectively (Vogel et al., British Journal of Cancer. (2007) 96: 808-814 and Vogel et al., Cellular Signalling. (2006) 18: 1108-1116).

It has been reported that activation of DDR1 causes promotion of cell infiltration, cell migration, and cell survival (Vogel et al., FASEB Journal. (1999) 13: S77-S82, Valiathan et al., Cancer Metastasis Review. (2012) 31: 295-321 and Vogel et al., Molecular Cell. (1997) 1: 13-23). In the clinical setting, it has been reported that the expression of DDR1 is increased in non-small cell lung cancer, glioma, and breast cancer, and that the increased expression of DDR1 is correlated with poor prognosis and with cell infiltration in non-small cell lung cancer (Valencia et al., Clinical Cancer Research. (2012) 18; 969-980, Barker et al., Oncogene. (1995) 10: 569-575, Yamanaka et al., Oncogene. (2006) 25: 5994-6002 and Miao et al., Medical Oncology. (2013) 30: 626).

It has been reported that knocking-down of DDR1 by RNA interference results in suppressing bone metastasis of lung cancer cells (Valencia et al., Clinical Cancer Research. (2012) 18; 969-980) and decreasing the tumorigenicity of colorectal cancer (Hung-Gu et al., Journal of Biological Chemistry. (2011) 286: 17672-17681).

Examples of compounds that reportedly have inhibitory activity on DDR1 include 3-(2-(pyrazolo[1,5-a]pyrimidin-6-yl)ethinyl)benzamide derivatives (WO 2012/000304 and Ding et al., Journal of Medicinal Chemistry. (2013) 56; 3281-3295), 4-((4-ethylpiperazinyl)methyl)-3-trifluoromethylbenzamide derivatives (Gray et al., ACS Chemical Biology. (2013) 8: 2145-2150), and 4-piperazinylmethyl-3-trifluoromethylbenzamide derivatives (WO 2013/161851 and WO 2013/161853).

On the other hand, among those compounds having a urea skeleton, for example, 2,3-dihydro-1H-inden-2-ylurea derivatives (WO 2011/040509) are reported to be compounds with inhibitory activity on p38MAPK, while pentafluorosulfanyl-phenyl urea derivatives (WO 2012/094451) are reported to be compounds with inhibitory activity on FLT3 (Fms-like tyrosine kinase 3) and VEGFR2 (Vascular Endothelial Growth Factor Receptor 2).

However, no compound with inhibitory activity on DDR1 has been reported in the compounds having a urea skeleton.

Thus, it could be helpful to provide a compound with inhibitory activity on DDR1.

SUMMARY

We found that a novel urea derivative or a pharmaceutically acceptable salt thereof has inhibitory activity on DDR1 (hereinafter referred to as DDR1 inhibition activity).

We thus provide a urea derivative represented by Formula (I) below:

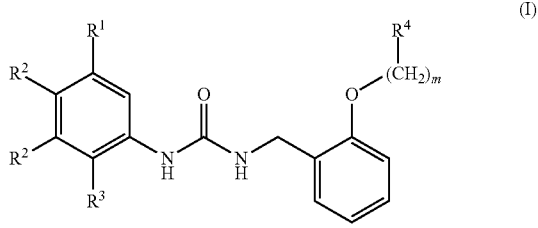

wherein m is 0 or 1; $R^1$ is a halogen atom, trifluoromethyl, trifluoromethoxy, or pentafluorosulfanyl; $R^2$ is a hydrogen atom or methyl in which one hydrogen atom is replaced with hydroxyl, piperazinyl, or 4-methylpiperazinyl; $R^3$ is a hydrogen atom or $R^5O-$; $R^4$ is phenyl, pyridyl, or pyrimidinyl, which phenyl, pyridyl, or pyrimidinyl is optionally substituted; $R^5$ is $C_1$-$C_3$ alkyl, 3-oxetanyl, or 4-piperidyl, (excluding the cases where m is 0; $R^1$ is a halogen atom, trifluoromethyl, or trifluoromethoxy; and $R^4$ is pyridyl which is optionally substituted), or a pharmaceutically acceptable salt thereof.

In the urea derivative represented by Formula (I) above, preferably, $R^4$ is 3- or 4-carbamoylphenyl, 4-N-methylcarbomoylphenyl, 4-pyridyl, or 2-(1H-imidazolyl)-4-pyrimidinyl.

In this case, high DDR1 inhibition activity can be expected.

Moreover, in the urea derivative represented by Formula (I) above, preferably, m is 0.

In this case, higher DDR1 inhibition activity can be expected.

Furthermore, in the urea derivative represented by Formula (I) above, more preferably, $R^4$ is 3- or 4-carbamoylphenyl, 4-N-methylcarbamoylphenyl, 4-pyridyl, or 2-(1H-imidazolyl)-4-pyrimidinyl, and m is 0.

In this case, still higher DDR1 inhibition activity can be expected.

Also, we provide an inhibitor of DDR1 comprising, as an active ingredient, the urea derivative represented by Formula (I) above or a pharmaceutically acceptable salt thereof.

Our urea derivatives and pharmaceutically acceptable salts thereof have high DDR1 inhibition activity and therefore can be used as DDR1 inhibitors.

DETAILED DESCRIPTION

Our urea derivative is characteristically represented by Formula (I) below:

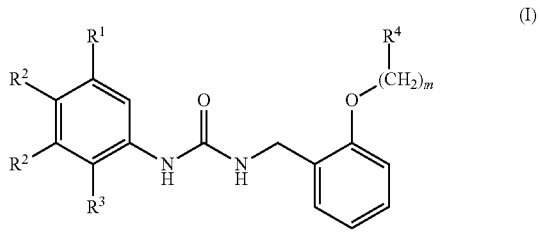

wherein m is 0 or 1; $R^1$ is a halogen atom, trifluoromethyl, trifluoromethoxy, or pentafluorosulfanyl; $R^2$ is a hydrogen atom or methyl in which one hydrogen atom is replaced with hydroxyl, piperazinyl, or 4-methylpiperazinyl; $R^3$ is a hydrogen atom or $R^5O-$; $R^4$ is phenyl, pyridyl, or pyrimidinyl, which phenyl, pyridyl, or pyrimidinyl is optionally substituted; $R^5$ is $C_1$-$C_3$ alkyl, 3-oxetanyl, or 4-piperidyl, (excluding the cases where m is 0; $R^1$ is a halogen atom, trifluoromethyl, or trifluoromethoxy; and $R^4$ is pyridyl which is optionally substituted).

Unless otherwise specified, the following terms used herein are as defined below.

The term "halogen atom" means fluorine atom, chlorine atom, bromine atom, or iodine atom.

The term "phenyl which is optionally substituted" means phenyl in which one of the hydrogen atoms is optionally substituted by carbonyl, and the term includes, for example, phenyl, 3- or 4-carboxylphenyl, 3- or 4-carbamoylphenyl, 4-N-methylcarbamoylphenyl, 4-N-(2-(methylamino)ethyl)carbamoylphenyl, 4-N-(2-(dimethylamino)ethyl)carbamoylphenyl, 4-N-(2-(diethylamino)ethyl)carbamoylphenyl, 4-N,N-dimethylcarbamoylphenyl, or 3- or 4-methoxycarbonylphenyl.

The term "pyridyl which is optionally substituted" means pyridyl in which one of the hydrogen atoms is optionally substituted by carbonyl, and the term includes, for example, pyridyl, 2-carbamoyl-4-pyridyl, 3-carbamoyl-6-pyridyl, or 3-N-methylcarbamoyl-6-pyridyl.

The term "pyrimidinyl which is optionally substituted" means pyrimidinyl in which one of the hydrogen atoms is optionally substituted by imidazolyl, and the term includes, for example, pyrimidinyl or 2-(1H-imidazolyl)-4-pyrimidinyl.

The term "$C_1$-$C_3$ alkyl" means methyl, ethyl, propyl, or isopropyl.

Specific examples of preferable urea derivatives represented by Formula (I) above are indicated in Table 1, but this disclosure is not limited thereto.

TABLE 1

| Structural Formula |
| --- |

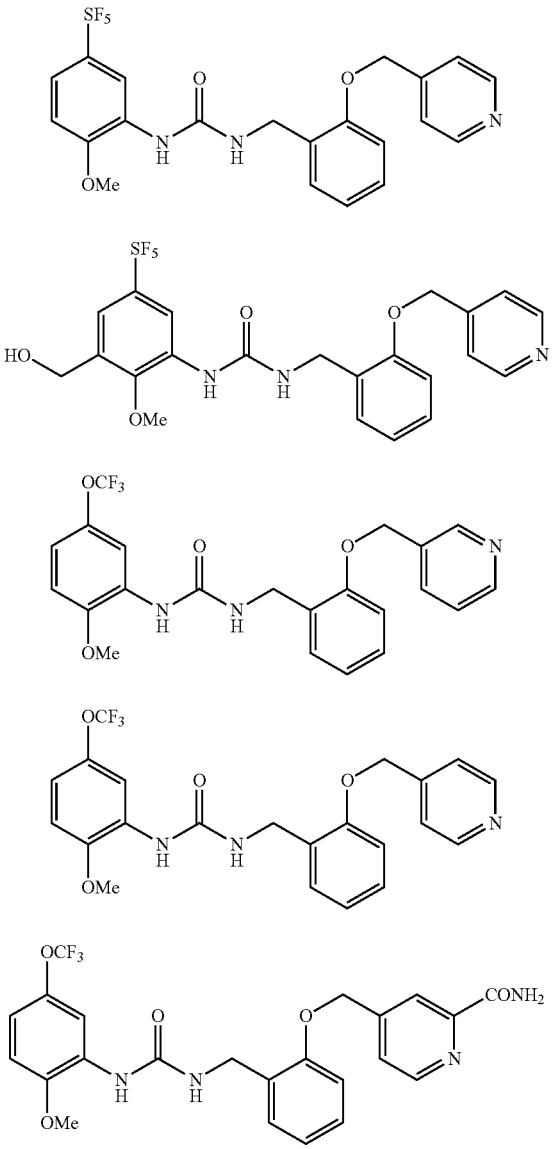

TABLE 1-continued
Structural Formula
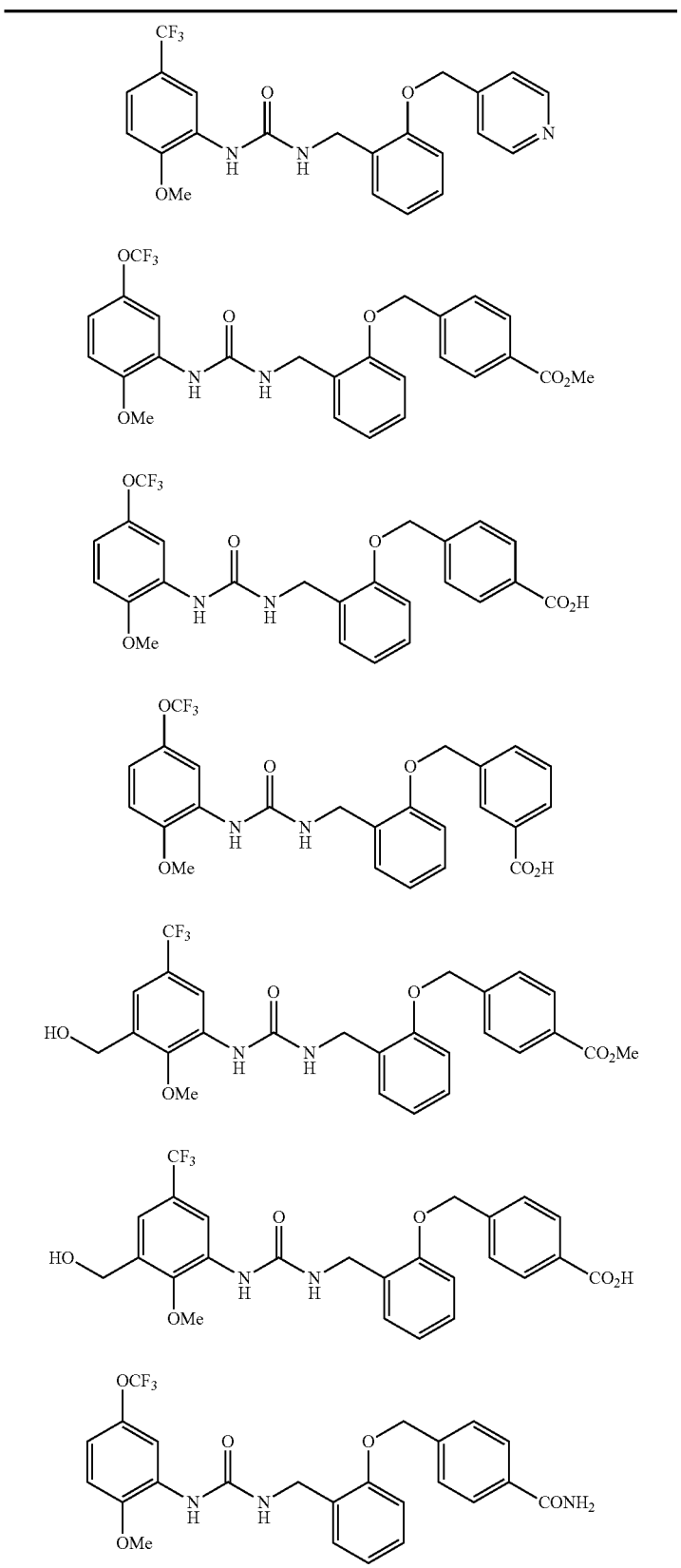

TABLE 1-continued
Structural Formula
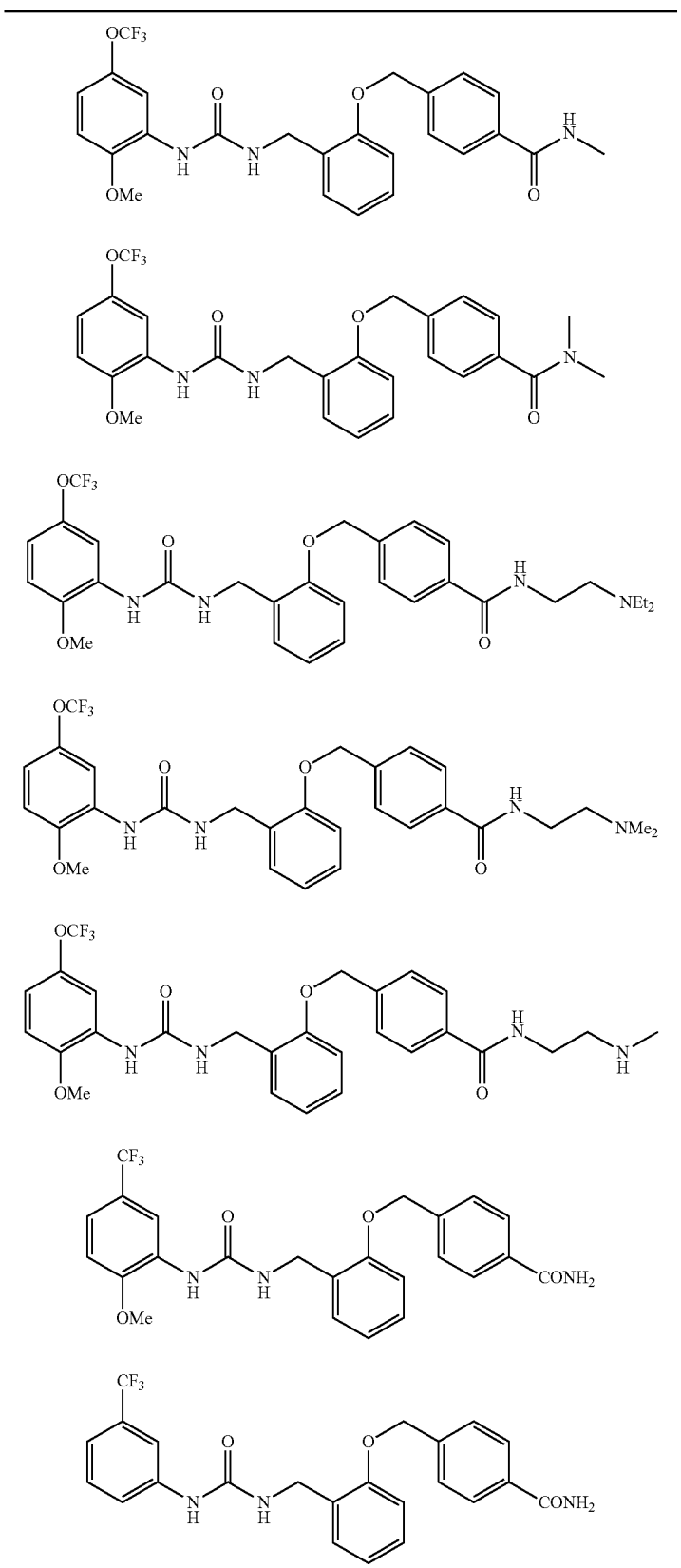

TABLE 1-continued

Structural Formula

TABLE 1-continued
Structural Formula
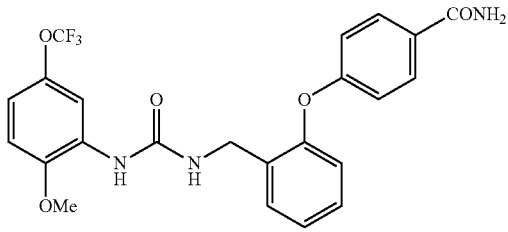
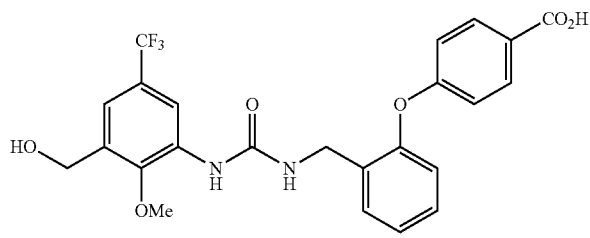 [SMILES: COc1c(CO)cc(C(F)(F)F)cc1NC(=O)NCc1ccccc1Oc1ccc(C(=O)O)cc1]
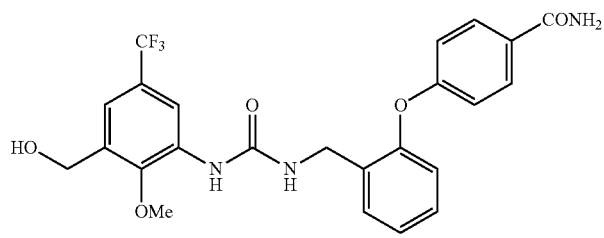 [SMILES: COc1c(CO)cc(C(F)(F)F)cc1NC(=O)NCc1ccccc1Oc1ccc(C(N)=O)cc1]
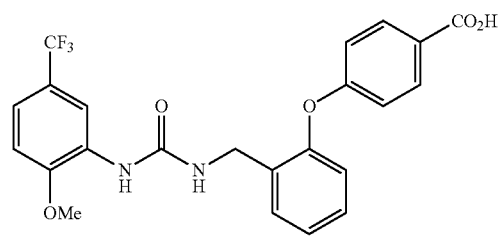 [SMILES: COc1ccc(C(F)(F)F)cc1NC(=O)NCc1ccccc1Oc1ccc(C(=O)O)cc1]
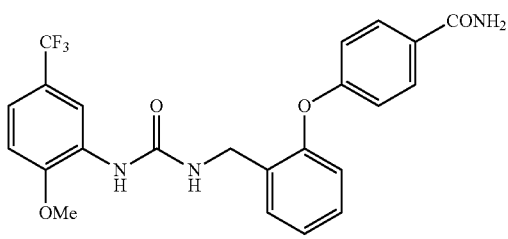
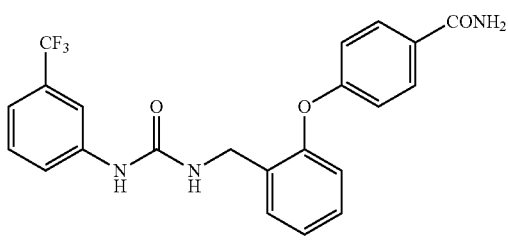 [SMILES: NC(=O)c1ccc(Oc2ccccc2CNC(=O)Nc2cccc(C(F)(F)F)c2)cc1]

TABLE 1-continued
Structural Formula
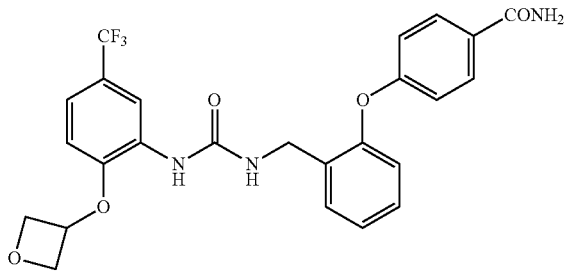 [SMILES: NC(=O)c1ccc(Oc2ccccc2CNC(=O)Nc2cc(C(F)(F)F)ccc2OC2COC2)cc1]
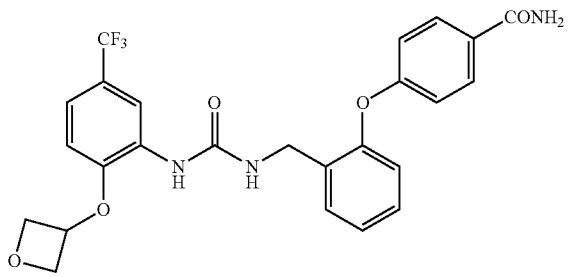 [SMILES: NC(=O)c1ccc(Oc2ccccc2CNC(=O)Nc2cc(C(F)(F)F)ccc2OC2COC2)cc1]
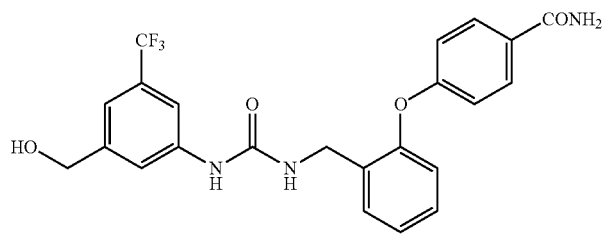 [SMILES: NC(=O)c1ccc(Oc2ccccc2CNC(=O)Nc2cc(CO)cc(C(F)(F)F)c2)cc1]
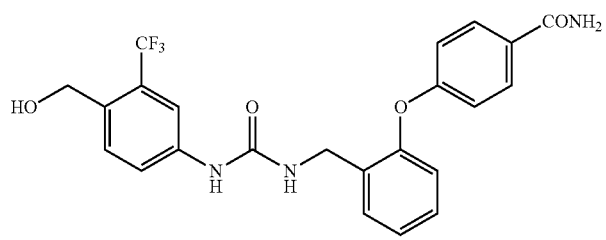 [SMILES: NC(=O)c1ccc(Oc2ccccc2CNC(=O)Nc2ccc(CO)c(C(F)(F)F)c2)cc1]
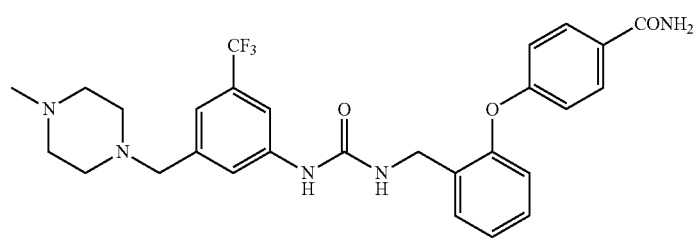 [SMILES: CN1CCN(Cc2cc(NC(=O)NCc3ccccc3Oc3ccc(C(N)=O)cc3)cc(C(F)(F)F)c2)CC1]
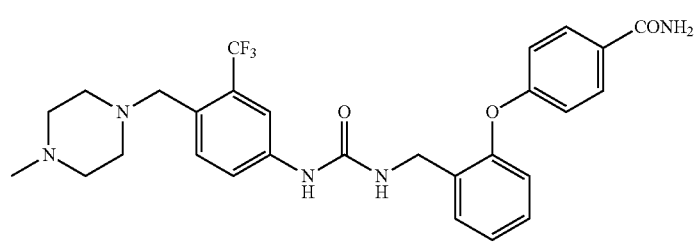 [SMILES: CN1CCN(Cc2ccc(NC(=O)NCc3ccccc3Oc3ccc(C(N)=O)cc3)cc2C(F)(F)F)CC1]

TABLE 1-continued
Structural Formula
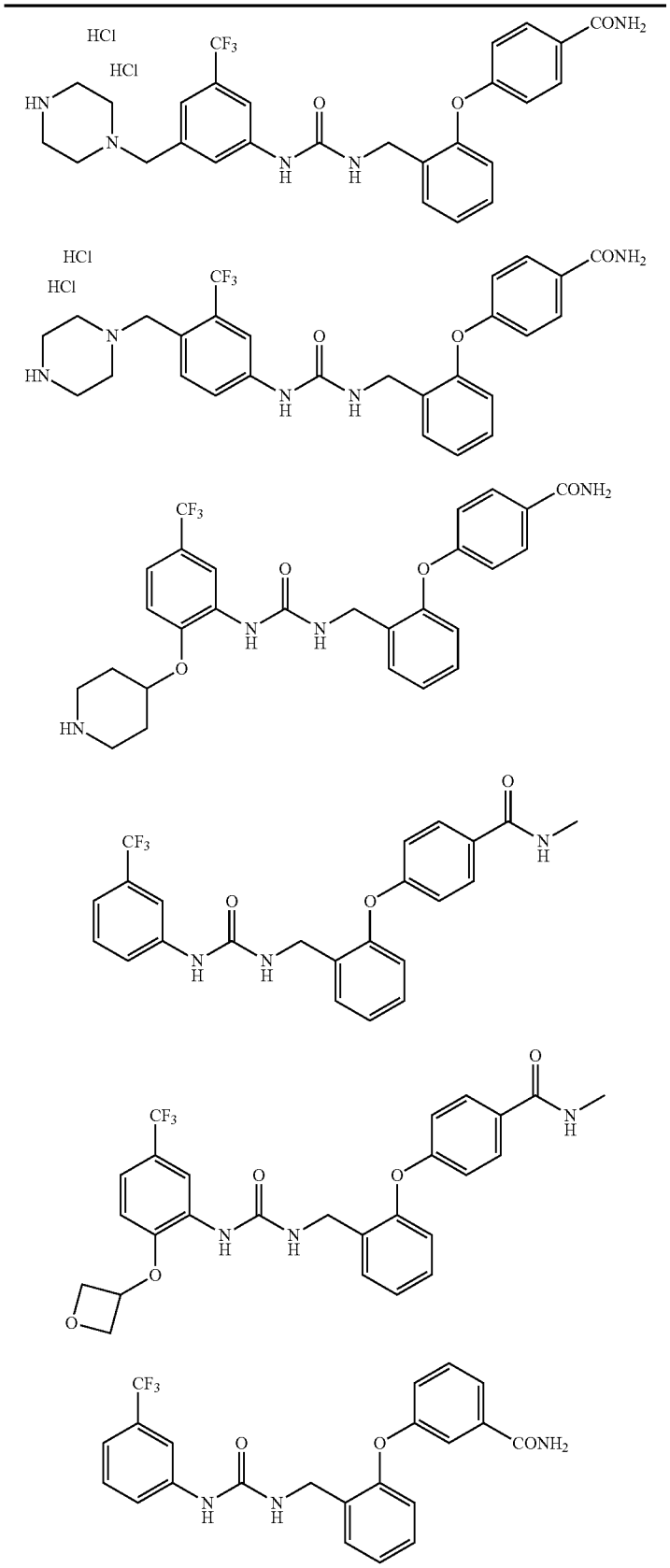

TABLE 1-continued
Structural Formula
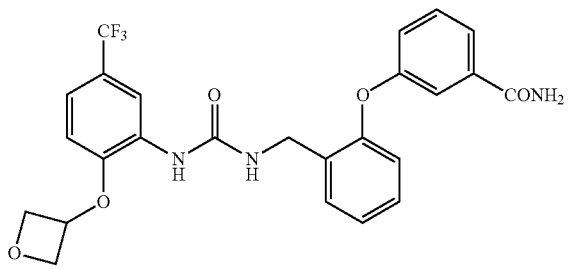 [SMILES: NC(=O)c1cccc(Oc2ccccc2CNC(=O)Nc2cc(C(F)(F)F)ccc2OC2COC2)c1]
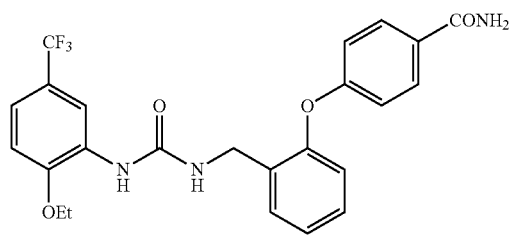 [SMILES: CCOc1ccc(C(F)(F)F)cc1NC(=O)NCc1ccccc1Oc1ccc(C(N)=O)cc1]
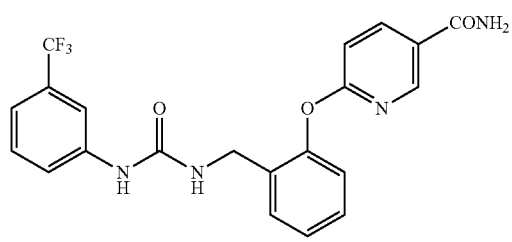
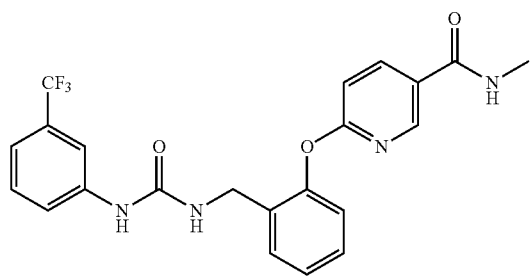 [SMILES: CNC(=O)c1ccc(Oc2ccccc2CNC(=O)Nc2cccc(C(F)(F)F)c2)nc1]
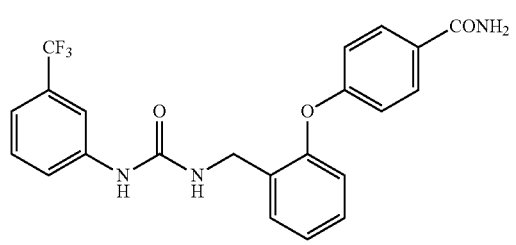

TABLE 1-continued

Structural Formula

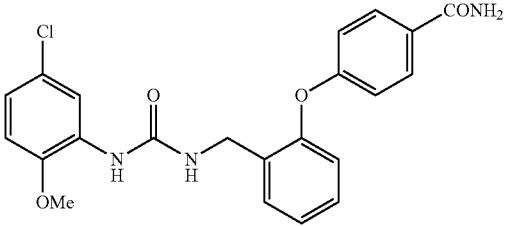 [SMILES: COc1ccc(Cl)cc1NC(=O)NCc1ccccc1Oc1ccc(C(N)=O)cc1]

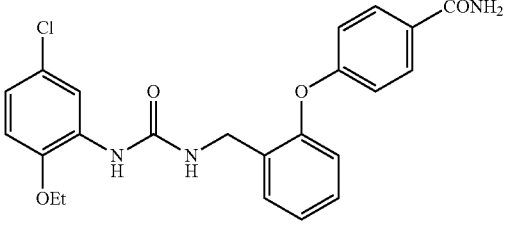

Optical isomers and diastereomers can exist for a urea derivative represented by Formula (I) above (hereinafter referred to as urea derivative (I)), and the urea derivative includes racemic and diastereomeric mixtures as well as each single isomer.

We also provide a prodrug of the urea derivative (I) or a pharmaceutically acceptable salt thereof. The prodrug of the urea derivative (I) refers to a compound which is enzymatically or chemically converted in vivo to the urea derivative (I). The activity of a prodrug of the urea derivative (I) is attributable to the urea derivative (I) but the prodrug itself of the urea derivative (I) may have some activity.

Examples of a prodrug of the urea derivative (I) include compounds in which a hydroxyl group of the urea derivative (I) is substituted by alkyl, phosphate, or borate. These compounds can be synthesized from the urea derivative (I) according to known methods.

Moreover, the prodrug of the urea derivative (I) may be a prodrug converted to the urea derivative (I) under the physiological conditions described in a known document ("Development of Pharmaceutical Product", Hirokawa Shoten Co., 1990, Vol. 7, pp. 163-198; and Progress in Medicine, 1985, Vol. 5, pp. 2157-2161).

The urea derivative (I) may be labeled with an isotope, and examples of the isotope used for labeling include $^2$H, $^3$H, $^{13}$C, $^{14}$C, $^{15}$N, $^{15}$O, $^{18}$O and/or $^{125}$I.

Examples of "pharmaceutically acceptable salts" of the urea derivative (I) include inorganic acid salts such as hydrochloride, sulfate, nitrate, hydrobromide, hydroiodide, or phosphate; or organic acid salts such as oxalate, malonate, citrate, fumarate, lactate, malate, succinate, tartrate, acetate, trifluoroacetate, maleate, gluconate, benzoate, ascorbate, glutarate, mandelate, phthalate, methanesulfonate, ethanesulfonate, benzenesulfonate, p-toluenesulfonate, camphorsulfonate, aspartate, glutamate, or cinnamate, and preferably include a hydrochloride, sulfate, hydrobromide, maleate, benzoate or methanesulfonate.

The urea derivative (I) or a pharmaceutically acceptable salt thereof may be an anhydrate or may have formed a solvate such as hydrate. The solvate herein is preferably a pharmaceutically acceptable solvate. The pharmaceutically acceptable solvate either may be or may not be a hydrate, but preferably it is a hydrate. Examples of the solvent constituent in the solvate include alcohol-based solvents such as methanol, ethanol, or n-propanol; N,N-dimethylformamide, dimethyl sulfoxide, or water.

The urea derivative (I) can be produced by an appropriate method based on its basic skeleton and features derived from the types of substituents. In addition, the starting materials and reagents used for the production of these compounds are generally commercially available or can be produced by known methods.

The urea derivative (I) as well as the intermediates and starting materials for use in the production of the derivative can be isolated and purified by known procedures. Examples of the known procedures for isolation and purification include solvent extraction, recrystallization, or chromatography.

If the urea derivative (I) includes optical isomers or stereoisomers, each isomer can be obtained as a single compound by known methods. Examples of the known methods include crystallization, enzymatic resolution, or chiral chromatography.

In the production method as described below, if any raw material compound contains hydroxyl group, amino group, or carboxyl group, a protective group may be introduced to each of these groups in each reaction and a compound of interest can be obtained subsequent to the reaction by removing the protective group as necessary.

Examples of the protective group for hydroxyl group include trityl group, aralkyl group having 7 to 10 carbon atoms (for example, benzyl group), or substituted silyl group (for example, trimethylsilyl group, triethylsilyl group, or tert-butyldimethylsilyl group).

Examples of the protective group for amino group include alkylcarbonyl group having 2 to 6 carbon atoms (for example, acetyl group), benzoyl group, alkyloxycarbonyl group having 2 to 8 carbon atoms (for example, tert-butoxycarbonyl group or benzyloxycarbonyl group), aralkyl group having 7 to 10 carbon atoms (for example, benzyl group), or phthaloyl group.

Examples of the protective group for carboxyl group include alkyl group having 1 to 6 carbon atoms (for example, methyl group, ethyl group or tert-butyl group), or aralkyl group having 7 to 10 carbon atoms (for example, benzyl group).

Protective groups are removed in different ways depending on the type of the protective groups, but the deprotection may be performed according to a known method (for example, Greene, T. W., "Greene's Protective Groups in Organic Synthesis", Wiley-Interscience) or an equivalent method.

A urea derivative (I) can be obtained, for example, via urea coupling between an aniline derivative (II) and a benzylamine derivative (III) in the presence of a urea coupling agent and a base, as shown in Scheme 1.

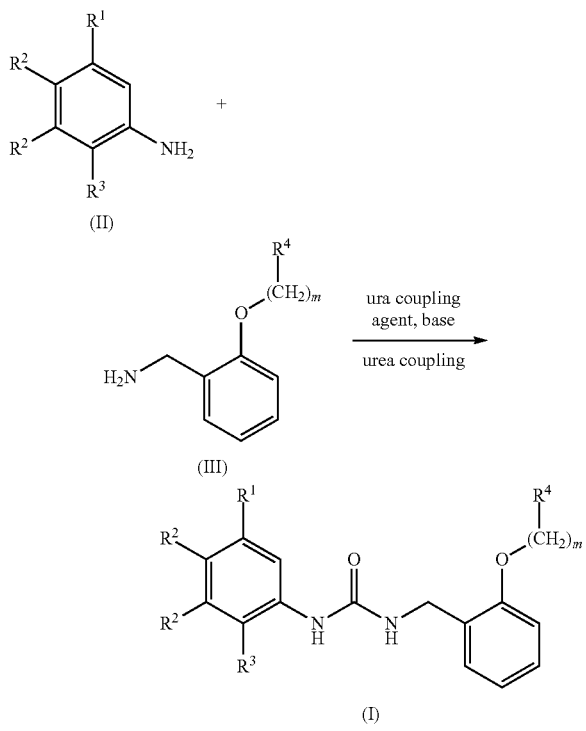

(wherein m and $R^1$-$R^4$ are as defined above.)

The amount of the benzylamine derivative (III) for use in the urea coupling reaction is preferably 0.5 to 10 equivalents, more preferably 1 to 3 equivalents, to the aniline derivative (II).

Examples of the urea coupling agent for use in the urea coupling reaction include chloroformate derivatives such as 2,2,2-trichloroethyl chloroformate, phenyl chloroformate, or p-nitrophenyl chloroformate; triphosgene, phosgene, N,N'-carbonyldiimidazole, or N,N'-disuccinimidyl carbonate, and preferably include chloroformate derivatives such as 2,2,2-trichloroethyl chloroformate, phenyl chloroformate, or p-nitrophenyl chloroformate; or triphosgene.

The amount of the urea coupling agent for use in the urea coupling reaction is preferably 0.1 to 100 equivalents, more preferably 0.3 to 30 equivalents, to the aniline derivative (II).

Examples of the base for use in the urea coupling reaction include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixture thereof, and preferably include organic bases such as triethylamine or diisopropylethylamine.

The amount of the base for use in the urea coupling reaction is preferably 1 to 100 equivalents, more preferably 2 to 30 equivalents, to the aniline derivative (II).

A reaction solvent for use in the urea coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or nitrile-based solvents such as acetonitrile or propionitrile.

The reaction temperature of the urea coupling reaction is preferably −40° C. to 200° C., more preferably −20° C. to 150° C.

The reaction time of the urea coupling reaction is appropriately selected depending on the conditions such as reaction temperature, and is preferably 30 minutes to 30 hours.

The concentration of the aniline derivative (II) for use in the urea coupling reaction is preferably 1 mmol/L to 1 mol/L at the start of the reaction.

A microwave reactor may be used as necessary in the urea coupling reaction.

The aniline derivative (II) for use in the urea coupling reaction is commercially available or can also be produced by a known method.

Among aniline derivatives (II), a derivative (IIb) in which $R^2$ represents hydroxymethyl can be obtained, for example, by reduction of an alkyl ester derivative (IIa), as shown in Scheme 2.

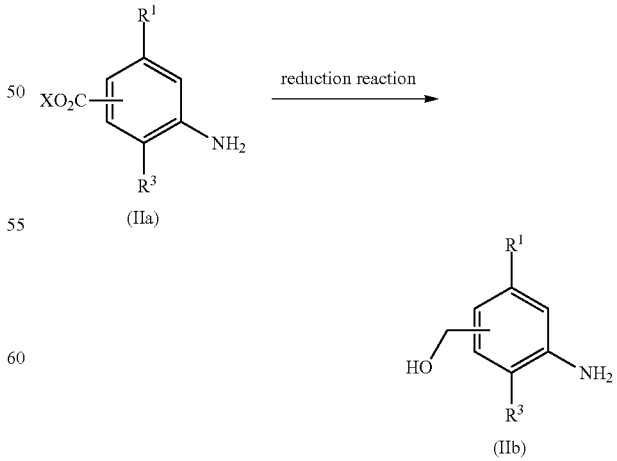

(wherein X is methyl or ethyl, and other symbols are as defined above.)

Examples of the reduction reaction include catalytic hydrogenation reaction under hydrogen atmosphere in the presence of a metal catalyst such as palladium, nickel, or platinum; hydride reduction reaction with a metal hydride reagent such as lithium aluminum hydride, borane-dimethylsulfide complex, or borane-tetrahydrofuran complex; or one-electron reduction reaction with a metal catalyst such as zinc, iron, or tin, in the presence of an acid, and a metal hydride reagent such as lithium aluminum hydride, borane-dimethylsulfide complex, or borane-tetrahydrofuran complex, is preferable.

A reaction solvent for use in the reduction reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include ether-based solvents such as diethyl ether, tetrahydrofuran, dimethoxyethane, or 1,4-dioxane.

The reaction temperature of the reduction reaction is preferably 0° C. to 200° C., more preferably 0° C. to 100° C.

The concentration of the alkyl ester derivative (IIa) for use in the reduction reaction is preferably 1 mmol/L to 1 mol/L at the start of the reaction.

The aniline derivative (II) can be obtained, for example, by reduction reaction of a nitrobenzene derivative (IV), as shown in Scheme 3.

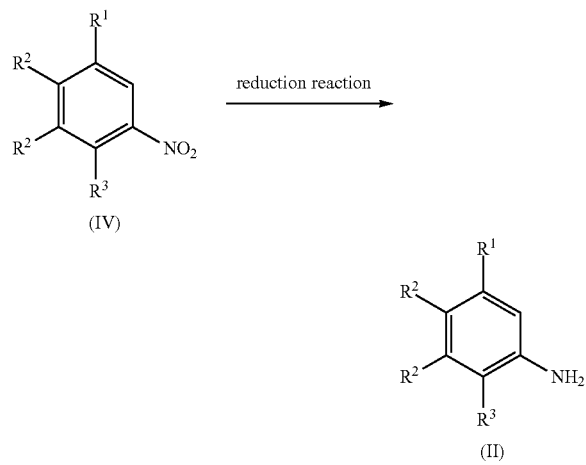

Scheme 3

(wherein each symbol is as defined above.)

Examples of the reduction reaction include catalytic hydrogenation reaction under hydrogen atmosphere in the presence of a metal catalyst such as palladium, nickel, or platinum; hydride reduction reaction with a metal hydride reagent such as lithium aluminum hydride, borane-dimethylsulfide complex, or borane-tetrahydrofuran complex; or one-electron reduction reaction with a metal catalyst such as zinc, iron, or tin, in the presence of an acid, and preferably include catalytic hydrogenation reaction under hydrogen atmosphere in the presence of a metal catalyst such as palladium, nickel, or platinum; or one-electron reduction reaction with a metal catalyst such as zinc, iron, or tin, in the presence of an acid; and the like.

Examples of the metal catalyst for use in the catalytic hydrogenation reaction include palladium, nickel, platinum, or any of them on carbon support.

The amount of the metal catalyst for use in the catalytic hydrogenation reaction is preferably 0.001 to 5 equivalents, more preferably 0.01 to 1 equivalent, to the nitrobenzene derivative (IV).

A reaction solvent for use in the catalytic hydrogenation reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol.

The pressure of the hydrogen gas for use in the catalytic hydrogenation reaction is preferably 1 to 10 atmospheres, more preferably 1 to 3 atmospheres.

The reaction temperature of the catalytic hydrogenation reaction is preferably 0-200° C., more preferably 0-100° C.

The reaction time of the catalytic hydrogenation reaction is appropriately selected depending on the conditions such as reaction temperature, and is preferably 1 to 72 hours.

Examples of the acid for use in the one-electron reduction reaction include acetic acid, hydrochloric acid, or ammonium chloride.

Examples of the metal catalyst for use in the one-electron reduction reaction include zinc, iron, tin, or a halide thereof.

The amount of the metal catalyst for use in the one-electron reduction reaction is preferably 0.1 to 100 equivalents, more preferably 1 to 50 equivalents, to the nitrobenzene derivative (IV).

A reaction solvent for use in the one-electron reduction reaction is appropriately selected depending on the type of reagents to be used, but it is not particularly limited as long as the reaction is not inhibited. Examples of the reaction solvent include acidic solvents such as hydrochloric acid or acetic acid; alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include acidic solvents such as hydrochloric acid or acetic acid; or alcohol-based solvents such as methanol or ethanol.

The reaction temperature of the one-electron reduction reaction is preferably 0° C. to 200° C., more preferably 0° C. to 100° C.

The reaction time of the one-electron reduction reaction is appropriately selected depending on the conditions such as reaction temperature, and is preferably 1 to 72 hours.

The concentration of the nitrobenzene derivative (IV) for use in the reduction reaction is preferably 1 mmol/L to 1 mol/L at the start of the reaction.

Among nitrobenzene derivatives (IV) as described above, a derivative (IVa) in which $R^3$ represents alkoxy can be obtained, for example, by nucleophilic substitution reaction of a halogenated nitrobenzene derivative (V) by an alcohol (VI), as shown in Scheme 4.

Scheme 4

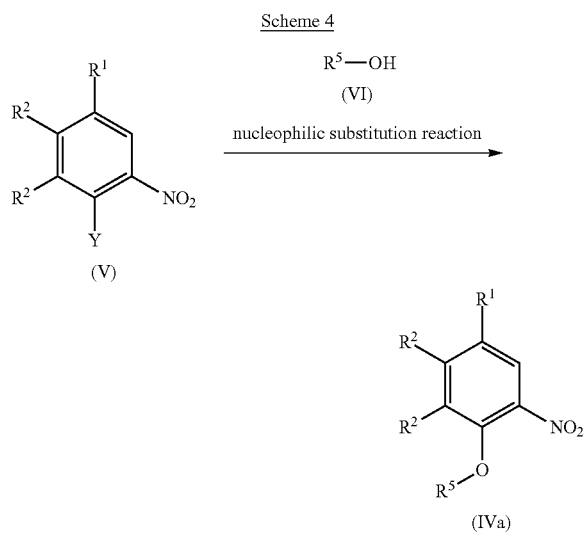

(wherein Y is a fluorine atom or chlorine atom, and other symbols are as defined above.)

The alcohol (VI) for use in the nucleophilic substitution reaction is commercially available. Moreover, it can also be produced by a known method or an equivalent method.

The amount of the alcohol (VI) for use in the nucleophilic substitution reaction is preferably 0.5 to 20 equivalents, more preferably 1 to 3 equivalents, to the halogenated nitrobenzene derivative (V).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the halogenated nitrobenzene derivative (V).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, N-methyl-2-pyrrolidone, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the halogenated nitrobenzene derivative (V) for use in the nucleophilic substitution reaction is preferably 1 mmol/L to 1 mol/L at the start of the reaction.

Among nitrobenzene derivatives (IV) as described above, a 3-hydroxymethylnitrobenzene derivative (IVb) can be obtained, for example, by reduction reaction of a 3-formylnitrobenzene derivative (VII), as shown in Scheme 5.

Scheme 5

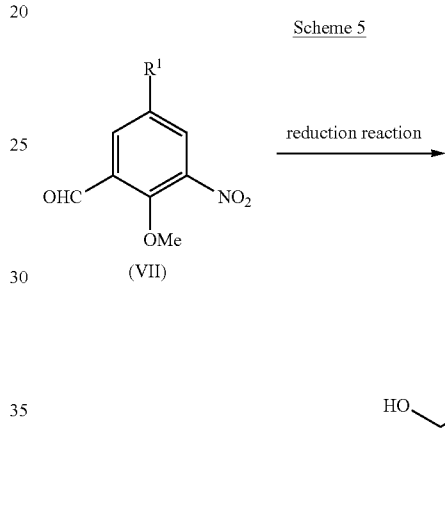

(wherein each symbol is as defined above.)

Examples of a reducing agent for use in the reduction reaction include aluminum-based reducing agents such as lithium aluminum hydride or diisobutylaluminum hydride; or boron-based reducing agents such as sodium borohydride or lithium borohydride, and preferably include boron-based reducing agents such as sodium borohydride or lithium borohydride.

The amount of the reducing agent for use in the reduction reaction is preferably 0.2 to 20 equivalents, more preferably 1 to 10 equivalents, to the 3-formylnitrobenzene derivative (VII).

A reaction solvent for use in the reduction reaction is appropriately selected depending on the type of reagents to be used, but it is not particularly limited as long as the reaction is not inhibited. Examples of the reaction solvent include alcohol-based solvents such as methanol, ethanol, isopropyl alcohol or tert-butyl alcohol; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; or mixed solvents thereof, and preferably include alcohol-based solvents such as methanol, ethanol, isopropyl alcohol or tert-butyl alcohol.

The reaction temperature of the reduction reaction is preferably −78° C. to 200° C., more preferably −20° C. to 100° C.

The reaction time of the reduction reaction is appropriately selected depending on the conditions such as reaction temperature, and is preferably 1 to 30 hours.

The concentration of the 3-formylnitrobenzene derivative (VII) for use in the reduction reaction is preferably 1 mmol/L to 1 mol/L at the start of the reaction.

The above-described 3-formylnitrobenzene derivative (VII) can be obtained, for example, by nitration reaction of a 2-formyl-anisole derivative (VIII), as shown in Scheme 6.

Scheme 6

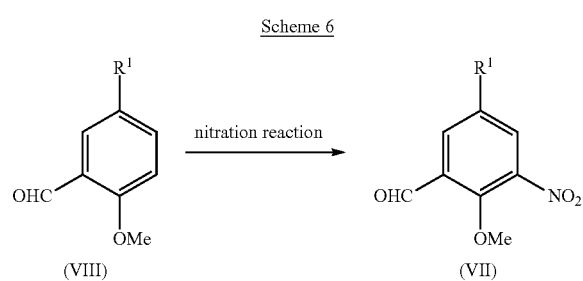

Scheme 7

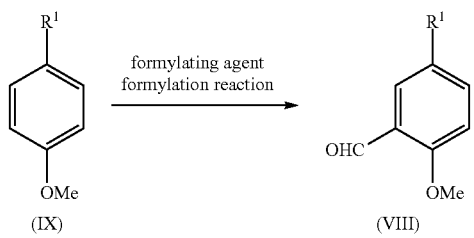

(wherein each symbol is as defined above.)

The anisole derivative (IX) for use in the formylation reaction is commercially available. Moreover, it can also be produced by a known method or an equivalent method.

Examples of a formylating agent for use in the formylation reaction include dihalomethyl alkyl ether derivatives such as dichloromethyl methyl ether, dichloromethyl ethyl ether, or dichloromethyl isopropyl ether; or formamide derivatives such as N,N-dimethylformamide or N-formylpiperidine, and preferably include dihalomethyl alkyl ether derivatives such as dichloromethyl methyl ether, dichloromethyl ethyl ether, or dichloromethyl isopropyl ether.

The amount of the formylating agent for use in the formylation reaction is preferably 0.5 to 20 equivalents, more preferably 1 to 5 equivalents, to the anisole derivative (IX).

(wherein each symbol is as defined above.)

Examples of the nitrating agent for use in the nitration reaction include nitric acid products such as concentrated nitric acid or fuming nitric acid, or nitronium salts such as nitronium tetrafluoroborate, and preferably include nitric acid products such as concentrated nitric acid or fuming nitric acid.

The amount of the nitrating agent for use in the nitration reaction is preferably 0.5 to 20 equivalents, more preferably 0.5 to 10 equivalents, to the 2-formyl-anisole derivative (VIII).

A reaction solvent for use in the nitration reaction is appropriately selected depending on the type of reagents to be used, but it is not particularly limited as long as the reaction is not inhibited. Examples of the reaction solvent include acidic solvents such as concentrated sulfuric acid or acetic anhydride; or chlorine-based solvents such as dichloromethane, chloroform, or 1,2-dichloroethane, and preferably include acidic solvents such as concentrated sulfuric acid or acetic anhydride.

The reaction temperature of the nitration reaction is preferably −20° C. to 200° C., more preferably 0° C. to 100° C.

The reaction time of the nitration reaction is appropriately selected depending on the conditions such as reaction temperature, and is preferably 1 to 72 hours.

The concentration of the 2-formyl-anisole derivative (VIII) for use in the nitration reaction is preferably 1 mmol/L to 1 mol/L at the start of the reaction.

The above-described 2-formyl-anisole derivative (VIII) can be obtained, for example, by formylation reaction of an anisole derivative (IX) in the presence of an acid, as shown in Scheme 7.

Examples of the acid for use in the formylation reaction include Lewis acids such as aluminium trichloride, tin tetrachloride, titanium tetrachloride, or boron trifluoride; or phosphorus compounds such as phosphorus oxychloride or phosphorus oxybromide, and preferably include Lewis acids such as aluminium trichloride, tin tetrachloride, titanium tetrachloride, or boron trifluoride.

The amount of the acid for use in the formylation reaction is preferably 0.5 to 20 equivalents, more preferably 1 to 5 equivalents, to the anisole derivative (IX).

A reaction solvent for use in the formylation reaction is appropriately selected depending on the type of reagents to be used, but it is not particularly limited as long as the reaction is not inhibited. Examples of the reaction solvent include halogen-based solvents such as dichloromethane, chloroform, 1,2-dichloroethane, or carbon tetrachloride; or ether-based solvents such as tetrahydrofuran, diethyl ether, 1,4-dioxane, or ethylene glycol dimethyl ether, and preferably include halogen-based solvents such as dichloromethane, chloroform, 1,2-dichloroethane, or carbon tetrachloride.

The reaction temperature of the formylation reaction is preferably −78° C. to 100° C., more preferably −30° C. to 50° C.

The reaction time of the formylation reaction is appropriately selected depending on the conditions such as reaction temperature, and is preferably 10 minutes to 30 hours.

The concentration of the anisole derivative (IX) for use in the formylation reaction is preferably 1 mmol/L to 1 mol/L at the start of the reaction.

The benzylamine derivative (III) can be obtained, for example, by deprotection of a protected benzylamine derivative (X), as shown in Scheme 8.

Scheme 8

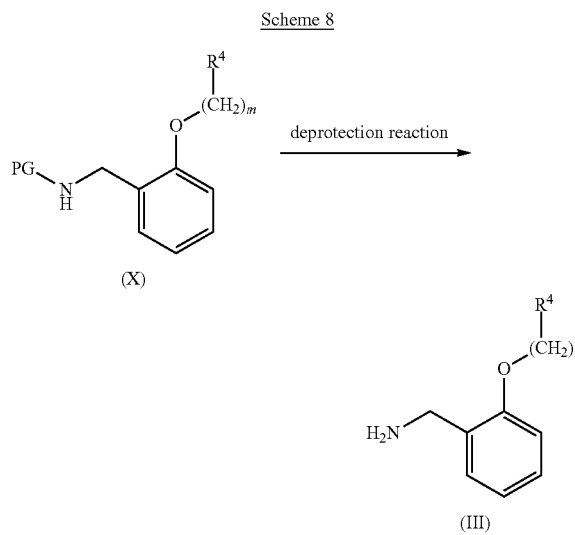

(wherein PG is a protective group, and other symbols are as defined above.)

Protective groups are removed in different ways depending on the type of the protective groups, but the deprotection may be performed according to a known method (for example, Greene, T. W., "Greene's Protective Groups in Organic Synthesis", Wiley-Interscience) or an equivalent method.

Among protected benzylamine derivatives (X) as described above, a derivative (Xa) in which m is 0 and $R^4$ represents an optionally substituted carbamoyl group can be obtained, for example, by condensation reaction of a carboxylic acid derivative (Xb) and an amine derivative (XI), as shown in Scheme 9.

Scheme 9

(wherein each of $R^6$ and $R^7$ independently represents a hydrogen atom, $C_1$-$C_3$ alkyl, 2-(methylamino) ethyl, 2-(dimethylamino) ethyl, or 2-(diethylamino) ethyl; Z represents CH or N; and other symbols are as defined above.)

The amount of the amine derivative (XI) for use in the condensation reaction is preferably 0.5 to 10 equivalents, more preferably 1 to 3 equivalents, to the carboxylic acid derivative (Xb).

Examples of a condensation reagent for use in the condensation reaction include ethyl chloroformate, oxalyl chloride, 1-ethyl-3-(3-dimethylaminopropyl)carbodiimide hydrochloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, and the like, and preferably include ethyl chloroformate or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (Xb).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include dichloromethane, chloroform, or aprotic polar solvents such as N,N-dimethylformamide, N,N-dimethylacetamide, N-methyl-2-pyrrolidone, or dimethyl sulfoxide.

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (Xb) for use in the condensation reaction is preferably 1 mmol/L to 1 mol/L at the start of the reaction.

The above-described carboxylic acid derivative (Xb) can be obtained, for example, by hydrolysis reaction of an alkyl ester derivative (Xc) in the presence of a base, as shown in Scheme 10.

Scheme 10

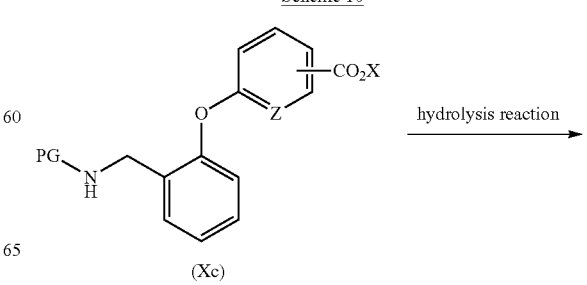

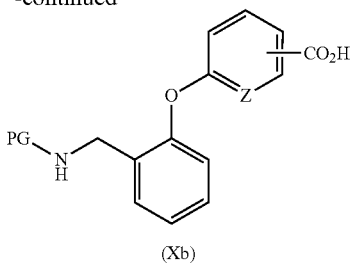

(Xb)

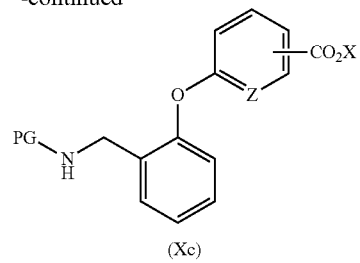

(Xc)

(wherein each symbol is as defined above.)

Examples of the base for use in the hydrolysis reaction include inorganic bases such as lithium hydroxide, sodium hydroxide, potassium hydroxide, barium hydroxide, or potassium carbonate.

The amount of the base for use in the hydrolysis reaction is preferably 0.5 to 20 equivalents, more preferably 1 to 3 equivalents, to the alkyl ester derivative (Xc).

A reaction solvent for use in the hydrolysis reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, N-methyl-2-pyrrolidone, or dimethyl sulfoxide; or ether-based solvents such as diethyl ether, tetrahydrofuran, dimethoxyethane, or 1,4-dioxane.

The reaction temperature of the hydrolysis reaction is preferably −20° C. to 200° C., more preferably 0-150° C.

The reaction time of the hydrolysis reaction is appropriately selected depending on the conditions such as reaction temperature, and is preferably 1 to 30 hours.

The concentration of the alkyl ester derivative (Xc) for use in the hydrolysis reaction is preferably 1 mmol/L to 1 mol/L at the start of the reaction.

The above-described alkyl ester derivative (Xc) can be obtained, for example, by reduction reaction and subsequent protection reaction of a benzonitrile derivative (XI), as shown in Scheme 11.

Scheme 11

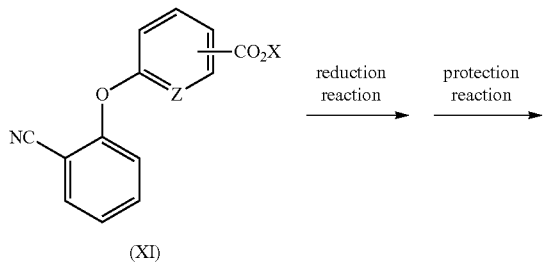

(XI)

(wherein each symbol is as defined above.)

Examples of the reduction reaction include catalytic hydrogenation reaction under hydrogen atmosphere in the presence of a metal catalyst such as palladium, nickel, or platinum; hydride reduction reaction with a metal hydride reagent such as lithium aluminum hydride, borane-dimethylsulfide complex, or borane-tetrahydrofuran complex; or one-electron reduction reaction with a metal catalyst such as zinc, iron, or tin, in the presence of an acid, and preferably include catalytic hydrogenation reaction under hydrogen atmosphere in the presence of a metal catalyst such as palladium, nickel, or platinum.

Examples of the metal catalyst for use in the catalytic hydrogenation reaction include palladium, nickel, platinum, or any of them on carbon support.

The amount of the metal catalyst for use in the catalytic hydrogenation reaction is preferably 0.001 to 5 equivalents, more preferably 0.01 to 1 equivalent, to the benzonitrile derivative (XI).

A reaction solvent for use in the catalytic hydrogenation reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol.

The pressure of the hydrogen gas for use in the catalytic hydrogenation reaction is preferably 1 to 10 atmospheres, more preferably 1 to 3 atmospheres.

The reaction temperature of the catalytic hydrogenation reaction is preferably 0-200° C., more preferably 0-100° C.

The reaction time of the catalytic hydrogenation reaction is appropriately selected depending on the conditions such as reaction temperature, and is preferably 1 to 72 hours.

The concentration of the benzonitrile derivative (XI) for use in the reduction reaction is preferably 1 mmol/L to 1 mol/L at the start of the reaction.

The protection of benzylamine is performed in different ways depending on the type of protective group but may be performed by a known method (for example, Greene, T. W., "Greene's Protective Groups in Organic Synthesis", Wiley-Interscience) or an equivalent method.

Among benzonitrile derivatives (XI) as described above, a derivative (XIa) in which Z is CH can be obtained, for example, by nucleophilic substitution reaction of a benzonitrile derivative (XII) with a phenol derivative (XIII), as shown in Scheme 12.

Scheme 12

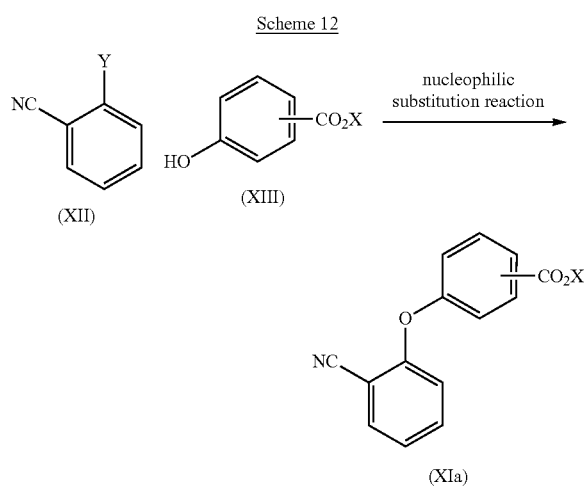

(wherein each symbol is as defined above.)

The benzonitrile derivative (XII) for use in the nucleophilic substitution reaction is commercially available. Moreover, it can also be produced by a known method.

The amount of the benzonitrile derivative (XII) for use in the nucleophilic substitution reaction is preferably 0.2 to 10 equivalents, more preferably 0.5 to 3 equivalents, to the phenol derivative (XIII).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the phenol derivative (XIII).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, N-methyl-2-pyrrolidone, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the phenol derivative (XIII) for use in the nucleophilic substitution reaction is preferably 1 mmol/L to 1 mol/L at the start of the reaction.

Among benzonitrile derivatives (XI) as described above, a derivative (XIb) in which Z is N can be obtained, for example, by nucleophilic substitution reaction of 2-hydroxybenzonitrile (XIV) with a halogenated pyridine derivative (XV), as shown in Scheme 13.

Scheme 13

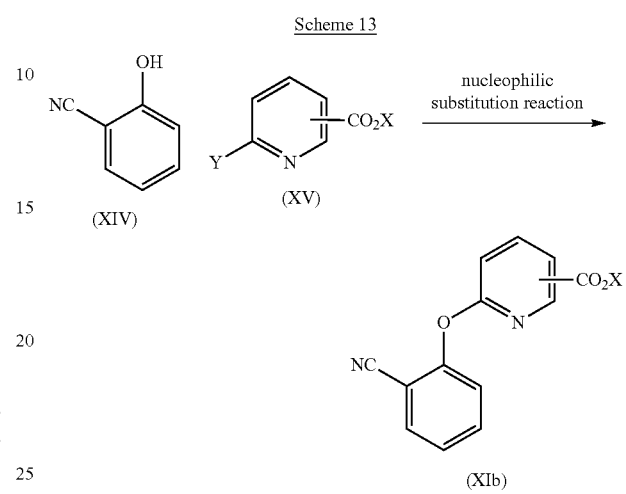

(wherein each symbol is as defined above.)

2-Hydroxybenzonitrile (XIV) for use in the nucleophilic substitution reaction is commercially available. Moreover, it can also be produced by a known method.

The amount of 2-hydroxybenzonitrile (XIV) for use in the nucleophilic substitution reaction is preferably 0.2 to 10 equivalents, more preferably 0.5 to 3 equivalents, to the halogenated pyridine derivative (XV).

The nucleophilic substitution reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to 2-hydroxybenzonitrile (XIV).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, N-methyl-2-pyrrolidone, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the halogenated pyridine derivative (XV) for use in the nucleophilic substitution is preferably 1 mmol/L to 1 mol/L at the start of the reaction.

Among urea derivatives (I) as described above, a derivative (Ia) in which m is 1 can be obtained, for example, by nucleophilic substitution reaction of a phenol derivative (XVI) with a halogenated alkyl derivative (XVII) in the presence of a base, as shown in Scheme 14.

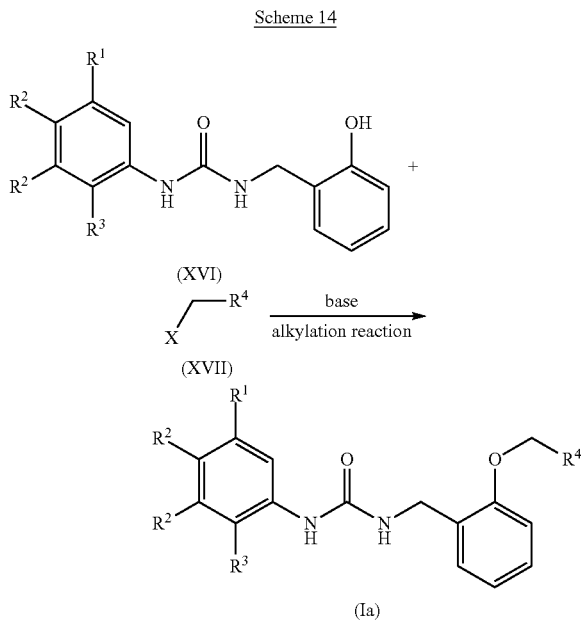

(wherein each symbol is as defined above.)

The above-described phenol derivative (XVI) can be produced by a known method or a method equivalent to Scheme 1.

The halogenated alkyl derivative (XVII) for use in the nucleophilic substitution reaction is commercially available. Moreover, it can also be produced by a known method.

The amount of the halogenated alkyl derivative (XVII) for use in the nucleophilic substitution reaction is preferably 0.2 to 10 equivalents, more preferably 0.5 to 3 equivalents, to the phenol derivative (XVI).

The nucleophilic substitution reaction may optionally be performed with a base. Examples of the base to be used include inorganic bases such as sodium hydride, sodium hydrogen carbonate, cesium carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the phenol derivative (XVI).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, N-methyl-2-pyrrolidone, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the phenol derivative (XVI) for use in the nucleophilic substitution reaction is preferably 1 mmol/L to 1 mol/L at the start of the reaction.

Among urea derivatives (I) as described above, a derivative (Ib) in which m is 0 can be obtained, for example, by nucleophilic substitution reaction of the phenol derivative (XVI) with a halogenated aryl or halogenated heteroaryl derivative (XVIII) in the presence of a base, as shown in Scheme 15.

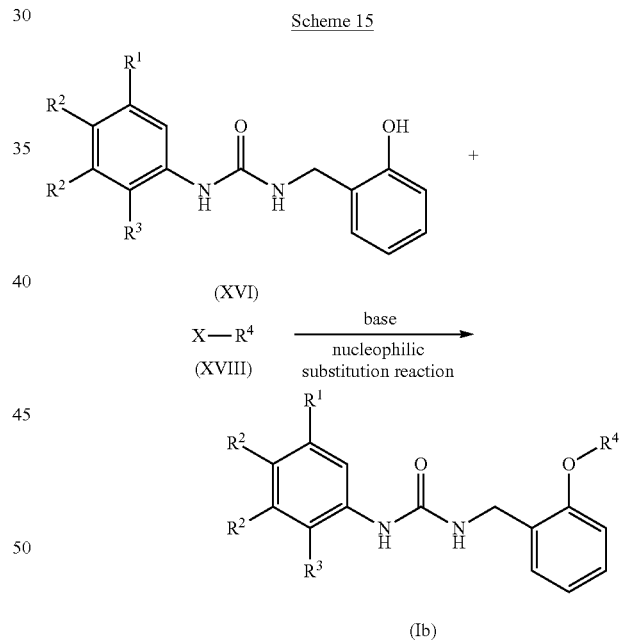

(wherein each symbol is as defined above.)

The amount of the phenol derivative (XVI) for use in the nucleophilic substitution reaction is preferably 0.2 to 10 equivalents, more preferably 0.5 to 3 equivalents, to the halogenated aryl or halogenated heteroaryl derivative (XVIII).

The nucleophilic substitution reaction may optionally be performed with a base. Examples of the base to be used include inorganic bases such as sodium hydride, sodium hydrogen carbonate, cesium carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the phenol derivative (XVI).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, N-methyl-2-pyrrolidone, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the phenol derivative (XVI) for use in the nucleophilic substitution reaction is preferably 1 mmol/L to 1 mol/L at the start of the reaction.

A microwave reactor may be used as necessary in the nucleophilic substitution reaction.

Among urea derivatives (Ia) as described above, a derivative (Iaa) in which $R^4$ represents an optionally substituted carbamoyl group can be obtained, for example, by condensation reaction of a carboxylic acid derivative (Iab) and the amine derivative (XI), as shown in Scheme 16.

The amount of the amine derivative (XI) for use in the condensation reaction is preferably 0.5 to 10 equivalents, more preferably 1 to 3 equivalents, to the carboxylic acid derivative (Iab).

Examples of a condensation reagent for use in the condensation reaction include ethyl chloroformate, oxalyl chloride, 1-ethyl-3-(3-dimethylaminopropyl)carbodiimide hydrochloride, 2-(7-aza-1H-benzotriazol-1-yl)-1,1,3,3-tetramethyluronium hexafluorophosphate, 0-(benzotriazol-1-yl)-N,N,N',N'-tetramethyluronium hexafluorophosphate, 1H-benzotriazol-1-yloxytripyrrolidinophosphonium hexafluorophosphate, and the like, and preferably include ethyl chloroformate or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (Iab).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include dichloromethane, chloroform, or aprotic polar solvents such as N,N-dimethylformamide, N,N-dimethylacetamide, N-methyl-2-pyrrolidone, or dimethyl sulfoxide.

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (Iab) for use in the condensation reaction is preferably 1 mmol/L to 1 mol/L at the start of the reaction.

Among urea derivatives (Ia) as described above, a derivative (Iab) in which $R^4$ has carboxylic acid can be obtained, for example, by hydrolysis reaction of an alkyl ester derivative (Iac) in the presence of a base, as shown in Scheme 17.

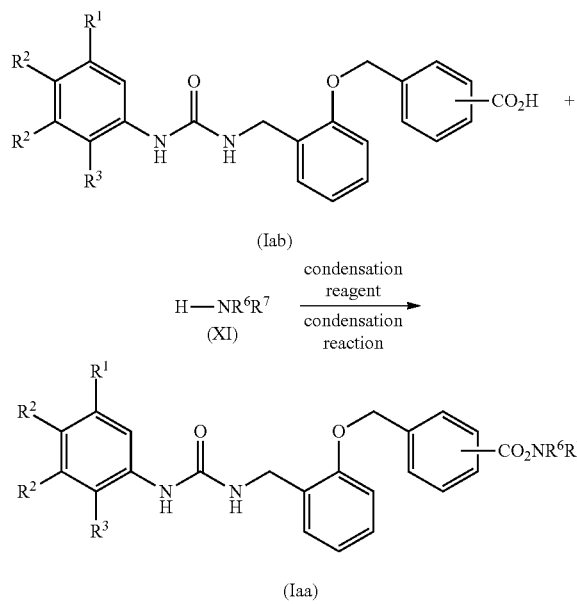

(wherein each symbol is as defined above.)

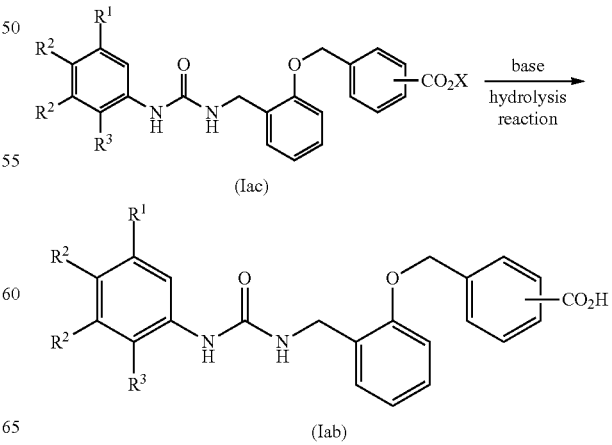

(wherein each symbol is as defined above.)

Examples of the base for use in the hydrolysis reaction include inorganic bases such as lithium hydroxide, sodium hydroxide, potassium hydroxide, barium hydroxide, or potassium carbonate.

The amount of the base for use in the hydrolysis reaction is preferably 0.5 to 20 equivalents, more preferably 1 to 3 equivalents, to the ester derivative (Iac).

A reaction solvent for use in the hydrolysis reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, N-methyl-2-pyrrolidone, or dimethyl sulfoxide; or ether-based solvents such as diethyl ether, tetrahydrofuran, dimethoxyethane, or 1,4-dioxane.

The reaction temperature of the hydrolysis reaction is preferably −20° C. to 200° C., more preferably 0-150° C.

The reaction time of the hydrolysis reaction is appropriately selected depending on the conditions such as reaction temperature, and is preferably 1 to 30 hours.

The concentration of the ester derivative (Iac) for use in the hydrolysis reaction is preferably 1 mmol/L to 1 mol/L at the start of the reaction.

Among urea derivatives (Ib) as described above, a derivative (Ibb) in which $R^4$ represents a pyrimidinyl group having a substituent in the 2-position can be obtained, for example, by nucleophilic substitution reaction of a 2-chloropyrimidine derivative (Iba) with a nucleophile (XIX), as shown in Scheme 18.

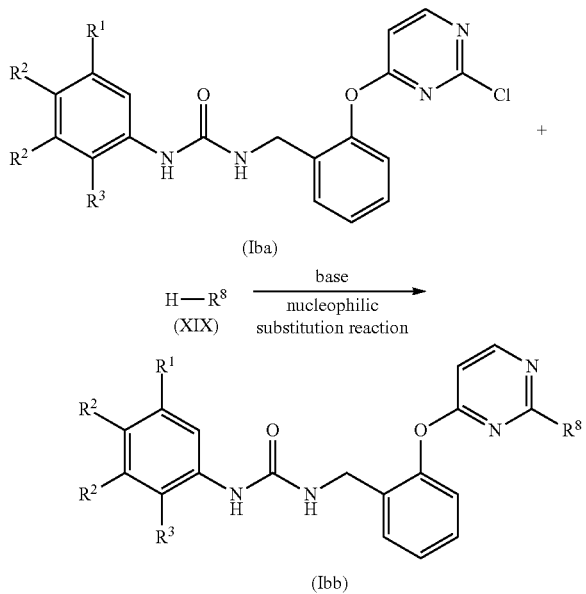

Scheme 18

(wherein $R^8$ represents 1H-imidazolyl, and other symbols are as defined above.)

The amount of the nucleophile (XIX) for use in the nucleophilic substitution reaction is preferably 0.2 to 10 equivalents, more preferably 0.5 to 3 equivalents, to the 2-chloropyrimidine derivative (Iba).

The nucleophilic substitution reaction may optionally be performed with a base. Examples of the base to be used include inorganic bases such as sodium hydride, sodium hydrogen carbonate, cesium carbonate, or potassium carbonate; organic bases such as triethylamine, diisopropylethylamine, or pyridine; or a mixture thereof.

The amount of the base for use in the nucleophilic substitution reaction is preferably 0.5 to 20 equivalents, more preferably 1 to 3 equivalents, to the 2-chloropyrimidine derivative (Iba).

A reaction solvent for use in the nucleophilic substitution reaction is appropriately selected depending on the type of reagents to be used, but it is not particularly limited as long as the reaction is not inhibited. Examples of the reaction solvent include alcohol-based solvents such as methanol or ethanol; nitrile-based solvents such as acetonitrile or propionitrile; aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; or mixed solvents thereof, and preferably include alcohol-based solvents such as methanol or ethanol; aprotic polar solvents such as N,N-dimethylformamide, N,N-dimethylacetamide, N-methyl-2-pyrrolidone, or dimethyl sulfoxide; or ether-based solvents such as diethyl ether, tetrahydrofuran, dimethoxyethane, or 1,4-dioxane.

The reaction temperature of the nucleophilic substitution reaction is preferably −20° C. to 200° C., more preferably 0-150° C.

The reaction time of the nucleophilic substitution reaction is appropriately selected depending on the conditions such as reaction temperature, and is preferably 1 to 30 hours.

The concentration of the 2-chloropyrimidine derivative (Iba) for use in the nucleophilic substitution reaction is preferably 1 mmol/L to 1 mol/L at the start of the reaction.

The DDR1 inhibitor is characterized by comprising, as an active ingredient, the urea derivative (I) or a pharmaceutically acceptable salt thereof.

The term "DDR1 inhibitor" means a compound that inhibits the kinase activity of DDR1.

The urea derivative (I) or a pharmaceutically acceptable salt thereof has DDR1 inhibition activity and is thus expected to be a therapeutic agent against diseases, for example, cancer, with which improvement of the clinical state or amelioration of symptoms of the diseases is expected based on the corresponding mechanism of action.

Examples of "cancer" include pharynx cancer, larynx cancer, tongue cancer, non-small cell lung cancer, breast cancer, esophagus cancer, gastric cancer, colorectal cancer, uterine cancer, endometrial cancer, ovarian cancer, liver cancer, pancreatic cancer, gallbladder cancer, bile duct cancer, kidney cancer, renal pelvis and ureter cancer, bladder cancer, prostate cancer, malignant melanoma, thyroid cancer, neurogenic or osteogenic sarcoma, chondrosarcoma, rhabdomyosarcoma, angiosarcoma, fibrosarcoma, glioma, leukemia, malignant lymphoma, neuroblastoma, myeloma, or brain tumor.

The DDR1 inhibition activity of the urea derivative (I) or a pharmaceutically acceptable salt thereof can be evaluated with an in vitro study. Examples of the in vitro study include a method in which the kinase activity of DDR1 is evaluated based on measuring the amount of a phosphorylated substrate or consumed ATP (Analytical Biochemistry, 1999, vol. 269: p. 94-104), and a method in which the binding of an assay target to DDR1 is measured (Journal of Biomolecular Screening, 2009, vol. 14: p. 924-935). More specific examples of a method for the evaluation of DDR1 kinase activity include a method in which a purified intracellular domain protein of DDR1, a substrate peptide, and ATP are mixed and allowed to react and the amount of the phosphorylated substrate peptide is measured. The amount of the phosphorylated substrate peptide can be measured, for example, by measurement of fluorescence resonance energy transfer using the substrate peptide labeled in advance with biotin or a fluorescent substance.

EXAMPLES

Our derivatives, compounds and methods will be described in more details below by way of Examples and Reference Examples. However, this disclosure is not limited thereto.

For any compounds whose synthetic methods are not described in the context of the synthesis of the compounds of Examples, commercially available compounds were used. The names of solvents indicated in the NMR data represent the solvents used for the measurements. Moreover, 400 MHz NMR spectrum was measured using the JNM-AL400 nuclear magnetic resonance spectrometer (JEOL Ltd.) or the JNM-ECS400 nuclear magnetic resonance spectrometer (JEOL Ltd.). Chemical shifts were referenced to tetramethylsilane and expressed in δ (unit: ppm), while the multiplicity of each signal was expressed as s (singlet), d (doublet), t (triplet), q (quartet), m (multiplet), br (broad), dd (double-doublet), dt (double-triplet), ddd (double-double-doublet), dq (double-quartet), or tt (triple-triplet). ESI-MS spectrum was measured using the Agilent Technologies 1200 Series, G6130A (manufactured by Agilent Technology). All the used solvents were commercially available. The YFLC W-prep 2×H chromatograph (Yamazen Science, Inc.) was used for flash chromatography. Whenever the term "aminosilica gel" is used, it refers to the use of aminopropylsilane-bonded silica gel. The Monowave 300 manufactured by Anton Paar GmbH was used as a microwave synthesis reactor.

Raw materials and intermediates of urea derivatives (I) were synthesized by methods described in Reference Examples below. For any compounds whose synthetic methods are not described in the context of the synthesis of the compounds of Reference Examples, commercially available compounds were used.

Reference Example 1

Synthesis of 1-(2-hydroxybenzyl)-3-(2-methoxy-5-(pentafluorosulfanyl)phenyl)urea

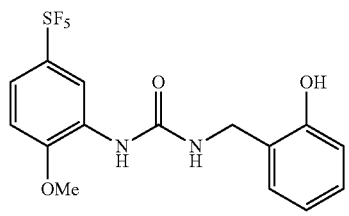

To a solution of 2-methoxy-5-(pentafluorosulfanyl)aniline (7.44 g, 29.9 mmol) in dichloromethane (30 mL), triphosgene (2.96 g, 9.95 mmol) and triethylamine (0.42 mL, 0.47 mmol) were added under cooling on ice, and the obtained solution was stirred for one hour. Then, 2-hydroxybenzylamine (3.61 g, 29.6 mmol) and triethylamine (2.99 g, 29.6 mmol) were added to the solution. After stirring the obtained solution at room temperature for 16 hours, a saturated aqueous solution of ammonium chloride was added to the reaction mixture, and the obtained solution was extracted with dichloromethane. The organic layer was dried over anhydrous sodium sulfate and concentrated, and the obtained crude product was purified by silica gel column chromatography (chloroform:methanol=10:1, Rf=0.42) to obtain the title compound (11.6 g, 97%) (hereinafter referred to as the compound of Reference Example 1) as a pale yellow solid.

MS(ESI) [M+H]$^+$: 399.

Example 1

Synthesis of 1-(2-methoxy-5-((pentafluorosulfanyl)phenyl)-3-(2-(pyridin-4-ylmethoxy)benzyl)urea

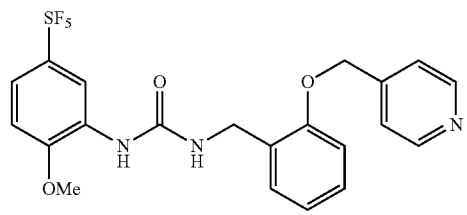

A solution of the compound of Reference Example 1 (2.0 g, 5.0 mmol), 4-(bromomethyl)pyridine hydrobromide (1.52 g, 6.0 mmol) and cesium carbonate (4.1 g, 13 mmol) in N,N-dimethylformamide (10 mL) was stirred overnight at room temperature, and water was subsequently added to the reaction solution, and the obtained solution was extracted with diethyl ether. The organic layer was washed with saturated brine, dried over anhydrous sodium sulfate, and then concentrated under vacuum. The obtained crude product was purified by silica gel column chromatography (ethyl acetate, Rf=0.32) to obtain a compound of interest (140 mg, 5.6%) (hereinafter referred to as the compound of Example 1) as a white solid.

$^1$H-NMR (400 MHz, CDCl$_3$) δ (ppm): 3.87 (3H, s), 4.58 (2H, d, J=4.0 Hz), 5.16 (2H, s), 6.81 (2H, m), 6.88 (1H, d, J=8.0 Hz), 7.00 (1H, t, J=8.0 Hz), 7.35-7.40 (4H, m), 8.62 (1H, dd, J=8.0, 4.0 Hz), 8.69 (1H, d, J=4.0 Hz).

MS(ESI) [M+H]$^+$: 490.

Reference Example 2

Synthesis of 4-(pentafluorosulfanyl)anisole

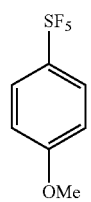

To a solution of 4-(pentafluorosulfanyl)nitrobenzene (20 g, 80 mmol) in N,N-dimethylformamide (100 mL), sodium methoxide (13 g, 240 mmol) was added. After stirring the obtained solution at room temperature for one hour, water was added to the reaction mixture, and the obtained solution was extracted with diethyl ether. The organic layer was dried over anhydrous sodium sulfate and concentrated, and the obtained crude product was purified by silica gel column chromatography (hexane, Rf=0.25) to obtain the title compound (16.3 g, 87%) (hereinafter referred to as the compound of Reference Example 2) as a colorless oily substance.

$^1$H-NMR (400 MHz, CDCl$_3$) δ (ppm): 3.85 (3H, s), 6.91 (2H, d, J=9.6 Hz), 7.68 (2H, d, J=9.6 Hz).

MS(ESI) [M+H]$^+$: 235.

Reference Example 3

Synthesis of 2-formyl-4-(pentafluorosulfanyl)anisole

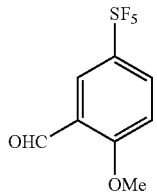

A solution of the compound of Reference Example 2 (1.25 g, 5.34 mmol) and dichloromethyl methyl ether (1.18 mL, 13.4 mmol) in dichloromethane (10 mL) was cooled to −20° C., and titanium tetrachloride (1.46 mL, 13.35 mmol) was added to the solution over 10 minutes to keep the temperature of the reaction solution within the range of −20 to −22° C. After stirring the obtained solution at a temperature within the same temperature range for 30 minutes, water was added to the reaction mixture, and the obtained solution was extracted with dichloromethane. The organic layer was dried over anhydrous sodium sulfate and concentrated, and the obtained crude product was purified by silica gel column chromatography (hexane:ethyl acetate=4:1, Rf=0.41) to obtain the title compound (521 mg, 37%) (hereinafter referred to as the compound of Reference Example 3) as a colorless solid.

$^1$H-NMR (400 MHz, CDCl$_3$) δ (ppm): 4.02 (3H, s), 7.04-7.08 (1H, m), 7.90-7.95 (1H, m), 8.22-8.24 (1H, m), 10.5 (1H, s).

MS(ESI) [M+H]$^+$: 263.

Reference Example 4

Synthesis of 3-formyl-2-methoxy-5-(pentafluorosulfanyl)nitrobenzene

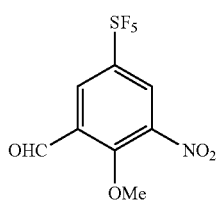

To a suspension of the compound of Reference Example 3 (5 g, 19.3 mmol) in concentrated sulfuric acid (60 mL), fuming nitric acid (1.0 mL) was added under cooling on ice. After stirring the obtained solution at the same temperature for three hours, ice was added to the reaction mixture, and the obtained solution was extracted with chloroform. The organic layer was dried and concentrated to obtain the title compound (5.28 g, 89%) (hereinafter referred to as the compound of Reference Example 4) as a yellow oily substance.

$^1$H-NMR (400 MHz, CDCl$_3$) δ (ppm): 4.15 (3H, s), 8.43-8.47 (2H, m), 10.4 (1H, s).

MS(ESI) [M+H]$^+$: 308.

Reference Example 5

Synthesis of 3-hydroxymethyl-2-methoxy-5-(pentafluorosulfanyl)nitrobenzene

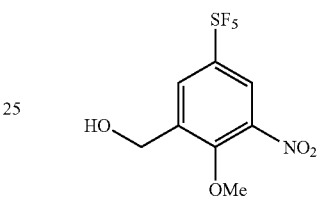

To a solution of the compound of Reference Example 4 (70.0 mg, 0.228 mmol) in methanol (2 mL), sodium borohydride (10.4 mg, 0.273 mmol) was added under cooling on ice. After stirring the obtained solution at the same temperature for one hour, 1.0 N hydrochloric acid was added to the reaction mixture, and the obtained solution was extracted with chloroform. The organic layer was washed with saturated brine, and subsequently dried over anhydrous sodium sulfate and concentrated, and the obtained crude product was purified by silica gel column chromatography (hexane:ethyl acetate=3:1, Rf=0.23) to obtain the title compound (67 mg, 95%) (hereinafter referred to as the compound of Reference Example 5) as a colorless solid.

$^1$H-NMR (400 MHz, CDCl$_3$) δ (ppm): 3.97 (3H, s), 4.82-4.87 (2H, m), 8.12-8.21 (2H, m).

MS(ESI) [M+H]$^+$: 310.

Reference Example 6

Synthesis of 3-hydroxymethyl-2-methoxy-5-(pentafluorosulfanyl)aniline

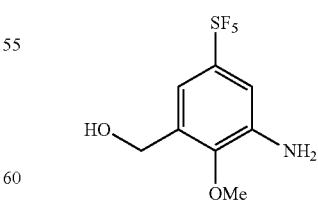

To a solution of the compound of Reference Example 5 (57.0 mg, 0.184 mmol) in methanol (1.0 mL), platinum oxide (4.20 mg, 0.0184 mmol) was added. After stirring the obtained solution for 30 minutes under hydrogen atmosphere, the obtained solution was filtrated to remove the catalyst and then concentrated, and the obtained crude product was purified by silica gel column chromatography (hexane:ethyl acetate=2:1, Rf=0.31) to obtain the title compound (49 mg, 95%) (hereinafter referred to as the compound of Reference Example 6) as a colorless solid.

$^1$H-NMR (400 MHz, CDCl$_3$) δ (ppm): 3.82 (3H, s), 3.94-4.02 (2H, m), 4.71-4.74 (2H, m), 7.08-7.12 (1H, m), 7.16-7.20 (1H, m).

MS(ESI) [M+H]$^+$: 280.

Reference Example 7

Synthesis of 2,2,2-trichloroethyl (3-hydroxymethyl-2-methoxy-5-(pentafluorosulfanyl)phenyl)carbamate

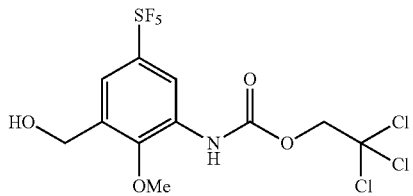

To the compound of Reference Example 6 (49 mg, 0.18 mmol) in tetrahydrofuran (5.0 mL), 2,2,2-trichloroethyl chloroformate (0.02 mL, 0.21 mmol) and diisopropylethylamine (0.04 mL, 0.21 mmol) were added under cooling on ice. After stirring the obtained solution at room temperature for three hours, water was added to the reaction mixture, and the obtained solution was extracted with ethyl acetate. The organic layer was washed with saturated brine, and subsequently dried over anhydrous sodium sulfate and concentrated, and the obtained crude product was purified by silica gel column chromatography (hexane:ethyl acetate=4:1, Rf=0.38) to obtain the title compound (71 mg, 87%) (hereinafter referred to as the compound of Reference Example 7) as a colorless solid.

$^1$H-NMR (400 MHz, CDCl$_3$) δ (ppm): 3.88 (3H, s), 4.77-4.88 (4H, m), 7.37-7.47 (1H, m), 7.59-7.62 (1H, m), 8.46-8.58 (1H, m).

MS(ESI) [M+H]$^+$: 455.

Reference Example 8

Synthesis of 1-(2-hydroxybenzyl)-3-(3-(hydroxymethyl)-2-methoxy-5-(pentafluorosulfanyl)phenyl)urea

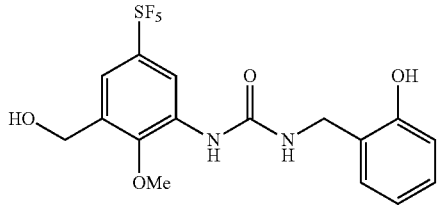

The title compound (73.3 mg) (hereinafter referred to as the compound of Reference Example 8) was obtained as a colorless amorphous material from the compound of Reference Example 6 (200 mg) according to a method similar to that described in Reference Example 1 (chloroform:methanol=10:1, Rf=0.45).

$^1$H-NMR (400 MHz, CDCl$_3$) δ (ppm): 3.78 (3H, s), 4.41 (2H, d, J=8.0 Hz), 4.75 (2H, d, J=4.0 Hz), 5.47 (1H, m), 6.83-6.87 (2H, m), 6.96 (1H, d, J=8.0 Hz), 7.10 (1H, dd, J=8.0, 4.0 Hz), 7.53 (1H, d, J=4.0 Hz), 8.50 (1H, d, J=4.0 Hz), 8.93 (1H, brs).

MS(ESI) [M+H]$^+$: 429.

Example 2

Synthesis of 1-(3-(hydroxymethyl)-2-methoxy-5-((pentafluorosulfanyl)phenyl)-3-(2-(pyridin-4-yl-methoxy) benzyl)urea

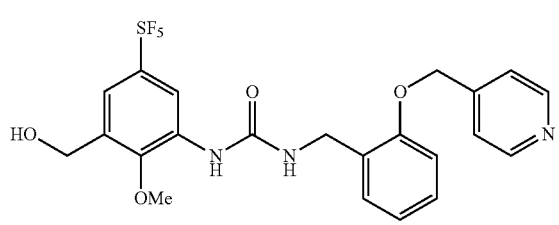

The title compound (10 mg) (hereinafter referred to as the compound of Example 2) was obtained as a white oily substance from the compound of Reference Example 8 (73 mg) according to a method similar to that described in Example 1 (chloroform:methanol=10:1, Rf=0.42).

$^1$H-NMR (400 MHz, CDCl$_3$) δ (ppm): 3.62 (3H, s), 4.56 (2H, d, J=4.0 Hz), 4.68 (2H, s), 5.10 (2H, s), 5.63 (1H, t, J=8.0 Hz), 6.89 (2H, d, J=8.0 Hz), 6.99 (1H, t, J=8.0 Hz), 7.08 (1H, s), 7.38 (1H, d, J=4.0 Hz), 7.45 (1H, m), 8.52 (1H, d, J=4.0 Hz), 8.56 (1H, m).

MS(ESI) [M+H]$^+$: 520.

Reference Example 9

Synthesis of 2,2,2-trichloroethyl (2-methoxy-5-(trifluoromethoxy)phenyl)carbamate

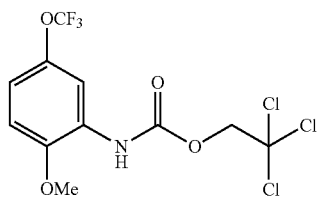 [SMILES: COc1ccc(OC(F)(F)F)cc1NC(=O)OCC(Cl)(Cl)Cl]

The title compound (4.0 g) (hereinafter referred to as the compound of Reference Example 9) was obtained from 2-methoxy-5-(trifluoromethoxy)aniline (3.0 g) according to a method similar to that described in Reference Example 7 (hexane:ethyl acetate=1:1, Rf=0.31). MS(ESI) [M+H]$^+$: 383.

Reference Example 10

Synthesis of 1-(2-hydroxybenzyl)-3-(2-methoxy-5-(trifluoromethoxy)phenyl)urea

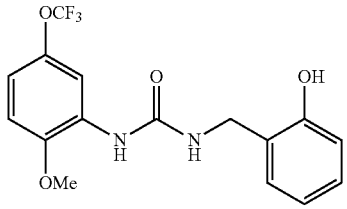

The title compound (427 mg) (hereinafter referred to as the compound of Reference Example 10) was obtained as a colorless amorphous material from 2-methoxy-5-(trifluoromethoxy)aniline (500 mg) according to a method similar to that described in Reference Example 1 (hexane:ethyl acetate=1:1, Rf=0.33).

MS(ESI) [M+H]$^+$: 357.

Example 3

Synthesis of 1-(2-methoxy-5-(trifluoromethoxy)phenyl)-3-(3-pyridin-ylmethoxy)benzyl)urea

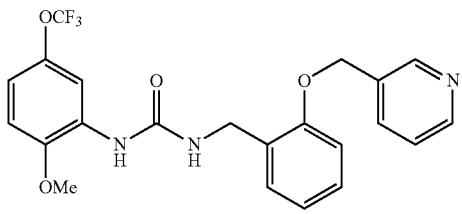 [SMILES: COc1ccc(OC(F)(F)F)cc1NC(=O)NCc1ccccc1OCc1cccnc1]

The title compound (55 mg) (hereinafter referred to as the compound of Example 3) was obtained as a white solid from the compound of Reference Example 10 (100 mg) and 3-(bromomethyl)pyridine hydrobromide (106 mg) according to a method similar to that described in Example 1 (hexane:ethyl acetate=1:4, Rf=0.28).

$^1$H-NMR (CDCl$_3$, 400 MHz) δ: 3.76 (3H, s), 4.50 (2H, d, J=4.0 Hz), 5.10 (2H, s), 5.29 (1H, t, J=4.0 Hz), 6.72-6.79 (2H, m), 6.93-6.99 (3H, m), 7.25-7.32 (2H, m), 7.37 (1H, dd, J=8.0, 4.0 Hz), 7.78 (1H, d, J=8.0 Hz), 8.15 (1H, d, J=4.0 Hz), 8.56 (1H, d, J=4.0 Hz), 8.64 (1H, s).

MS(ESI) [M+H]$^+$: 448.

Example 4

Synthesis of 1-(2-methoxy-5-(trifluoromethoxy)phenyl)-3-(4-pyridin-ylmethoxy)benzyl)urea The title compound (48 mg) (hereinafter referred to as the compound of Example 4) was obtained as a white solid from the compound of Reference Example 10 (100 mg) and 4-(chloromethyl)pyridine hydrobromide (106 mg) according to a method similar to that described in Example 1 (hexane:ethyl acetate=1:4, Rf=0.24).

$^1$H-NMR (CDCl$_3$, 400 MHz) δ: 3.77 (3H, s), 4.57 (2H, d, J=4.0 Hz), 5.13 (2H, s), 5.36 (1H, t, J=4.0 Hz), 6.73-6.80 (2H, m), 6.87 (1H, d, J=8.0 Hz), 6.97 (1H, t, J=8.0 Hz), 7.03 (1H, br), 7.25 (1H, td, J=8.0, 4.0 Hz), 7.32 (2H, dd, J=8.0, 4.0 Hz), 7.40 (1H, dd, J=8.0, 4.0 Hz), 8.17 (1H, d, J=4.0 Hz), 8.58 (2H, dd, J=8.0, 4.0 Hz).

MS(ESI) [M+H]$^+$: 448.

Reference Example 11

Synthesis of ethyl 4-((2-((3-(2-methoxy-5-(trifluoromethoxy)phenyl)ureido)methyl)phenoxy)methyl)picolinate The title compound (40 mg) (hereinafter referred to as the compound of Reference Example 11) was obtained as a white solid from the compound of Reference Example 10 (67 mg) and ethyl 4-(chloromethyl)picolinate hydrochloride (30 mg) according to a method similar to that described in Example 1 (hexane:ethyl acetate=1:1, Rf=0.32).

MS(ESI) [M+H]$^+$: 520.

Example 5

Synthesis of 4-((2-((3-(2-methoxy-5-(trifluoromethoxy)phenyl)ureido)methyl)phenoxy)methyl)picolinamide To a solution of the compound of Reference Example 11 (30 mg, 0.06 mmol) in tetrahydrofuran/methanol, a 1.0 N aqueous solution of sodium hydroxide was added, and the obtained solution was stirred overnight at room temperature. The reaction mixture was adjusted to pH 5 or below by adding 1.0 N hydrochloric acid and then extracted with ethyl acetate. The ethyl acetate solution was washed with saturated brine, dried over anhydrous sodium sulfate, and then concentrated under vacuum. To a solution of the obtained crude product and 2-(7-aza-1H-benzotriazol-1-yl)-1,1,3,3-tetramethyluronium hexafluorophosphate (10 mg) in N,N- dimethylformamide, triethylamine (5.2 mg) was added, and the obtained solution was stirred at room temperature for 30 minutes. An excess amount of ammonium water was added to the solution, and successively the obtained solution was stirred for 30 minutes. A 1.0 N hydrochloric acid solution was added to the reaction solution and the obtained solution was extracted with ethyl acetate. The organic layer was dried over anhydrous sodium sulfate and then concentrated under vacuum. The obtained crude product was purified by silica gel column chromatography (chloroform:methanol=10:1, Rf=0.29) to obtain a compound of interest (10 mg, 35%) (hereinafter referred to as the compound of Example 5) as a white solid.

$^1$H-NMR (DMSO-d$_6$, 400 MHz) δ: 3.86 (3H, s), 4.50 (2H, d, J=4.0 Hz), 5.30 (2H, s), 6.79 (1H, d, J=8.0 Hz), 6.92-7.00 (3H, m), 7.24 (1H, t, J=8.0 Hz), 7.33 (1H, d, J=8.0 Hz), 7.69 (1H, d, J=4.0 Hz), 8.09 (1H, m), 8.18 (1H, s), 8.57 (1H, d, J=8.0 Hz).

MS(ESI) [M+H]$^+$: 491.

Reference Example 12

Synthesis of 1-(2-hydroxybenzyl)-3-(2-methoxy-5-(trifluoromethyl)phenyl)urea

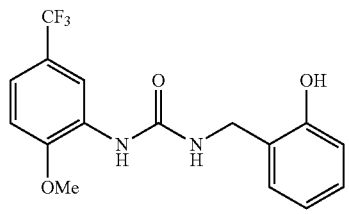 [SMILES: COc1ccc(C(F)(F)F)cc1NC(=O)NCc1ccccc1O]

The title compound (50 mg) (hereinafter referred to as the compound of Reference Example 12) was obtained as a colorless foam from 2-methoxy-5-trifluoromethylaniline (310 mg) according to a method similar to that described in Reference Example 1 (hexane:ethyl acetate=1:1, Rf=0.30).

MS(ESI) [M+H]$^+$: 341.

Example 6

Synthesis of 1-(2-methoxy-5-(trifluoromethyl)phenyl)-3-(3-pyridin-ylmethoxy)benzyl)urea

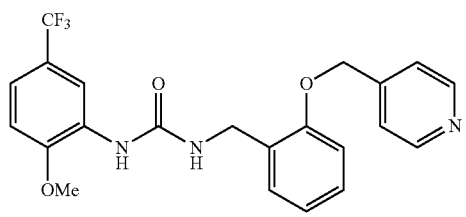 [SMILES: COc1ccc(C(F)(F)F)cc1NC(=O)NCc1ccccc1OCc1ccncc1]

The title compound (55 mg) (hereinafter referred to as the compound of Example 6) was obtained as a white solid from the compound of Reference Example 12 (100 mg) and 3-(bromomethyl)pyridine hydrobromide (106 mg) according to a method similar to that described in Example 1 (hexane:ethyl acetate=1:4, Rf=0.28).

$^1$H-NMR (DMSO-d$_6$, 400 MHz) δ: 3.34 (3H, s), 4.34 (2H, d, J=4.0 Hz), 4.58-4.71 (2H, m), 4.96 (1H, t, J=4.0 Hz), 5.38-5.44 (1H, m), 6.76 (1H, d, J=8.0 Hz), 6.93 (1H, d, J=8.0 Hz), 7.12-7.24 (3H, m), 7.32 (1H, dd, J=8.0, 4.0 Hz), 7.40-7.51 (5H, m), 7.63 (1H, d, J=8.0 Hz), 8.01 (1H, s), 8.29 (1H, s), 8.54 (1H, d, J=2.0 Hz).

MS(ESI) [M+H]$^+$: 432.

Example 7

Synthesis of methyl 4-((2-((3-(2-methoxy-5-(trifluoromethoxy)phenyl)ureido)methyl)phenoxy)methyl)benzoate

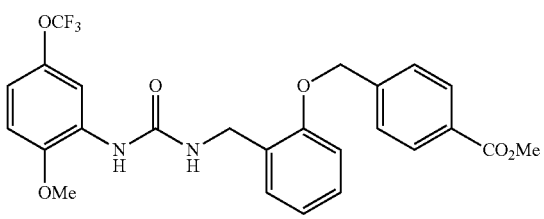 [SMILES: COC(=O)c1ccc(COc2ccccc2CNC(=O)Nc2cc(OC(F)(F)F)ccc2OC)cc1]

The title compound (72 mg) (hereinafter referred to as the compound of Example 7) was obtained as a white solid from the compound of Reference Example 10 (100 mg) and methyl 4-(bromomethyl)benzoate (70.7 mg) according to a method similar to that described in Example 1 (hexane:ethyl acetate=1:1, Rf=0.61).

$^1$H-NMR (CDCl$_3$, 400 MHz) δ: 3.82 (3H, s), 3.92 (3H, s), 4.53 (2H, d, J=8.0 Hz), 5.08 (1H, t, J=4.0 Hz), 5.19 (2H, s), 6.74-6.99 (3H, m), 6.92 (1H, d, J=8.0 Hz), 6.97 (1H, t, J=8.0 Hz), 7.37 (1H, d, J=8.0 Hz), 7.50 (2H, d, J=8.0 Hz), 8.05 (2H, d, J=8.0 Hz), 8.14 (1H, s).

MS(ESI) [M+H]$^+$: 505.

Example 8

Synthesis of 4-((2-((3-(2-methoxy-5-(trifluoromethoxy)phenyl)ureido)methyl)phenoxy)methyl)benzoic acid

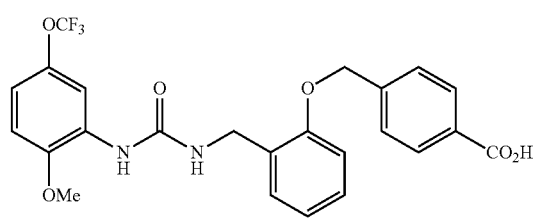 [SMILES: COc1ccc(OC(F)(F)F)cc1NC(=O)NCc1ccccc1OCc1ccc(C(=O)O)cc1]

To a solution of the compound of Example 7 (60 mg, 0.12 mmol) in tetrahydrofuran/methanol, a 1.0 N aqueous solution of sodium hydroxide was added, and the obtained solution was stirred overnight at room temperature. The reaction mixture was adjusted to pH 5 or below by adding 1.0 N hydrochloric acid and then extracted with ethyl acetate. The ethyl acetate solution was washed with saturated brine, dried over anhydrous sodium sulfate, and then concentrated under vacuum. The obtained crude product was purified by silica gel column chromatography (chloroform:methanol=10:1, Rf=0.48) to obtain the title compound (18 mg, 31%) (hereinafter referred to as the compound of Example 8) as a white solid.

¹H-NMR (DMSO-d₆, 400 MHz) δ: 3.86 (3H, s), 4.36 (2H, d, J=8.0 Hz), 5.27 (2H, s), 6.84 (1H, dd, J=8.0, 4.0 Hz), 6.94 (1H, t, J=4.0 Hz), 7.02-7.07 (2H, m), 7.22-7.28 (2H, m), 7.34 (1H, t, J=8.0 Hz), 7.94 (2H, d, J=8.0 Hz), 8.21 (1H, s), 8.35 (1H, s).

MS(ESI) [M+H]⁺: 491.

Reference Example 13

Synthesis of methyl 3-((2-((3-(2-methoxy-5-(trifluoromethoxy)phenyl)ureido)methyl)phenoxy)methyl)benzoate

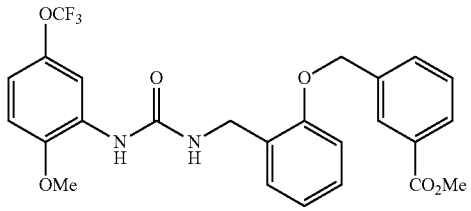 [SMILES: COC(=O)c1cccc(COc2ccccc2CNC(=O)Nc2cc(OC(F)(F)F)ccc2OC)c1]

The title compound (92 mg) (hereinafter referred to as the compound of Reference Example 13) was obtained as a white solid from the compound of Reference Example 10 (100 mg) and methyl 3-(bromomethyl)benzoate (70.7 mg) according to a method similar to that described in Example 1 (hexane:ethyl acetate=1:1, Rf=0.58).

¹H-NMR (CDCl₃, 400 MHz) δ: 3.80 (3H, s), 3.91 (3H, s), 4.52 (2H, d, J=8.0 Hz), 5.13 (1H, t, J=4.0 Hz), 5.18 (2H, s), 6.73-6.79 (2H, m), 6.87 (1H, br), 6.93-6.99 (2H, m), 7.38 (1H, dd, J=8.0, 4.0 Hz), 7.47 (1H, t, J=8.0 Hz), 7.64 (2H, d, J=8.0 Hz), 8.00 (2H, d, J=8.0 Hz), 8.11 (1H, s), 8.15 (1H, s).

MS(ESI) [M+H]⁺: 505.

Example 9

Synthesis of 3-((2-((3-(2-methoxy-5-(trifluoromethoxy)phenyl)ureido)methyl)phenoxy)methyl)benzoic acid

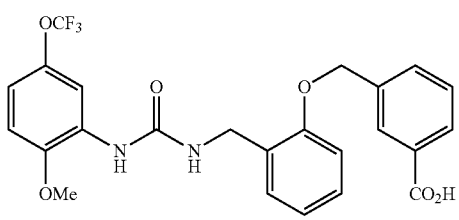 [SMILES: COc1ccc(OC(F)(F)F)cc1NC(=O)NCc1ccccc1OCc1cccc(C(=O)O)c1]

The title compound (62 mg) (hereinafter referred to as the compound of Example 9) was obtained as a white solid from the compound of Reference Example 13 (92 mg) according to a method similar to that described in Example 8 (chloroform:methanol=10:1, Rf=0.45).

¹H-NMR (DMSO-d₆, 400 MHz) δ: 3.86 (3H, s), 4.34 (2H, d, J=4.0 Hz), 5.26 (2H, s), 6.84 (1H, d, J=8.0 Hz), 6.95 (1H, t, J=8.0 Hz), 7.02 (1H, d, J=12.0 Hz), 7.08 (1H, d, J=8.0 Hz), 7.22-7.27 (3H, m), 7.36 (1H, br), 7.48-7.52 (1H, m), 7.74 (1H, br), 7.89 (1H, d, J=8.0 Hz), 8.06 (1H, s), 8.19 (1H, d, J=4.0 Hz), 8.36 (1H, s).

MS(ESI) [M+H]⁺: 491.

Reference Example 14

Synthesis of 2-methoxy-3-nitro-5-(trifluoromethyl)benzaldehyde

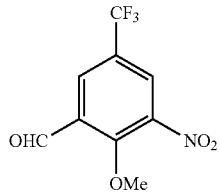 [SMILES: COc1c(C=O)cc(C(F)(F)F)cc1[N+](=O)[O-]]

The title compound (3.2 g) (hereinafter referred to as the compound of Reference Example 14) was obtained from 2-methoxy-5-(trifluoromethyl)benzaldehyde (3.0 g) according to a method similar to that described in Reference Example 4.

¹H-NMR (400 MHz, CDCl₃) δ (ppm): 4.15 (3H, s), 8.33 (2H, d, J=2.2 Hz), 8.35 (2H, d, J=2.4 Hz), 10.43 (1H, s).

Reference Example 15

Synthesis of (2-methoxy-3-nitro-5-(trifluoromethyl)phenyl)methanol

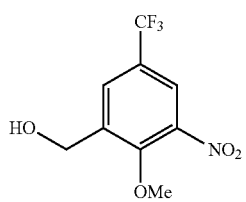 [SMILES: COc1c(CO)cc(C(F)(F)F)cc1[N+](=O)[O-]]

The title compound (1.9 g) (hereinafter referred to as the compound of Reference Example 15) was obtained from the compound of Reference Example 14 (2.0 g) according to a method similar to that described in Reference Example 5 (hexane:ethyl acetate=3:1, Rf=0.28).

¹H-NMR (400 MHz, CDCl₃) δ (ppm): 2.01 (1H, t, J=5.9 Hz), 3.98 (3H, s), 4.87 (2H, d, J=5.9 Hz), 8.01 (1H, d, J=1.8 Hz), 8.06 (1H, d, J=1.8 Hz).

Reference Example 16

Synthesis of (3-amino-2-methoxy-5-(trifluoromethyl)phenyl)methanol

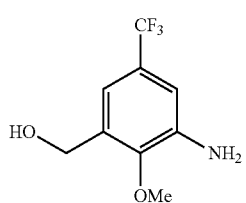

The title compound (0.84 g) (hereinafter referred to as the compound of Reference Example 16) was obtained from the compound of Reference Example 15 (1.0 g) according to a method similar to that described in Reference Example 6 (hexane:ethyl acetate=2:1, Rf=0.32).

$^1$H-NMR (400 MHz, CDCl$_3$) δ (ppm): 1.96 (1H, s), 3.83 (3H, s), 3.97 (2H, s), 4.74 (2H, s), 6.95 (1H, d, J=1.4 Hz), 7.04 (1H, s).

MS(ESI) [M+H]$^+$: 222.

Reference Example 17

Synthesis of 2,2,2-trichloroethyl (3-(hydroxymethyl)-2-methoxy-5-(trifluoromethyl)phenyl)carbamate

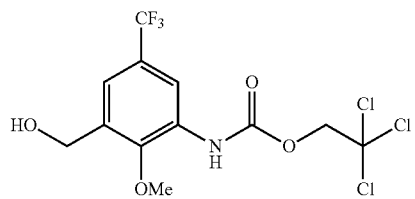 [SMILES: COc1c(CO)cc(C(F)(F)F)cc1NC(=O)OCC(Cl)(Cl)Cl]

The title compound (1.2 g) (hereinafter referred to as the compound of Reference Example 17) was obtained from the compound of Reference Example 16 (0.84 g) according to a method similar to that described in Reference Example 7 (hexane:ethyl acetate=2:1, Rf=0.43).

$^1$H-NMR (400 MHz, CDCl$_3$) δ (ppm): 1.90 (1H, t, J=6.1 Hz), 3.89 (3H, s), 4.80 (2H, d, J=5.9 Hz), 4.87 (2H, s), 7.43 (1H, s), 7.46 (1H, d, J=1.4 Hz), 8.37 (1H, s).

Example 10

Synthesis of methyl 4-((2-((3-(3-(hydroxymethyl)-2-methoxy-5-(trifluoromethyl)phenyl)ureido)methyl)phenoxy)methyl)benzoate

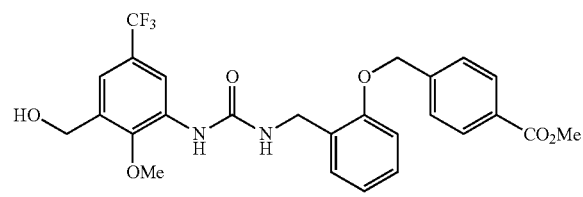 [SMILES: COC(=O)c1ccc(COc2ccccc2CNC(=O)Nc2cc(C(F)(F)F)cc(CO)c2OC)cc1]

A solution of the compound of Reference Example 17 (30 mg, 0.08 mmol), methyl 4-((2-(aminomethyl)phenoxy)methyl)benzoate hydrochloride (21 mg) and diisopropylethylamine (0.02 ml) in acetonitrile (10 mL) was stirred for 30 minutes at 150° C. by using the microwave reactor and then concentrated under vacuum. The obtained crude product was purified by silica gel column chromatography (hexane:ethyl acetate=1:2, Rf=0.71) to obtain the title compound (31 mg, 75%) (hereinafter referred to as the compound of Example 10) as a white solid.

$^1$H-NMR (DMSO-d$_6$, 400 MHz) δ: 3.70 (31H, s), 3.84 (3H, s), 4.39 (2H, d, J=4.0 Hz), 4.59 (211, d, J=4.0 Hz), 5.28 (2H, s), 5.35 (1H, t, J=4.0 Hz), 6.96 (1H, t, J=8.0 Hz), 7.07 (2H, d, J=8.0 Hz), 7.24-7.35 (4H, m), 7.64 (1H, d, J=8.0 Hz), 7.95 (2H, d, J=8.0 Hz), 8.43 (1H, s), 8.52 (1H, s).

MS(ESI) [M+H]$^+$: 519.

Example 11

Synthesis of 4-((2-((3-(3-(hydroxymethyl)-2-methoxy-5-(trifluoromethyl)phenyl)ureido)methyl)phenoxy)methyl)benzoic acid

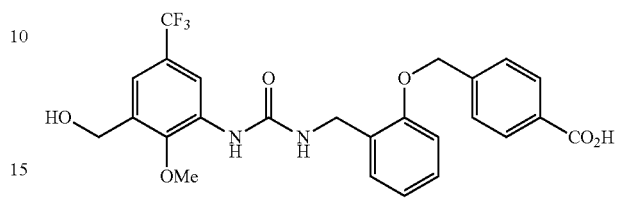

The title compound (17 mg) (hereinafter referred to as the compound of Example 11) was obtained as a white solid from the compound of Example 10 (20 mg) according to a method similar to that described in Example 8 (chloroform:methanol=10:1, Rf=0.41).

$^1$H-NMR (DMSO-d$_6$, 400 MHz) δ: 3.71 (3H, s), 4.38 (2H, d, J=4.0 Hz), 4.59 (2H, s), 5.28 (2H, s), 6.96 (1H, t, J=8.0 Hz), 7.07 (2H, d, J=8.0 Hz), 7.22-7.36 (4H, m), 7.60 (2H, d, J=8.0 Hz), 7.95 (2H, d, J=4.0 Hz), 8.45 (1H, s), 8.52 (1H, d).

MS(ESI) [M+H]$^+$: 505.

Example 12

Synthesis of 4-((2-((3-(2-methoxy-5-(trifluoromethoxy)phenyl)ureido)methyl)phenoxy)methyl)benzamide

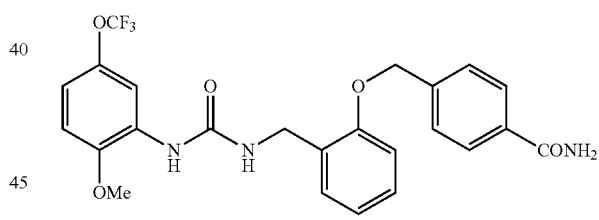

To a solution of the compound of Example 8 (20 mg, 0.04 mmol) and 2-(7-aza-1H-benzotriazol-1-yl)-1,1,3,3-tetramethyluronium hexafluorophosphate (23 mg, 0.06 mmol) in N,N-dimethylformamide, diisopropylethylamine (5.3 mg, 0.04 mmol) was added, and the obtained solution was stirred at room temperature for 30 minutes. An excess amount of ammonium water was added to the solution, and successively the obtained solution was stirred for 30 minutes. A 1.0 N hydrochloric acid solution was added to the reaction solution and the obtained solution was extracted with ethyl acetate. The organic layer was dried over anhydrous sodium sulfate and then concentrated under vacuum. The obtained crude product was purified by silica gel column chromatography (chloroform:methanol=10:1, Rf=0.42) to obtain the title compound (18 mg, 90%) (hereinafter referred to as the compound of Example 12) as a white solid.

$^1$H-NMR (DMSO-d$_6$, 400 MHz) δ: 3.86 (3H, s), 4.35 (2H, d, J=4.0 Hz), 5.24 (2H, s), 6.85 (1H, d, J=8.0 Hz), 6.94 (1H, t, J=8.0 Hz), 7.02-7.06 (2H, m), 7.22-7.27 (2H, m), 7.30-

7.40 (2H, m), 7.56 (2H, d, J=8.0 Hz), 7.88 (2H, d, J=8.0 Hz), 7.96 (1H, br), 8.21 (1H, d, J=4.0 Hz), 8.36 (1H, s).
MS(ESI) [M+H]⁺: 490.

Example 13

Synthesis of 4-((2-((3-(2-methoxy-5-(trifluoromethoxy)phenyl)ureido)methyl)phenoxy)methyl)-N-methylbenzamide

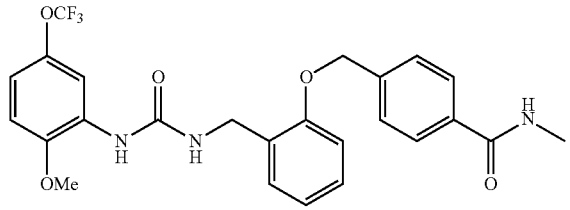 [SMILES: CNC(=O)c1ccc(COc2ccccc2CNC(=O)Nc2cc(OC(F)(F)F)ccc2OC)cc1]

To a solution of the compound of Example 8 (12 mg, 0.04 mmol) and 2-(7-aza-1H-benzotriazol-1-yl)-1,1,3,3-tetramethyluronium hexafluorophosphate (14 mg, 0.04 mmol) in N,N-dimethylformamide, triethylamine (5.2 mg, 0.04 mmol) was added, and the obtained solution was stirred at room temperature for 30 minutes. An excess amount of a 40% solution of dimethylamine in methanol was added to the solution, and successively the obtained solution was stirred for 30 minutes. Water and a 1.0 N hydrochloric acid solution were added to the reaction solution and the obtained solution was extracted with ethyl acetate. The organic layer was dried over anhydrous sodium sulfate and then concentrated under vacuum. The obtained crude product was purified by silica gel column chromatography (hexane:ethyl acetate=1:4, Rf=0.52) to obtain the title compound (7.2 mg, 58%) (hereinafter referred to as the compound of Example 13) as a white solid.
¹H-NMR (DMSO-d₆, 400 MHz) δ: 2.77 (3H, d, J=8.0 Hz), 3.86 (3H, s), 4.35 (2H, d, J=4.0 Hz), 5.24 (2H, s), 6.85 (1H, d, J=8.0 Hz), 6.94 (1H, t, J=8.0 Hz), 7.02-7.06 (2H, m), 7.22-7.27 (2H, m), 7.34 (1H, t, J=4.0 Hz), 7.57 (2H, d, J=8.0 Hz), 7.83 (2H, d, J=8.0 Hz), 8.21 (1H, d, J=4.0 Hz), 8.35 (1H, s), 8.40-8.50 (1H, m).
MS(ESI) [M+H]⁺: 504.

Example 14

Synthesis of 4-((2-((3-(2-methoxy-5-(trifluoromethoxy)phenyl)ureido)methyl)phenoxy)methyl)-N,N-dimethylbenzamide

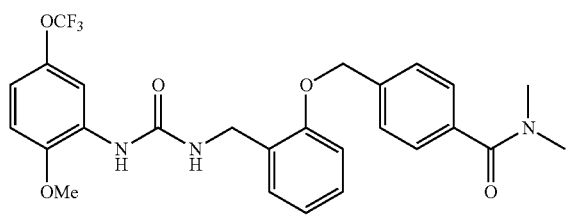 [SMILES: COc1ccc(OC(F)(F)F)cc1NC(=O)NCc1ccccc1OCc1ccc(C(=O)N(C)C)cc1]

The title compound (17 mg) (hereinafter referred to as the compound of Example 14) was obtained as a white solid from the compound of Example 8 (20 mg) according to a method similar to that described in Example 13 (chloroform:methanol=20:1, Rf=0.82).
¹H-NMR (MeOH-d₄, 400 MHz) δ: 2.80 (3H, d, J=8.0 Hz), 2.96 (3H, s), 3.08 (3H, s), 3.87 (3H, s), 4.44 (2H, s), 5.21 (2H, s), 6.80 (1H, d, J=8.0 Hz), 6.90-6.97 (2H, m), 7.02 (1H, d, J=8.0 Hz), 7.23 (1H, t, J=4.0 Hz), 7.30 (2H, d, J=8.0 Hz), 7.57 (2H, d, J=12.0 Hz), 8.11 (1H, d, J=4.0 Hz).
MS(ESI) [M+H]⁺: 518.

Example 15

Synthesis of N-(2-(diethylamino)ethyl)-4-((2-((3-(2-methoxy-5-(trifluoromethoxy)phenyl)ureido)methyl)phenoxy)methyl)benzamide

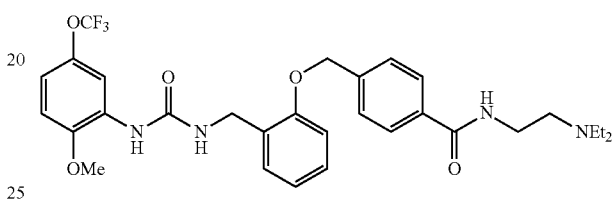

The title compound (17 mg) (hereinafter referred to as the compound of Example 15) was obtained as a foam from the compound of Example 8 (20 mg) according to a method similar to that described in Example 13 (amino-silica gel, chloroform:methanol=20:1, Rf=0.75).
¹H-NMR (MeOH-d₄, 400 MHz) δ: 0.99 (6H, t, J=8.0 Hz), 2.52-2.63 (6H, m), 3.39 (2H, t, J=8.0 Hz), 3.77 (3H, s), 4.36 (2H, s), 5.14 (2H, s), 6.70 (1H, dd, J=8.0, 4.0 Hz), 6.82-6.86 (2H, m), 6.91 (1H, d, J=8.0 Hz), 7.13 (1H, t, J=4.0 Hz), 7.21 (2H, dd, J=8.0, 4.0 Hz), 7.48 (2H, d, J=8.0 Hz), 7.71 (2H, d, J=8.0 Hz), 8.00 (1H, d, J=4.0 Hz).
MS(ESI) [M+H]⁺: 589.

Example 16

Synthesis of N-(2-(dimethylamino)ethyl)-4-((2-((3-(2-methoxy-5-(trifluoromethoxy)phenyl)ureido)methyl)phenoxy)methyl)benzamide

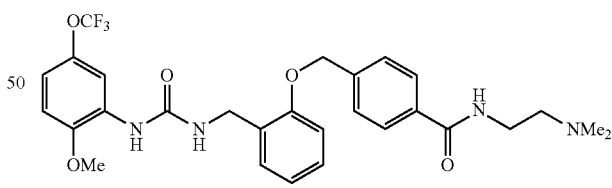

The title compound (17 mg) (hereinafter referred to as the compound of Example 16) was obtained as a foam from the compound of Example 8 (20 mg) according to a method similar to that described in Example 13 (amino-silica gel, chloroform:methanol=20:1, Rf=0.68).
¹H-NMR (MeOH-d₄, 400 MHz) δ: 2.31 (6H, s), 2.57 (2H, t, J=8.0 Hz), 3.51 (2H, t, J=8.0 Hz), 3.87 (3H, s), 4.45 (2H, s), 5.23 (2H, s), 6.78 (1H, dd, J=8.0, 4.0 Hz), 6.91-6.96 (2H, m), 7.01 (1H, d, J=8.0 Hz), 7.22 (1H, t, J=4.0 Hz), 7.30 (1H, dd, J=8.0, 4.0 Hz), 7.58 (2H, d, J=8.0 Hz), 7.82 (2H, d, J=8.0 Hz), 8.09 (1H, d, J=4.0 Hz).
MS(ESI) [M+H]⁺: 561.

Reference Example 18

Synthesis of tert-butyl (2-(4-((2-((3-(2-methoxy-5-(trifluoromethoxy)phenyl)ureido)methyl)phenoxy)methyl)benzamide)ethyl)(methyl)carbamate

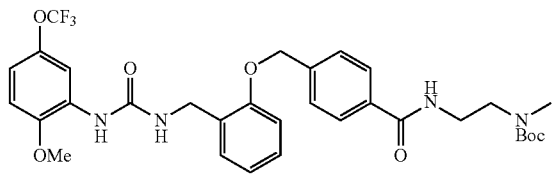 [SMILES: COc1ccc(OC(F)(F)F)cc1NC(=O)NCc1ccccc1OCc1ccc(C(=O)NCCN(C)C(=O)OC(C)(C)C)cc1]

The title compound (32 mg) (hereinafter referred to as the compound of Reference Example 18) was obtained as a foam from the compound of Example 8 (50 mg) according to a method similar to that described in Example 5 (chloroform:methanol=20:1, Rf=0.70). MS(ESI) [M+H]$^+$: 647.

Example 17

Synthesis of 4-((2-((3-(2-methoxy-5-(trifluoromethoxy)phenyl)ureido)methyl)phenoxy)methyl)-N-(2-(methylamino)ethyl)benzamide

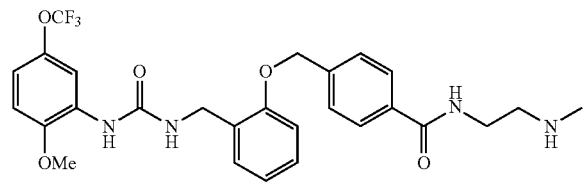 [SMILES: CNCCNC(=O)c1ccc(COc2ccccc2CNC(=O)Nc2cc(OC(F)(F)F)ccc2OC)cc1]

To a solution of the compound of Reference Example 18 (15 mg, 0.02 mmol) in methanol, a 4.0 N solution of hydrogen chloride in dioxane was added, and the obtained solution was left to stand at room temperature for one hour. The reaction mixture was concentrated, subsequently adjusted to basic conditions, and then extracted with chloroform-methanol mixture (chloroform:methanol=95:5, v/v). The organic layer was dried over anhydrous sodium sulfate and then concentrated under vacuum. The obtained crude product was purified by silica gel column chromatography (amino-silica gel, chloroform:methanol=10:1, Rf=0.52) to obtain the title compound (8.2 mg) (hereinafter referred to as the compound of Example 17) as an oily substance.

$^1$H-NMR (MeOH-d$_4$, 400 MHz) δ: 2.41 (3H, s), 2.78 (2H, br), 3.51 (2H, br), 3.87 (3H, s), 4.45 (2H, s), 5.23 (2H, s), 6.80 (1H, d, J=8.0 Hz), 6.91-6.96 (2H, m), 7.01 (1H, d, J=8.0 Hz), 7.22 (1H, t, J=4.0 Hz), 7.30 (1H, d, J=8.0 Hz), 7.58 (2H, d, J=8.0 Hz), 7.82 (2H, d, J=8.0 Hz), 8.09 (1H, d, J=4.0 Hz).

MS(ESI) [M+H]$^+$: 547.

Reference Example 19

Synthesis of 2,2,2-trichloroethyl (2-methoxy-5-(trifluoromethyl)phenyl)carbamate

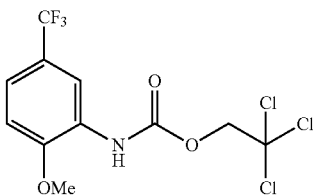 [SMILES: COc1ccc(C(F)(F)F)cc1NC(=O)OCC(Cl)(Cl)Cl]

The title compound (7.8 g) (hereinafter referred to as the compound of Reference Example 19) was obtained from 2-methoxy-5-(trifluoromethyl)aniline (5.0 g) according to a method similar to that described in Reference Example 7.

$^1$H-NMR (400 MHz, CDCl$_3$) δ (ppm): 3.97 (3H, s), 4.86 (2H, s), 6.95 (1H, d, J=8.5 Hz), 7.33 (1H, dd, J=8.9, 1.8 Hz), 7.52 (1H, s), 8.42 (1H, s).

MS(ESI) [M+H]$^+$: 366.

Example 18

Synthesis of 4-((2-((3-(2-methoxy-5-(trifluoromethyl)phenyl)ureido)methyl)phenoxy)methyl)benzamide

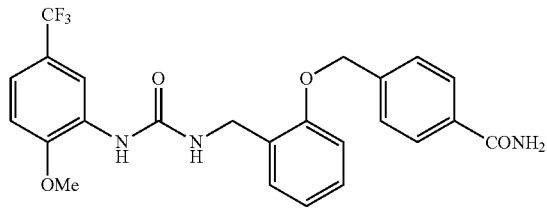 [SMILES: COc1ccc(C(F)(F)F)cc1NC(=O)NCc1ccccc1OCc1ccc(C(N)=O)cc1]

The title compound (21 mg) (hereinafter referred to as the compound of Example 18) was obtained as a white solid from the compound of Reference Example 19 (30 mg) and 4-((2-(aminomethyl)phenoxy)methyl)benzamide hydrochloride (23 mg) according to a method similar to that described in Example 10 (chloroform:methanol=10:1, Rf=0.32).

$^1$H-NMR (DMSO-d$_6$, 400 MHz) δ: 3.92 (3H, s), 4.37 (2H, d, J=4.0 Hz), 5.25 (2H, s), 6.94 (1H, t, J=8.0 Hz), 7.06 (1H, d, J=8.0 Hz), 7.14 (2H, d, J=8.0 Hz), 7.22-7.27 (3H, m), 7.33-7.40 (2H, m), 7.56 (2H, d, J=8.0 Hz), 7.88 (2H, d, J=8.0 Hz), 7.97 (1H, br), 8.36 (1H, s), 8.54 (1H, d, J=4.0 Hz).

MS(ESI) [M+H]$^+$: 474.

Example 19

Synthesis of 4-((2-((3-(3-(trifluoromethyl)phenyl)ureido)methyl)phenoxy)methyl)benzamide

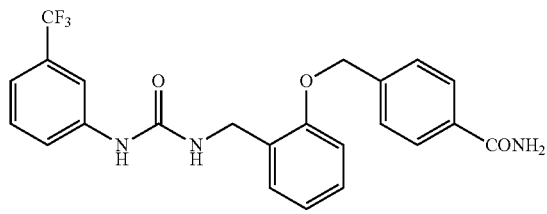 [SMILES: NC(=O)c1ccc(COc2ccccc2CNC(=O)Nc2cccc(C(F)(F)F)c2)cc1]

The title compound (23 mg) (hereinafter referred to as the compound of Example 19) was obtained as a white solid from 2,2,2-trichloroethyl(3-(trifluoromethyl)phenyl)carbamate (30 mg) and 4-((2-(aminomethyl)phenoxy)methyl)benzamide hydrochloride (23 mg) according to a method similar to that described in Example 10 (chloroform:methanol=10:1, Rf=0.49).

$^1$H-NMR (DMSO-$d_6$, 400 MHz) δ: 4.37 (2H, d, J=4.0 Hz), 5.25 (2H, s), 6.62 (1H, t, J=4.0 Hz), 6.94 (1H, t, J=8.0 Hz), 7.05 (1H, d, J=8.0 Hz), 7.21-7.27 (3H, m), 7.37 (1H, br), 7.43-7.51 (2H, m), 7.57 (2H, d, J=8.0 Hz), 7.89 (2H, d, J=8.0 Hz), 7.98 (1H, br).

MS(ESI) [M+H]$^+$: 444.

Example 20

Synthesis of 4-((2-((3-(3-(hydroxymethyl)-2-methoxy-5-(trifluoromethyl)phenyl)ureido)methyl)phenoxy)methyl)benzamide

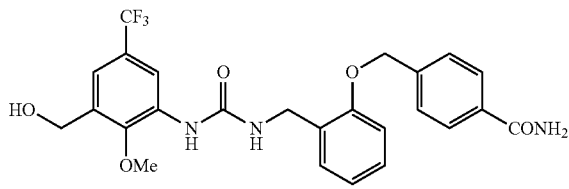 [SMILES: COc1c(CO)cc(C(F)(F)F)cc1NC(=O)NCc1ccccc1OCc1ccc(C(N)=O)cc1]

The title compound (21 mg) (hereinafter referred to as the compound of Example 20) was obtained as a white solid from the compound of Reference Example 17 (30 mg) and 4-((2-(aminomethyl)phenoxy)methyl)benzamide hydrochloride (19 mg) according to a method similar to that described in Example 10 (hexane:ethyl acetate=1:4, Rf=0.27).

$^1$H-NMR (DMSO-$d_6$, 400 MHz) δ: 3.72 (3H, s), 4.36 (2H, d, J=8.0 Hz), 4.59 (2H, d, J=8.0 Hz), 5.25 (2H, s), 5.34 (1H, t, J=4.0 Hz), 6.95 (1H, t, J=8.0 Hz), 7.06 (2H, d, J=8.0 Hz), 7.22-7.36 (5H, m), 7.56 (2H, d, J=8.0 Hz), 7.88 (2H, d, J=8.0 Hz), 8.46 (1H, s), 8.52 (1H, d, J=4.0 Hz).

MS(ESI) [M+H]$^+$: 504.

Example 21

Synthesis of 3-((2-((3-(2-methoxy-5-(trifluoromethyl)phenyl)ureido)methyl)phenoxy)methyl)benzamide

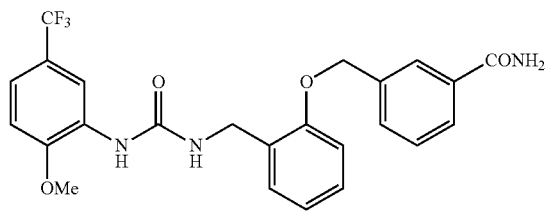 [SMILES: COc1ccc(C(F)(F)F)cc1NC(=O)NCc1ccccc1OCc1cccc(C(N)=O)c1]

The title compound (21 mg) (hereinafter referred to as the compound of Example 21) was obtained as a foam from the compound of Reference Example 19 (30 mg) and 3-((2-(aminomethyl)phenoxy)methyl)benzamide hydrochloride (21 mg) according to a method similar to that described in Example 10 (chloroform:methanol=10:1, Rf=0.53).

$^1$H-NMR (DMSO-$d_6$, 400 MHz) δ: 3.91 (3H, s), 4.35 (2H, d, J=4.0 Hz), 5.22 (2H, s), 6.95 (1H, t, J=8.0 Hz), 7.09 (1H, d, J=12.0 Hz), 7.13 (1H, d, J=8.0 Hz), 7.22-7.27 (3H, m), 7.34 (1H, t, J=8.0 Hz), 7.40-7.52 (2H, m), 8.39 (1H, s), 8.53 (1H, d, J=2.0 Hz).

MS(ESI) [M+H]$^+$: 474.

Example 22

Synthesis of 3-((2-((3-(3-(hydroxymethyl)-2-methoxy-5-trifluoromethyl)phenyl)ureido)methyl)phenoxy)methyl)benzamide

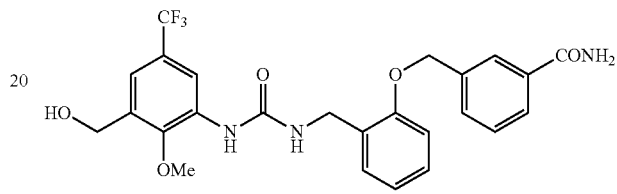

The title compound (19 mg) (hereinafter referred to as the compound of Example 22) was obtained as a foam from the compound of Reference Example 17 (30 mg) and 3-((2-(aminomethyl)phenoxy)methyl)benzamide hydrochloride (19 mg) according to a method similar to that described in Example 10 (chloroform:methanol=10:1, Rf=0.50).

$^1$H-NMR (DMSO-$d_6$, 400 MHz) δ: 3.71 (3H, s), 4.36 (2H, d, J=8.0 Hz), 4.59 (2H, d, J=8.0 Hz), 5.23 (2H, s), 5.35 (1H, t, J=4.0 Hz), 6.96 (1H, t, J=8.0 Hz), 7.08 (1H, d, J=8.0 Hz), 7.22-7.30 (3H, m), 7.40-7.50 (3H, m), 7.66 (2H, d, J=8.0 Hz), 7.82 (2H, d, J=8.0 Hz), 7.99-8.10 (2H, m), 8.45 (1H, s), 8.51 (1H, d, J=2.0 Hz).

MS(ESI) [M+H]$^+$: 504.

Example 23

Synthesis of 1-(2-methoxy-5-(pentafluorosulfanyl)phenyl)-3-(2-(pyridin-4-yloxy)benzyl)urea hydrochloride

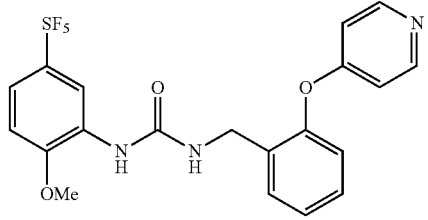

To a solution of the compound of Reference Example 1 (815 mg, 2.05 mmol) in N,N-dimethylformamide (3.0 mL), sodium hydride (55% by weight in mineral oil, 98 mg, 2.3 mmol) was added under cooling on ice, and the obtained solution was stirred at room temperature for 15 minutes. The obtained solution was again cooled on ice to add 2-chloro-4-nitropyridine (389 mg, 2.45 mmol) thereto, and the obtained solution was stirred at room temperature for two hours. A saturated aqueous solution of ammonium chloride was added to the solution to stop the reaction, and the obtained solution was subsequently extracted with ethyl acetate. The organic layer was dried over anhydrous sodium sulfate and then concentrated under vacuum. Diethyl ether was added to the obtained crude product and the precipitated white solid was recovered by filtration (510 mg, 49%). The obtained intermediate was dissolved in methanol (5.0 mL), and palladium (10% by weight) on carbon (containing 50% water by weight, 50 mg) was added thereto, and the obtained solution was stirred overnight at room temperature under hydrogen atmosphere. The reaction mixture was filtered through Celite® and the filtrate was concentrated under vacuum. Diethyl ether was added to the obtained residue, and the precipitated solid was recovered by filtration and dried to obtain the title compound (490 mg, quant) (hereinafter referred to as the compound of Example 23) as a white solid.

$^1$H-NMR (DMSO-$d_6$, 400 MHz) δ (ppm): 3.92 (3H, s), 4.25 (2H, d, J=4.0 Hz), 7.12 (2H, d, J=8.0 Hz), 7.25-7.35 (3H, m), 7.39-7.49 (4H, m), 7.55 (1H, d, J=8.0 Hz), 8.22 (1H, brs), 8.65 (1H, brs), 8.70 (2H, brs).

MS(ESI) [M+H]$^+$: 476.

Reference Example 20

Synthesis of 1-(2-((2-chloropyrimidin-4-yl)oxy)benzyl)-3-(2-methoxy-5-(pentafluorosulfanyl)phenyl)urea

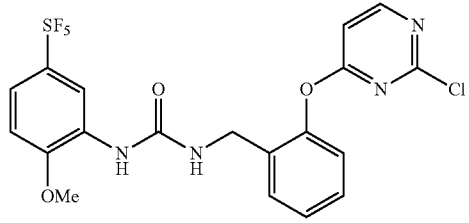

To a solution of the compound of Reference Example 1 (5.0 g, 12.6 mmol) in N,N-dimethylformamide (10 mL), sodium hydride (55% by weight in mineral oil, 602 mg, 13.8 mmol) was added under cooling on ice, and the obtained solution was stirred at room temperature for 15 minutes. Subsequently, 2,4-dichloropyrimidine (2.24 g, 15.1 mmol) was added. After stirring the obtained solution at room temperature for two hours, a saturated aqueous solution of ammonium chloride was added to the reaction mixture and the obtained solution was extracted with ethyl acetate. The organic layer was dried over anhydrous sodium sulfate, diethyl ether was added thereto, and the obtained solution was stirred overnight at room temperature. The precipitated white solid was recovered by filtration to obtain the title compound (3.6 g, 56%) (hereinafter referred to as the compound of Reference Example 20).

MS(ESI) [M+H]$^+$: 511.

Example 24

Synthesis of 1-(2-((2-(1H-imidazol-1-yl)pyrimidin-4-yl)oxy)benzyl)-3-(2-methoxy-5-(pentafluorosulfanyl)phenyl)urea

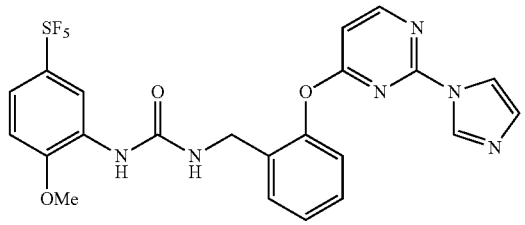

A solution of the compound of Reference Example 20 (20 mg, 0.039 mmol), 1H-imidazole (35 mg, 0.52 mmol) and triethylamine (0.077 mL, 0.55 mmol) in ethanol (4.0 mL) was stirred at 60° C. for 192 hours, and the reaction solution was then concentrated under vacuum. The obtained crude product was purified by silica gel column chromatography (chloroform:methanol=20:1, Rf=0.40) to obtain the title compound (9.9 mg, 47%) (hereinafter referred to as the compound of Example 24).

$^1$H-NMR (DMSO-$d_6$, 400 MHz) δ (ppm): 3.86 (3H, s), 4.28 (2H, d, J=5.4 Hz), 6.97-7.08 (3H, m), 7.29-7.60 (7H, m), 8.21-8.23 (2H, m), 8.62-8.64 (2H, m).

Example 25

Synthesis of methyl 4-((2-((3-(2-methoxy-5-(trifluoromethoxy)phenyl)ureido)methyl)phenoxy)benzoate

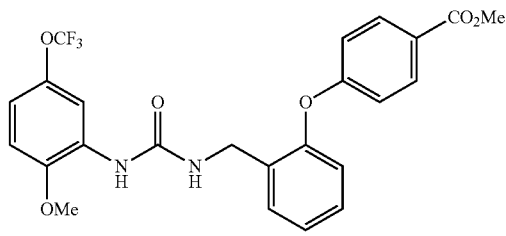 [SMILES: COC(=O)c1ccc(Oc2ccccc2CNC(=O)Nc2cc(OC(F)(F)F)ccc2OC)cc1]

A solution of the compound of Reference Example 11 (400 mg, 1.04 mmol), methyl 4-fluorobenzoate (208 mg, 1.55 mmol) and potassium carbonate (326 mg, 2.36 mmol) in N,N-dimethylformamide was stirred for 30 minutes at 150° C. by using the microwave reactor and then concentrated under vacuum. The obtained crude product was purified by silica gel column chromatography (hexane:ethyl acetate=1:1, Rf=0.49) to obtain the title compound (19 mg, 3.4%) (hereinafter referred to as the compound of Example 25) as a white solid.

$^1$H-NMR (CDCl$_3$, 400 MHz) δ: 3.81 (3H, s), 3.89 (3H, s), 4.45 (2H, d, J=4.0 Hz), 4.95 (1H, t, J=4.0 Hz), 6.73-6.79 (3H, m), 6.94-6.99 (3H, m), 7.21 (1H, td, J=8.0, 4.0 Hz), 7.32 (1H, t, J=8.0 Hz), 7.54 (1H, dd, J=8.0, 4.0 Hz), 8.00 (2H, d, J=8.0 Hz), 8.09 (1H, s).

MS(ESI) [M+H]$^+$: 491.

Example 26

Synthesis of 4-((2-((3-(2-methoxy-5-(trifluoromethoxy)phenyl)ureido)methyl)phenoxy)benzoic acid

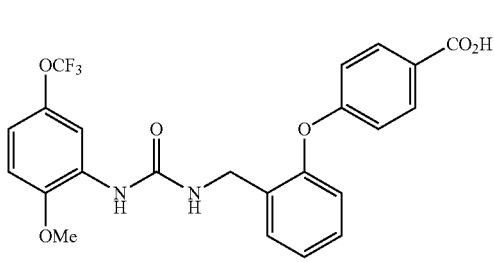 [SMILES: COc1ccc(OC(F)(F)F)cc1NC(=O)NCc1ccccc1Oc1ccc(C(=O)O)cc1]

The title compound (16 mg) (hereinafter referred to as the compound of Example 26) was obtained as a white solid from the compound of Example 25 (20 mg) according to a method similar to that described in Example 8 (chloroform:methanol=10:1, Rf=0.34).

$^1$H-NMR (DMSO-$d_6$, 400 MHz) δ: 3.86 (3H, s), 4.25 (2H, d, J=4.0 Hz), 6.84 (1H, dd, J=8.0, 4.0 Hz), 6.97-7.00 (3H, m), 7.03-7.06 (2H, m), 7.26 (1H, td, J=8.0, 4.0 Hz), 7.32-7.41 (2H, m), 7.45 (1H, dd, J=8.0, 4.0 Hz), 7.93 (2H, d, J=8.0 Hz), 8.15 (1H, s), 8.29 (1H, s).

MS(ESI) [M+H]$^+$: 477.

Example 27

Synthesis of 4-((2-((3-(2-methoxy-5-(trifluoromethoxy)phenyl)ureido)methyl)phenoxy)benzamide

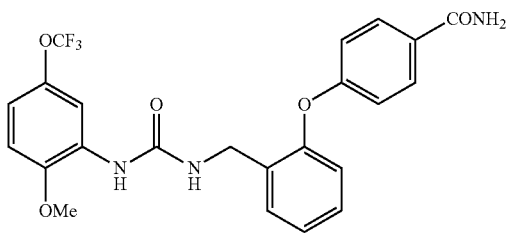 [SMILES: COc1ccc(OC(F)(F)F)cc1NC(=O)NCc1ccccc1Oc1ccc(C(N)=O)cc1]

The title compound (11 mg) (hereinafter referred to as the compound of Example 27) was obtained as a foam from the compound of Example 26 (15 mg) according to a method similar to that described in Example 12 (chloroform:methanol=10:1, R=0.43).

$^1$H-NMR (DMSO-$d_6$, 400 MHz) δ: 3.86 (3H, s), 4.26 (2H, d, J=4.0 Hz), 6.85 (1H, dd, J=8.0, 4.0 Hz), 6.94-7.04 (3H, m), 7.22-7.35 (3H, m), 7.42-7.45 (2H, m), 7.90 (2H, d, J=8.0 Hz), 8.15 (1H, s), 8.33 (1H, s).

MS(ESI) [M+H]$^+$: 476.

Reference Example 21

Synthesis of ethyl 4-(2-cyanophenoxy)benzoate

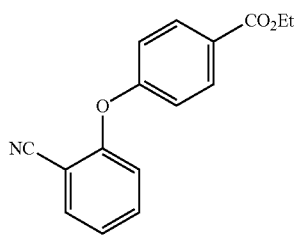 [SMILES: CCOC(=O)c1ccc(Oc2ccccc2C#N)cc1]

A solution of ethyl 4-fluorobenzoate (2.0 g, 13.5 mmol), 2-hydroxybenzonitrile (3.11 g, 26.0 mmol) and potassium carbonate (3.48 g, 25.0 mmol) in N-methyl-2-pyrrolidone (10 mL) was stirred while heating at 170° C. for eight hours. A saturated aqueous solution of ammonium chloride was added to the reaction mixture to stop the reaction, and the obtained solution was subsequently extracted with ethyl acetate and washed with saturated brine. The organic layer was dried over anhydrous sodium sulfate and then concentrated under vacuum, and the obtained crude product was purified by silica gel column chromatography (hexane:ethyl acetate=1:1, Rf=0.71) to obtain the title compound (1.2 g, 33%) (hereinafter referred to as the compound of Reference Example 21) as an oily substance.

MS(ESI) [M+H]$^+$: 268.

Reference Example 22

Synthesis of ethyl 4-(2-(aminomethyl)phenoxy)benzoate

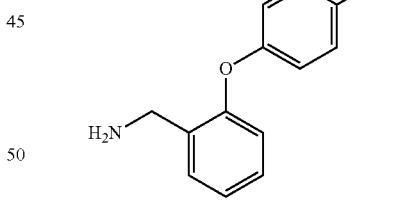

To a solution of the compound of Reference Example 21 (0.15 g, 0.56 mmol) in methanol (10 mL), Raney nickel (50% by weight dispersion in water, 3.0 ml) was added, and the obtained solution was stirred at room temperature for 10 hours under hydrogen atmosphere. After removing the Raney nickel by filtration with Celite®, the obtained solution was concentrated under vacuum. The obtained crude product was purified by silica gel column chromatography (amino-silica gel, chloroform:methanol=10:1, Rf=0.28) to obtain the title compound (0.082 g, 54%) (hereinafter referred to as the compound of Reference Example 22) as an oily substance.

MS(ESI) [M+H]$^+$: 272.

Reference Example 23

Synthesis of 4-(2-(((tert-butoxycarbonyl)amino)methyl)phenoxy)benzoic acid

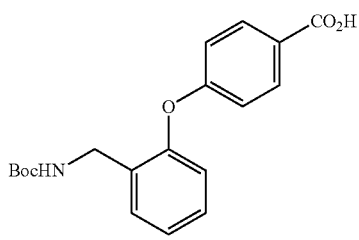 [SMILES: CC(C)(C)OC(=O)NCc1ccccc1Oc1ccc(C(=O)O)cc1]

The compound of Reference Example 21 (1.5 g, 5.6 mmol) was catalytically reduced under conditions similar to those described in Reference Example 22, and the solution in methanol obtained after filtration with Celite® was supplemented with a half the volume of a saturated aqueous solution of sodium bicarbonate. Di(tert-butyl) dicarbonate (1.35 g, 6.2 mmol) was added thereto and the obtained solution was stirred overnight at room temperature. A saturated aqueous solution of ammonium chloride was added to the reaction mixture to stop the reaction, and the obtained solution was subsequently extracted with ethyl acetate and washed with saturated brine. The organic layer was dried over anhydrous sodium sulfate and then concentrated under vacuum, and the crude product (1.5 g) was obtained. To a solution of the obtained crude product in tetrahydrofuran/methanol, a 1.0 N aqueous solution of sodium hydroxide was added, and the obtained solution was stirred overnight at room temperature. The obtained solution was adjusted to pH 5 or below with 1.0 N hydrochloric acid and then extracted with ethyl acetate. The ethyl acetate solution was washed with saturated brine, dried over anhydrous sodium sulfate, and then concentrated under vacuum. The obtained crude product was purified by silica gel column chromatography (chloroform:methanol=10:1, Rf=0.32) to obtain the title compound (1.41 g, 73%) (hereinafter referred to as the compound of Reference Example 23) as a pale yellow solid.
MS(ESI) [M+H]$^+$: 344.

Reference Example 24

Synthesis of methyl 4-(2-(aminomethyl)phenoxy)benzoate

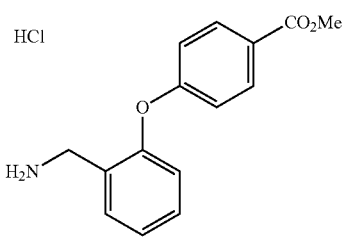 [SMILES: Cl ; COC(=O)c1ccc(Oc2ccccc2CN)cc1]

To a solution of the compound of Reference Example 23 (90 mg) in methanol, a 4.0 N solution of hydrogen chloride in 1,4-dioxane was added, and the obtained solution was left to stand overnight at room temperature. The reaction mixture was concentrated under vacuum, and the title compound (80 mg) (hereinafter referred to as the compound of Reference Example 24) was obtained as a white solid.
MS(ESI) [M+H]$^+$: 258.

Reference Example 25

Synthesis of 4-(2-(aminomethyl)phenoxy)benzamide hydrochloride

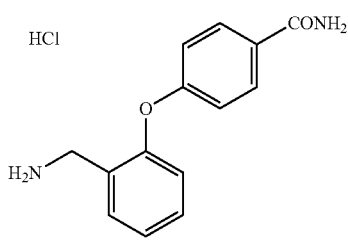 [SMILES: NCc1ccccc1Oc1ccc(C(N)=O)cc1 ; Cl]

To a solution of the compound of Reference Example 23 (0.2 g, 0.58 mmol) and 2-(7-aza-1H-benzotriazol-1-yl)-1,1,3,3-tetramethyluronium hexafluorophosphate (244 mg, 0.64 mmol) in N,N-dimethylformamide, diisopropylethylamine (113 mg) was added, and the obtained solution was stirred at room temperature for 30 minutes. An excess amount of a 7.0 N solution of ammonium in methanol was added to the solution, and successively the obtained solution was stirred for 30 minutes. Water and a 1.0 N hydrochloric acid solution were added to the reaction solution and the obtained solution was extracted with ethyl acetate. The organic layer was dried over anhydrous sodium sulfate and then concentrated under vacuum. The obtained crude product was purified by silica gel column chromatography (chloroform:methanol=10:1, Rf=0.42) to obtain an intermediate as a white solid. To a solution of the obtained white solid in methanol, a 4.0 N solution of hydrogen chloride in 1,4-dioxane was added, and the obtained solution was left to stand overnight at room temperature. The obtained solution was concentrated under vacuum, and the title compound (80 mg, 57%) (hereinafter referred to as the compound of Reference Example 25) was obtained as a white solid.
MS(ESI) [M+H]$^+$: 243.

Example 28

Synthesis of 4-((2-((3-(3-(hydroxymethyl)-2-methoxy-5-(trifluoromethyl)phenyl)ureido)methyl)phenoxy)benzoic acid

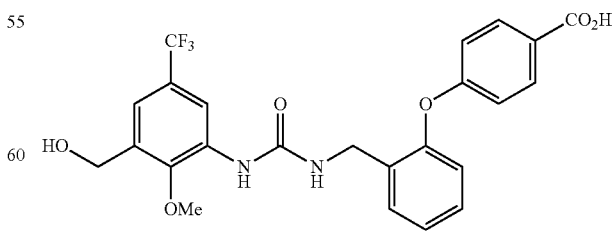

An ethyl ester derivative (35 mg) was obtained as an intermediate from the compound of Reference Example 17 (42 mg) and the compound of Reference Example 22 (27 mg) according to a method similar to that described in Example 10. The title compound (21 mg) (hereinafter referred to as the compound of Example 28) was obtained as a white solid from the obtained ethyl ester derivative (27 mg) according to a method similar to that described in Example 8 (chloroform:methanol=10:1, Rf=0.28).

$^1$H-NMR (DMSO-$d_6$, 400 MHz) δ: 3.69 (3H, s), 4.28 (2H, d, J=4.0 Hz), 4.58 (2H, s), 5.33 (1H, brs), 6.99 (2H, dd, J=8.0, 4.0 Hz), 7.04 (1H, d, J=8.0 Hz), 7.25-7.29 (2H, m), 7.34-7.41 (2H, m), 7.48 (1H, d, J=8.0 Hz), 7.93 (2H, dd, J=8.0, 4.0 Hz), 8.40 (1H, s), 8.44 (1H, d, J=2.0 Hz).

MS(ESI) [M+H]$^+$: 491.

Example 29

Synthesis of 4-((2-((3-(3-(hydroxymethyl)-2-methoxy-5-(trifluoromethyl)phenyl)ureido)methyl)phenoxy)benzamide

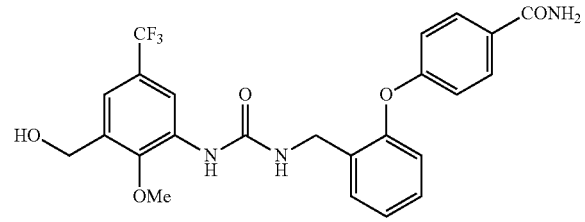 [SMILES: COc1c(CO)cc(C(F)(F)F)cc1NC(=O)NCc1ccccc1Oc1ccc(C(N)=O)cc1]

The title compound (18 mg) (hereinafter referred to as the compound of Example 29) was obtained as a white solid from the compound of Example 28 (30 mg) according to a method similar to that described in Example 12 (chloroform:methanol=10:1, Rf=0.32).

$^1$H-NMR (DMSO-$d_6$, 400 MHz) δ: 3.70 (3H, s), 4.29 (2H, d, J=4.0 Hz), 6.95-7.01 (3H, m), 7.23-7.48 (6H, m), 7.89 (1H, s), 7.91 (2H, s), 8.43 (1H, s), 8.45 (1H, d, J=2.0 Hz).

MS(ESI) [M+H]$^+$: 490.

Example 30

Synthesis of 4-((2-((3-(2-methoxy-5-(trifluoromethyl)phenyl)ureido)methyl)phenoxy)benzoic acid

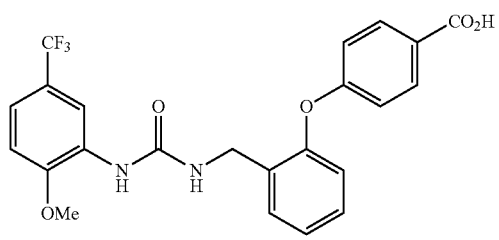 [SMILES: COc1ccc(C(F)(F)F)cc1NC(=O)NCc1ccccc1Oc1ccc(C(=O)O)cc1]

An ethyl ester derivative (32 mg) was obtained as an intermediate from the compound of Reference Example 19 (42 mg) and the compound of Reference Example 22 (27 mg) according to a method similar to that described in Example 10. The title compound (23 mg) (hereinafter referred to as the compound of Example 30) was obtained as a white solid from the obtained ethyl ester derivative (32 mg) according to a method similar to that described in Example 8 (chloroform:methanol=10:1, Rf=0.42).

$^1$H-NMR (DMSO-$d_6$, 400 MHz) δ: 3.91 (3H, s), 4.26 (2H, d, J=8.0 Hz), 6.99 (2H, dd, J=8.0, 4.0 Hz), 7.04 (1H, d, J=8.0 Hz), 7.12 (1H, d, J=8.0 Hz), 7.22-7.29 (2H, m), 7.34-7.47 (3H, m), 7.93 (2H, dd, J=8.0, 4.0 Hz), 8.32 (1H, s), 8.49 (1H, d, J=2.0 Hz).

MS(ESI) [M+H]$^+$: 461.

Example 31

Synthesis of 4-((2-((3-(2-methoxy-5-(trifluoromethyl)phenyl)ureido)methyl)phenoxy)benzamide

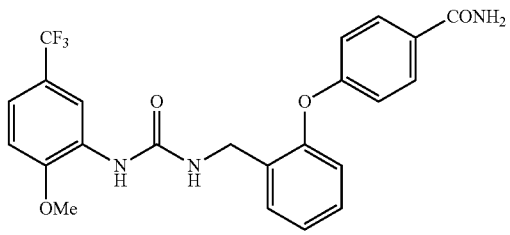

The title compound (19 mg) (hereinafter referred to as the compound of Example 31) was obtained as a white solid from the compound of Example 30 (30 mg) according to a method similar to that described in Example 13 (chloroform:methanol=10:1, Rf=0.40).

$^1$H-NMR (DMSO-$d_6$, 400 MHz) δ: 3.92 (3H, s), 4.27 (2H, d, J=8.0 Hz), 6.96-7.00 (3H, m), 7.13 (1H, d, J=8.0 Hz), 7.22-7.36 (4H, m), 7.40-7.45 (2H, m), 7.90 (3I, d, J=8.0 Hz), 8.36 (1H, s), 8.49 (1H, d, J=2.0 Hz).

MS(ESI) [M+H]$^+$: 460.

Example 32

Synthesis of 4-((2-((3-(5-(trifluoromethyl)phenyl)ureido)methyl)phenoxy)benzamide

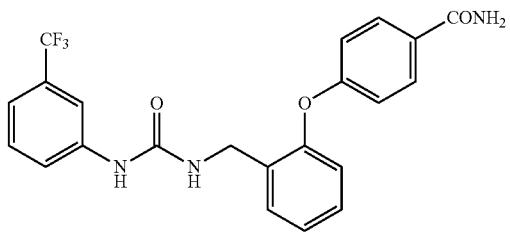

An ethyl ester derivative was obtained from phenyl (3-(trifluoromethyl)phenyl)carbamate (30 mg) and the compound of Reference Example 22 (29 mg) according to a method similar to that described in Example 10. A carboxylic acid derivative was obtained from the obtained ethyl ester derivative according to a method similar to that described in Example 8. The title compound (18 mg) (hereinafter referred to as the compound of Example 32) was obtained as a white solid from the obtained carboxylic acid derivative according to a method similar to that described in Example 12 (chloroform:methanol=10:1, Rf=0.47).

$^1$H-NMR (DMSO-$d_6$, 400 MHz) δ: 4.28 (2H, d, J=8.0 Hz), 6.73 (1H, t, J=8.0 Hz), 6.96-7.00 (3H, m), 7.22-7.36 (4H, m), 7.42-7.51 (3H, m), 7.90 (3H, d, J=8.0 Hz), 7.96 (1H, s).

MS(ESI) [M+H]$^+$: 430.

Reference Example 26

Synthesis of 2,2,2-trichloroethyl (2-(oxetan-3-yloxy)-5-(trifluoromethyl)phenyl)carbamate

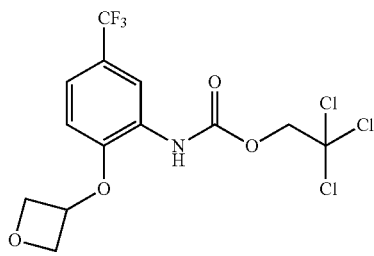 [SMILES: O=C(Nc1cc(C(F)(F)F)ccc1OC1COC1)OCC(Cl)(Cl)Cl]

To a solution of 1-chloro-2-nitro-4-(trifluoromethyl)benzene (3.2 g, 5.2 mmol) in N,N-dimethylformamide (20 mL), sodium hydride (55% by weight in mineral oil, 0.41 g, 7.6 mmol) was added under cooling on ice. After stirring the obtained solution at room temperature for 30 minutes, oxetan-3-ol (3.2 g, 43 mmol) was added. After stirring the obtained solution overnight at room temperature, water was added to the reaction solution, and the obtained solution was extracted with ethyl acetate. The organic layer was sequentially washed with a saturated aqueous solution of ammonium chloride and with a saturated aqueous solution of sodium chloride. The obtained organic layer was dried over anhydrous sodium sulfate and then concentrated under vacuum, and a crude product was obtained. At room temperature, palladium (10% by weight) on carbon (containing 50% water by weight, 0.10 g) was added to a solution of the obtained crude product in methanol (20 mL), and the obtained solution was stirred for five hours under hydrogen atmosphere. The reaction mixture was filtrated through Celite®, the filtrate was concentrated under vacuum, and a crude product was obtained. To a solution of the obtained crude product and diisopropylethylamine (3.8 mL, 22 mmol) in tetrahydrofuran (30 mL), 2,2,2-trichloroethyl chloroformate (3.3 g, 16 mmol) was added under cooling on ice. After stirring the obtained solution overnight at room temperature, water was added to the reaction solution, and the obtained solution was extracted with ethyl acetate. The organic layer was sequentially washed with a saturated aqueous solution of ammonium chloride and with a saturated aqueous solution of sodium chloride. The obtained organic layer was dried over anhydrous sodium sulfate and then concentrated under vacuum. The obtained crude product was provided for recrystallization from a mixed solution of hexane and diethyl ether (20:1), and the precipitated solid was recovered by filtration to obtain the title compound (3.8 g, 66%) (hereinafter referred to as the compound of Reference Example 26) as a white solid.

$^1$H-NMR (400 MHz, CDCl$_3$) δ (ppm): 4.83 (2H, dd, J=8.3, 5.1 Hz), 4.88 (2H, s), 5.05 (2H, dd, J=7.7, 6.7 Hz), 5.29-5.35 (1H, m), 6.49 (1H, d, J=8.5 Hz), 7.29 (1H, d, J=2.0 Hz), 7.46 (1H, s), 8.47 (1H, s).

MS(ESI) [M+H]$^+$: 408.

Reference Example 27

Synthesis of 2,2,2-trichloroethyl (2-(oxetan-3-yloxy)-5-(trifluoromethoxy)phenyl)carbamate

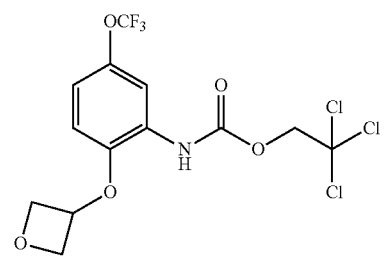 [SMILES: O=C(Nc1cc(OC(F)(F)F)ccc1OC1COC1)OCC(Cl)(Cl)Cl]

The title compound (0.12 g) (hereinafter referred to as the compound of Reference Example 27) was obtained as an oily substance from 1-chloro-2-nitro-4-(trifluoromethoxy)benzene (0.5 g) according to a method similar to that described in Reference Example 26. Purification of the title compound was performed by column chromatography (hexane:ethyl acetate=1:1, Rf=0.40).

MS(ESI) [M+H]$^+$: 424.

Example 33

Synthesis of 4-(2-((3-(2-(oxetan-3-yloxy)-5-(trifluoromethyl)phenyl)ureido)methyl)phenoxy)benzamide

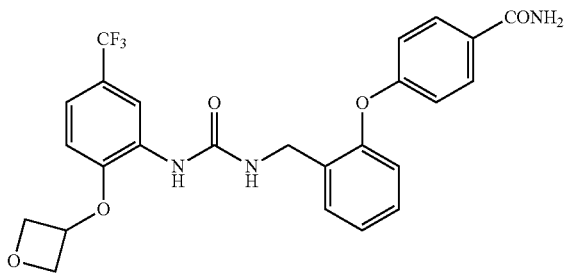 [SMILES: NC(=O)c1ccc(Oc2ccccc2CNC(=O)Nc2cc(C(F)(F)F)ccc2OC2COC2)cc1]

The title compound (21 mg) (hereinafter referred to as the compound of Example 33) was obtained as a white solid from the compound of Reference Example 25 (30 mg) and the compound of Reference Example 26 (20 mg) according to a method similar to that described in Example 10 (chloroform:methanol=10:1, Rf=0.35).

$^1$H-NMR (DMSO-d$_6$, 400 MHz) δ: 4.31 (2H, d, J=8.0 Hz), 4.63-4.67 (2H, m), 4.98 (2H, t, J=8.0 Hz), 5.41 (1H, t, J=4.0 Hz), 6.76 (1H, d, J=8.0 Hz), 6.94-7.01 (3H, m), 7.18 (1H, d, J=8.0 Hz), 7.24-7.37 (3H, m), 7.45-7.50 (2H, m), 7.80-7.90 (3H, m), 8.29 (1H, s), 8.54 (1H, s).

MS(ESI) [M+H]$^+$: 502.

Example 34

Synthesis of 4-(2-((3-(2-(oxetan-3-yloxy)-5-(trifluoromethoxy)phenyl)ureido)methyl)phenoxy)benzamide

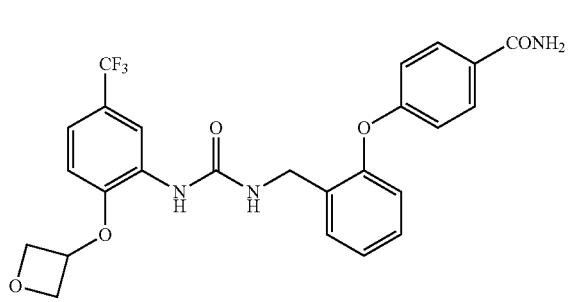 [SMILES: NC(=O)c1ccc(Oc2ccccc2CNC(=O)Nc2cc(C(F)(F)F)ccc2OC2COC2)cc1]

The title compound (16 mg) (hereinafter referred to as the compound of Example 34) was obtained as a white solid from the compound of Reference Example 25 (40 mg) and the compound of Reference Example 27 (42 mg) according to a method similar to that described in Example 10 (chloroform:methanol=10:1, Rf=0.32).

$^1$H-NMR (DMSO-d$_6$, 400 MHz) δ: 4.29 (2H, d, J=8.0 Hz), 4.62-4.68 (2H, m), 4.95 (2H, t, J=8.0 Hz), 5.33 (1H, t, J=4.0 Hz), 6.66 (1H, d, J=8.0 Hz), 6.80 (1H, dd, J=8.0, 4.0 Hz), 6.95-7.01 (3H, m), 7.24-7.37 (3H, m), 7.47-7.50 (2H, m), 7.89-7.91 (3H, m), 8.21 (1H, d, J=2.0 Hz), 8.24 (1H, s).

MS(ESI) [M+H]$^+$: 518.

Reference Example 28

Synthesis of methyl 3-amino-5-(trifluoromethyl)benzoate

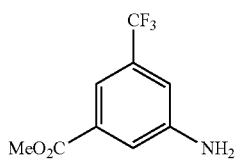

A solution of 3-nitro-5-(trifluoromethyl)benzoic acid (1.0 g, 4.2 mmol) and p-toluenesulfonic acid (0.05 g) in methanol was stirred while heating under reflux for eight hours. The obtained solution was returned to room temperature and then concentrated under vacuum. The obtained residue was dissolved in methanol, palladium (5.0% by weight) on carbon (containing 50% water by weight, 0.2 g) was added thereto, and the obtained solution was stirred at room temperature for three hours under hydrogen atmosphere. The reaction mixture was filtered through Celite® and the filtrate was concentrated under vacuum. The obtained crude product was purified by silica gel column chromatography (hexane:ethyl acetate=2:1, Rf=0.47) to obtain the title compound (0.85 g, 91%) (hereinafter referred to as the compound of Reference Example 28) as an oily substance.

MS(ESI) [M+H]$^+$: 220.

Reference Example 29

Synthesis of methyl 4-amino-2-(trifluoromethyl)benzoate

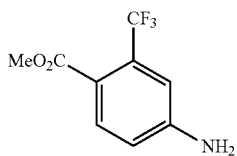 [SMILES: COC(=O)c1ccc(N)cc1C(F)(F)F]

The title compound (0.9 g) (hereinafter referred to as the compound of Reference Example 29) was obtained as an oily substance from 4-nitro-6-(trifluoromethyl)benzoic acid (1.0 g) according to a method similar to that described in Reference Example 28 (hexane:ethyl acetate=2:1, Rf=0.48).

MS(ESI) [M+H]$^+$: 220.

Reference Example 30

Synthesis of (3-amino-5-(trifluoromethyl)phenyl)methanol

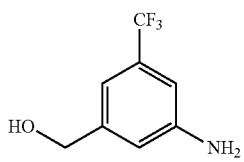 [SMILES: Nc1cc(CO)cc(C(F)(F)F)c1]

To a solution of the compound of Reference Example 28 (0.4 g, 1.8 mmol) in tetrahydrofuran, lithium aluminium hydride (0.22 g, 5.7 mmol) was added portionwise under cooling on ice. The obtained reaction mixture was returned to room temperature and then stirred for one hour. After adding water to the reaction mixture to stop the reaction, the obtained solution was extracted with ethyl acetate and sequentially washed with a saturated aqueous solution of ammonium chloride and with saturated brine. The organic layer was dried over anhydrous sodium sulfate and then concentrated under vacuum, and the obtained crude product was purified by silica gel column chromatography (hexane:ethyl acetate=1:1, Rf=0.32) to obtain the title compound (0.32 g, 92%) (hereinafter referred to as the compound of Reference Example 30) as a white solid.

MS(ESI) [M+H]$^+$: 192.

Reference Example 31

Synthesis of (4-amino-2-(trifluoromethyl)phenyl)methanol

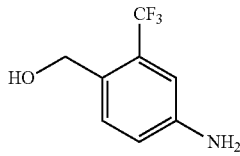 [SMILES: Nc1ccc(CO)c(C(F)(F)F)c1]

The title compound (0.31 g) (hereinafter referred to as the compound of Reference Example 31) was obtained as an oily substance from the compound of Reference Example 29 (0.4 g) according to a method similar to that described in Reference Example 30 (hexane:ethyl acetate=2:1, Rf=0.49).
MS(ESI) [M+H]⁺: 192.

Reference Example 32

Synthesis of 2,2,2-trichloroethyl (3-(hydroxymethyl)-5-(trifluoromethyl)phenyl)carbamate

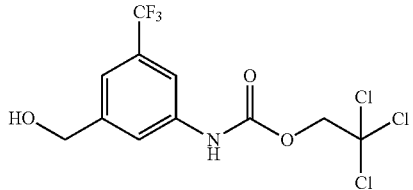 [SMILES: O=C(Nc1cc(CO)cc(C(F)(F)F)c1)OCC(Cl)(Cl)Cl]

The title compound (0.13 g) (hereinafter referred to as the compound of Reference Example 32) was obtained as a white solid from the compound of Reference Example 30 (0.32 g) according to a method similar to that described in Reference Example 7 (hexane:ethyl acetate=2:1, Rf=0.51).
MS(ESI) [M+Na]⁺: 388.

Reference Example 33

Synthesis of 2,2,2-trichloroethyl (4-(hydroxymethyl)-3-(trifluoromethyl)phenyl)carbamate

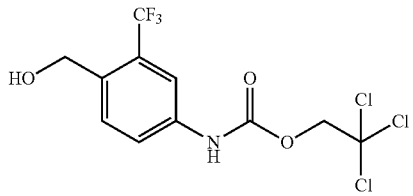 [SMILES: O=C(Nc1ccc(CO)c(C(F)(F)F)c1)OCC(Cl)(Cl)Cl]

The title compound (0.16 g) (hereinafter referred to as the compound of Reference Example 33) was obtained as a white solid from the compound of Reference Example 31 (0.13 g) according to a method similar to that described in Reference Example 32 (hexane:ethyl acetate=2:1, Rf=0.61).
MS(ESI) [M+H]⁺: 348.

Example 35

Synthesis of 4-((2-((3-(3-(hydroxymethyl)-5-(trifluoromethyl)phenyl)ureido)methyl)phenoxy)benzamide

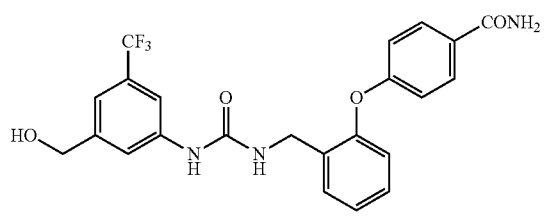 [SMILES: NC(=O)c1ccc(Oc2ccccc2CNC(=O)Nc2cc(CO)cc(C(F)(F)F)c2)cc1]

The title compound (46 mg) (hereinafter referred to as the compound of Example 35) was obtained as a white solid from the compound of Reference Example 25 (40 mg) and the compound of Reference Example 32 (61 mg) according to a method similar to that described in Example 10 (chloroform:methanol=10:1, Rf=0.27).
¹H-NMR (DMSO-d₆, 400 MHz) δ: 4.27 (2H, d, J=4.0 Hz), 4.51 (2H, d, J=8.0 Hz), 5.36 (1H, t, J=4.0 Hz), 6.68 (1H, br), 6.99-7.00 (3H, m), 7.17 (1H, br), 7.23 (1H, t, J=8.0 Hz), 7.31-7.35 (2H, m), 7.24-7.45 (2H, m), 7.82 (1H, s), 7.90 (3H, d, J=8.0 Hz), 9.02 (1H, s).
MS(ESI) [M+H]⁺: 460.

Example 36

Synthesis of 4-(2-((3-(4-(hydroxymethyl)-5-(trifluoromethyl)phenyl)ureido)methyl)phenoxy)benzamide

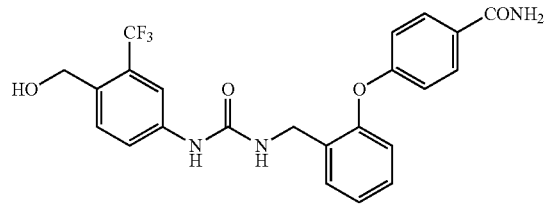 [SMILES: NC(=O)c1ccc(Oc2ccccc2CNC(=O)Nc2ccc(CO)c(C(F)(F)F)c2)cc1]

The title compound (42 mg) (hereinafter referred to as the compound of Example 36) was obtained as a white solid from the compound of Reference Example 25 (40 mg) and the compound of Reference Example 33 (61 mg) according to a method similar to that described in Example 10 (chloroform:methanol=10:1, Rf=0.26).
¹H-NMR (DMSO-d₆, 400 MHz) δ: 4.27 (2H, d, J=4.0 Hz), 4.56 (2H, d, J=4.0 Hz), 5.32 (1H, t, J=4.0 Hz), 6.66 (1H, br), 6.96-7.00 (3H, m), 7.23 (1H, t, J=8.0 Hz), 7.29-7.35 (2H, m), 7.43 (2H, d, J=8.0 Hz), 7.51 (2H, d, J=8.0 Hz), 7.58 (2H, d, J=8.0 Hz), 7.90 (4H, d, J=8.0 Hz), 8.94 (1H, s).
MS(ESI) [M-OH]⁺: 452.

Example 37

Synthesis of 4-(2-((3-(3-((4-methylpiperazin-1-yl)methyl)-5-(trifluoromethyl)phenyl)ureido)methyl)phenoxy)benzamide

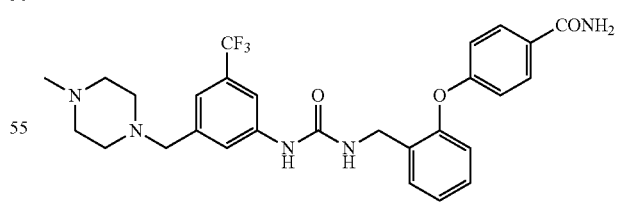

To a solution of the compound of Example 35 (20 mg, 0.04 mmol) and diisopropylethylamine (5.5 mg, 0.042 mmol) in tetrahydrofuran, methanesulfonyl chloride (5.5 mg, 0.048 mmol) was added under cooling on ice. After stirring the obtained solution for 30 minutes, 1-methylpiperazine (10 mg, 0.1 mmol) was added thereto, and the obtained solution was stirred overnight while returning the temperature to room temperature. A saturated aqueous solution of ammonium chloride was added to the reaction mixture to stop the reaction, and the obtained solution was subsequently extracted with ethyl acetate and washed with saturated brine. The organic layer was dried over anhydrous sodium sulfate and then concentrated under vacuum, and the obtained crude product was purified by silica gel column chromatography (amino-silica gel, chloroform:methanol=10:1, Rf=0.52) to obtain the title compound (5.0 mg, 21%) (hereinafter referred to as the compound of Example 37) as a white solid.

$^1$H-NMR (DMSO-$d_6$, 400 MHz) δ: 2.14 (3H, s), 2.35 (6H, bs), 3.43 (2H, s), 4.27 (2H, d, J=4.0 Hz), 6.66 (1H, t, J=4.0 Hz), 6.95-7.00 (3H, m), 7.10 (1H, br), 7.23 (1H, t, J=8.0 Hz), 7.26-7.35 (2H, m), 7.43 (2H, br), 7.82 (1H, s), 7.90 (3H, d, J=8.0 Hz), 9.05 (1H, s).

MS(ESI) [M+H]$^+$: 542.

Example 38

Synthesis of 4-(2-((3-(4-((4-methylpiperazin-1-yl)methyl)-3-(trifluoromethyl)phenyl)ureido)methyl)phenoxy)benzamide

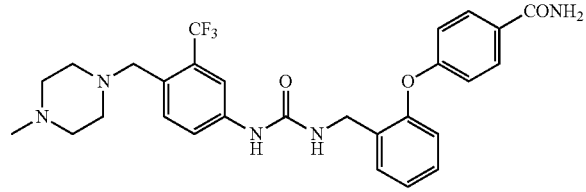 [SMILES: CN1CCN(Cc2ccc(NC(=O)NCc3ccccc3Oc3ccc(C(N)=O)cc3)cc2C(F)(F)F)CC1]

The title compound (5.0 mg) (hereinafter referred to as the compound of Example 38) was obtained as a white solid from the compound of Example 36 (20 mg) according to a method similar to that described in Example 35 (amino-silica gel, chloroform:methanol=10:1, Rf=0.48).

$^1$H-NMR (DMSO-$d_6$, 400 MHz) δ: 2.14 (3H, s), 2.35 (6H, br), 3.49 (2H, s), 4.27 (2H, d, J=4.0 Hz), 6.69 (1H, t, J=4.0 Hz), 6.95-7.00 (3H, m), 7.23 (1H, t, J=8.0 Hz), 7.26-7.35 (2H, m), 7.41 (1H, d, J=4.0 Hz), 7.48 (1H, d, J=8.0 Hz), 7.50-7.56 (1H, m), 7.89-7.91 (4H, m), 8.99 (1H, s).

MS(ESI) [M+H]$^+$: 542.

Reference Example 34

Synthesis of tert-butyl 4-(3-(((2,2,2-trichloroethoxy)carbonyl)amino)-5-(trifluoromethyl)benzyl) piperazine-1-carboxylate

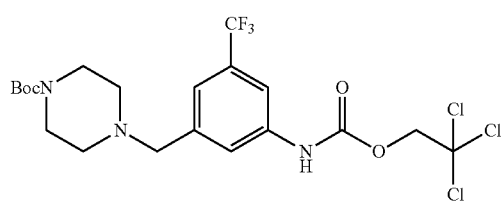 [SMILES: CC(C)(C)OC(=O)N1CCN(Cc2cc(NC(=O)OCC(Cl)(Cl)Cl)cc(C(F)(F)F)c2)CC1]

To a solution of the compound of Reference Example 32 (140 mg, 0.4 mmol) and diisopropylethylamine (223 mg, 1.7 mmol) in tetrahydrofuran, methanesulfonyl chloride (98 mg, 0.85 mmol) was added under cooling on ice. After stirring the obtained solution for 30 minutes, N-tert-butoxycarbonyl-piperazine (200 mg, 1.1 mmol) and potassium carbonate (98 mg, 0.71 mmol) were added thereto, and the obtained solution was stirred overnight at room temperature. A saturated aqueous solution of ammonium chloride was added to the reaction mixture to stop the reaction, and the obtained solution was subsequently extracted with ethyl acetate and washed with saturated brine. The organic layer was dried over anhydrous sodium sulfate and then concentrated under vacuum, and the obtained crude product was purified by silica gel column chromatography (amino-silica gel, hexane:ethyl acetate=1:1, Rf=0.43) to obtain the title compound (180 mg, 48%) (hereinafter referred to as the compound of Reference Example 34) as a foam.

MS(ESI) [M+H]$^+$: 535.

Reference Example 35

Synthesis of tert-butyl 4-(4-(((2,2,2-trichloroethoxy)carbonyl)amino)-5-(trifluoromethyl)benzyl)piperazine-1-carboxylate

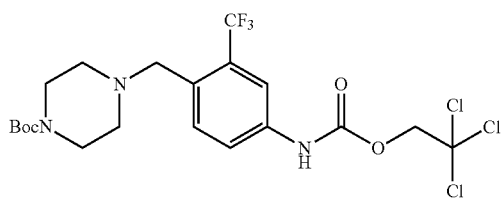 [SMILES: CC(C)(C)OC(=O)N1CCN(Cc2ccc(NC(=O)OCC(Cl)(Cl)Cl)cc2C(F)(F)F)CC1]

The title compound (180 mg) (hereinafter referred to as the compound of Reference Example 35) was obtained as a foam from the compound of Example 33 (140 mg) according to a method similar to that described in Reference Example 34 (amino-silica gel, hexane:ethyl acetate=1:1, Rf=0.43).

MS(ESI) [M+H]$^+$: 535.

Example 39

Synthesis of 4-(2-((3-(3-((piperazin-1-ylmethyl)-5-(trifluoromethyl)phenyl)ureido)methyl)phenoxy)benzamide hydrochloride

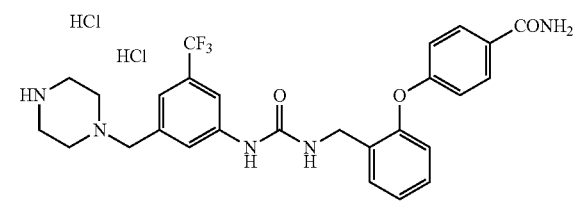 [SMILES: Cl ; NC(=O)c1ccc(Oc2ccccc2CNC(=O)Nc2cc(CN3CCNCC3)cc(C(F)(F)F)c2)cc1 ; Cl]

A tert-butoxycarbonyl-protected derivative was obtained as an intermediate from the compound of Reference Example 25 (15 mg) and the compound of Reference Example 34 (30 mg) according to a method similar to that described in Example 10 (chloroform:methanol=10:1, Rf=0.27). The title compound (15 mg) (hereinafter referred to as the compound of Example 39) was obtained as an oily substance from the tert-butoxycarbonyl-protected derivative according to a method similar to that described in Example 17.

¹H-NMR (DMSO-d₆, 400 MHz) δ: 3.43 (2H, s), 4.16 (6H, brs), 4.29 (2H, d, J=4.0 Hz), 4.43 (2H, s), 6.97-7.00 (3H, m), 7.10-7.38 (4H, m), 7.45 (1H, dd, J=8.0, 4.0 Hz), 7.60 (1H, br), 7.74 (1H, br), 7.90 (2H, d, J=8.0 Hz), 8.02 (1H, br), 9.61 (2H, s).
MS(ESI) [M+H]⁺: 528.

Example 40

Synthesis of 4-(2-((3-(4-((piperazin-1-ylmethyl)-5-(trifluoromethyl)phenyl)ureido)methyl)phenoxy) benzamide hydrochloride

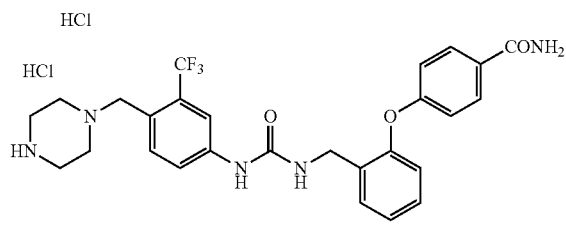 [SMILES: Cl ; Cl ; NC(=O)c1ccc(Oc2ccccc2CNC(=O)Nc2ccc(CN3CCNCC3)c(C(F)(F)F)c2)cc1]

A tert-butoxycarbonyl-protected derivative was obtained as an intermediate from the compound of Reference Example 25 (15 mg) and the compound of Reference Example 35 (30 mg) according to a method similar to that described in Example 10 (chloroform:methanol=10:1, Rf=0.32). The title compound (13 mg) (hereinafter referred to as the compound of Example 40) was obtained as an oily substance from the tert-butoxycarbonyl-protected derivative according to a method similar to that described in Example 17.
¹H-NMR (DMSO-d₆, 400 MHz) δ: 3.20-3.50 (8H, m), 4.05-4.39 (11H, m), 6.98 (3H, d, J=8.0 Hz), 7.20-7.35 (3H, m), 7.44 (1H, d, J=8.0 Hz), 7.61 (1H, d, J=8.0 Hz), 7.89 (3H, d, J=8.0 Hz), 8.02 (2H, br), 9.61 (2H, s).
MS(ESI) [M+H]⁺: 528.

Reference Example 36

Synthesis of tert-butyl 4-(2-nitro-4-(trifluoromethyl) phenoxy)piperidine-1-carboxylate

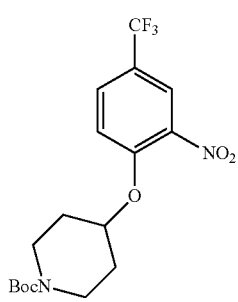 [SMILES: CC(C)(C)OC(=O)N1CCC(Oc2ccc(C(F)(F)F)cc2[N+](=O)[O-])CC1]

To a solution of tert-butyl 4-hydroxypiperidine-1-carboxylate (89 mg, 0.4 mmol) in N,N-dimethylformamide (5.0 mL), sodium hydride (55% by weight in mineral oil, 35 mg, 0.65 mmol) was added and stirred for 30 minutes under cooling on ice, and then 1-chloro-2-nitro-4-(trifluoromethyl) benzene (100 mg, 0.4 mmol) was added thereto. After stirring the obtained solution overnight at room temperature, a saturated aqueous solution of ammonium chloride was added to the reaction mixture and the obtained solution was extracted with ethyl acetate. The organic layer was washed with saturated brine, and subsequently dried over anhydrous sodium sulfate and concentrated, and the obtained crude product was purified by silica gel column chromatography (hexane:ethyl acetate=4:1, Rf=0.25) to obtain the title compound (113 mg, 65%) (hereinafter referred to as the compound of Reference Example 36) as a yellow oily substance.
MS(ESI) [M+H]⁺: 391.

Reference Example 37

Synthesis of tert-butyl 4-(2-amino-4-(trifluoromethyl)phenoxy)piperidine-1-carboxylate

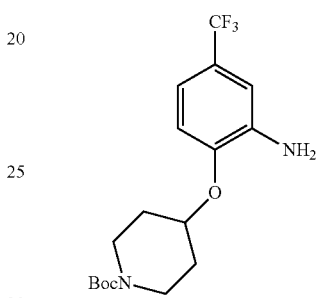

To a solution of the compound of Reference Example 36 (200 mg, 0.51 mmol) in methanol, palladium (10% by weight) on carbon (containing 50% water by weight, 0.05 g) was added, and the obtained solution was stirred for five hours under hydrogen atmosphere. The reaction mixture was filtrated through Celite®, the filtrate was concentrated under vacuum, and the obtained crude product was purified by silica gel column chromatography (hexane:ethyl acetate=1:1, Rf=0.34) to obtain the title compound (110 mg, 60%) (hereinafter referred to as the compound of Reference Example 37) as an oily substance.
MS(ESI) [M-tBu]⁺: 305.

Reference Example 38

Synthesis of tert-butyl (2-(((2,2,2-trichloroethoxy) carbonyl)amino-4-(trifluoromethyl)phenoxy)piperidine-1-carboxylate

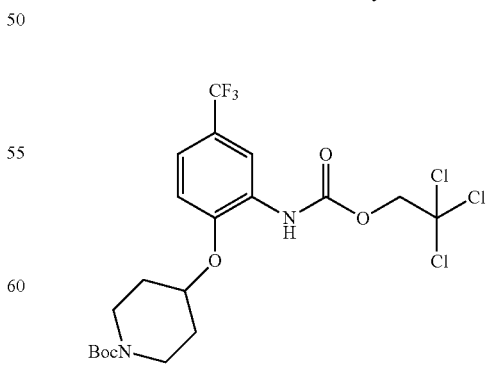

The title compound (0.13 g) (hereinafter referred to as the compound of Reference Example 38) was obtained as a white solid from the compound of Reference Example 37

(109 mg) according to a method similar to that described in Reference Example 7 (hexane:ethyl acetate=2:1, Rf=0.40).
MS(ESI) [M-Boc]+: 437.

Example 41

Synthesis of 4-(2-((3-(2-(piperidin-4-yloxy)-5-(trifluoromethyl)phenyl)ureido)methyl)phenoxy)benzamide

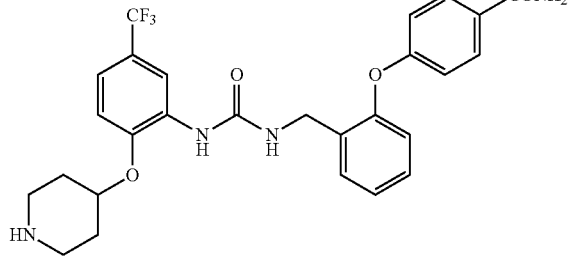

A tert-butoxycarbonyl-protected derivative was obtained as an intermediate from the compound of Reference Example 25 (45 mg) and the compound of Reference Example 38 (80 mg) according to a method similar to that described in Example 10 (chloroform:methanol=10:1, Rf=0.37). The title compound (23 mg) (hereinafter referred to as the compound of Example 41) was obtained as a foam from the tert-butoxycarbonyl-protected derivative according to a method similar to that described in Example 17 (aminosilica gel, chloroform:methanol=10:1, Rf=0.48).

$^1$H-NMR (DMSO-d$_6$, 400 MHz) δ: 1.54-1.62 (2H, m), 1.95-1.99 (2H, m), 2.50-2.70 (2H, m), 2.73 (1H, s), 2.89 (1H, s), 3.01-3.05 (2H, m), 4.29 (2H, d, J=4.0 Hz), 4.54-4.59 (1H, m), 6.95-7.00 (3H, m), 7.18-7.4 (5H, m), 7.47 (1H, d, J=8.0 Hz), 7.65-7.67 (1H, m), 7.89-7.95 (3H, m), 8.02 (1H, s), 8.49 (1H, s).
MS(ESI) [M+H]+: 529.

Reference Example 39

Synthesis of 4-(2-(aminomethyl)phenoxy)-N-methylbenzamide hydrochloride

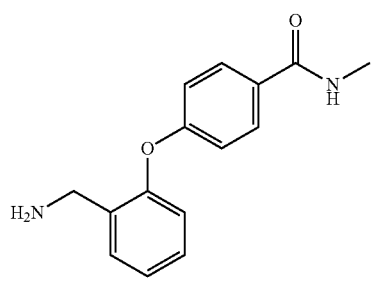 [SMILES: CNC(=O)c1ccc(Oc2ccccc2CN)cc1]

The title compound (80 mg) (hereinafter referred to as the compound of Reference Example 39) was obtained as a white solid from the compound of Reference Example 23 (0.2 g) according to a method similar to that described in Reference Example 25.
MS(ESI) [M+H]+: 257

Example 42

Synthesis of 4-((2-((3-(5-(trifluoromethyl)phenyl)ureido)methyl)phenoxy)-N-methyl-benzamide

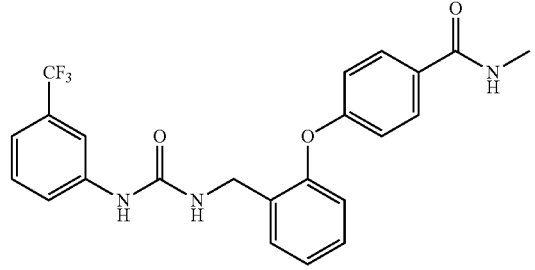 [SMILES: CNC(=O)c1ccc(Oc2ccccc2CNC(=O)Nc2cccc(C(F)(F)F)c2)cc1]

The title compound (16 mg) (hereinafter referred to as the compound of Example 42) was obtained as a white solid from phenyl (3-(trifluoromethyl)phenyl)carbamate (20 mg) and Reference Example 39 (22 mg) according to a method similar to that described in Example 10 (chloroform:methanol=10:1, Rf=0.52).

$^1$H-NMR (DMSO-d$_6$, 400 MHz) δ: 2.78 (3H, d, J=8.0 Hz), 4.28 (2H, d, J=8.0 Hz), 6.71 (1H, t, J=8.0 Hz), 6.98 (3H, d, J=8.0 Hz), 7.33 (1H, td, J=8.0, 2.0 Hz), 7.42-7.51 (3H, m), 8.35 (1H, d, J=4.0 Hz), 9.02 (1H, s).
MS(ESI) [M+H]+: 444.

Example 43

Synthesis of 4-(2-((3-(2-(oxetan-3-yloxy)-5-(trifluoromethyl)phenyl)ureido)methyl)phenoxy)-N-methyl-benzamide

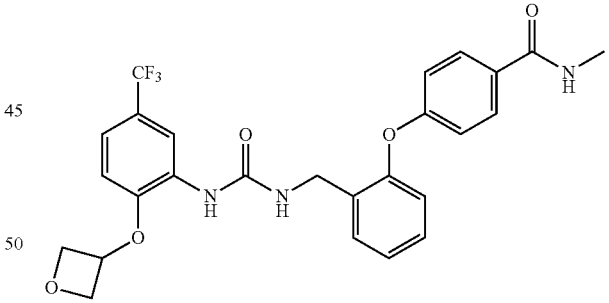

The title compound (13 mg) (hereinafter referred to as the compound of Example 43) was obtained as a white solid from the compound of Reference Example 26 (20 mg) and the compound of Reference Example 39 (15 mg) according to a method similar to that described in Example 10 (chloroform:methanol=10:1, Rf=0.35).

$^1$H-NMR (DMSO-d$_6$, 400 MHz) δ: 2.76 (3H, d, J=8.0 Hz), 4.31 (2H, d, J=8.0 Hz), 4.63-4.67 (2H, m), 4.98 (2H, t, J=8.0 Hz), 5.41 (1H, t, J=4.0 Hz), 6.75 (1H, d, J=8.0 Hz), 6.92-7.01 (3H, m), 7.16 (1H, d, J=8.0 Hz), 7.25 (1H, t, J=8.0 Hz), 7.37 (1H, td, J=8.0, 4.0 Hz), 7.46-7.50 (2H, m), 8.28 (1H, s), 8.36 (1H, d, J=4.0 Hz), 8.54 (1H, d, J=4.0 Hz).
MS(ESI) [M+H]+: 516.

Reference Example 40

Synthesis of methyl 3-(2-cyanophenoxy)benzoate

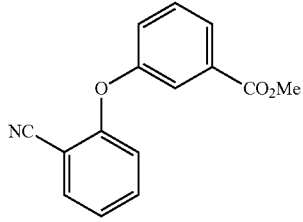 [SMILES: COC(=O)c1cccc(Oc2ccccc2C#N)c1]

A solution of methyl 3-hydroxybenzoate (0.6 g, 4.1 mmol), 2-fluorobenzonitrile (0.5 g, 4.1 mmol) and potassium carbonate (0.89 g, 6.4 mmol) in N-methyl-2-pyrrolidone was stirred while heating at 170° C. for eight hours. A saturated aqueous solution of ammonium chloride was added to the reaction mixture to stop the reaction, and the obtained solution was subsequently extracted with ethyl acetate and washed with saturated brine. The organic layer was dried over anhydrous sodium sulfate and then concentrated under vacuum, and the obtained crude product was purified by silica gel column chromatography (hexane:ethyl acetate=1:1, Rf=0.68) to obtain the title compound (0.58 g, 56%) (hereinafter referred to as the compound of Reference Example 40) as an oily substance.

MS(ESI) [M+H]$^+$: 254.

Reference Example 41

Synthesis of 3-(2-(((tert-butoxycarbonyl)amino)methyl)phenoxy)benzoic acid

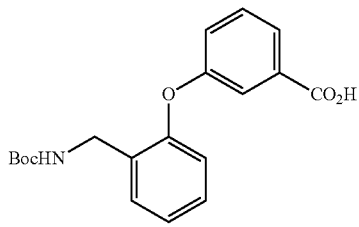 [SMILES: CC(C)(C)OC(=O)NCc1ccccc1Oc1cccc(C(=O)O)c1]

The title compound (0.28 g) (hereinafter referred to as the compound of Reference Example 41) was obtained as a pale yellow solid from the compound of Reference Example 40 (0.58 g) according to a method similar to that described in Reference Example 23.

MS(ESI) [M+H]$^+$: 343.

Reference Example 42

Synthesis of 4-(2-(aminomethyl)phenoxy)benzamide hydrochloride

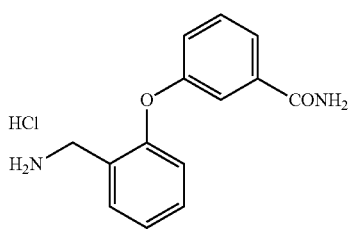 [SMILES: Cl ; NCc1ccccc1Oc1cccc(C(N)=O)c1]

The title compound (85 mg) (hereinafter referred to as the compound of Reference Example 42) was obtained as a white solid from the compound of Reference Example 41 (0.15 g) according to a method similar to that described in Reference Example 26 (chloroform:methanol=10:1, Rf=0.30).

MS(ESI) [M+H]$^+$: 243.

Example 44

Synthesis of 3-((2-((3-(3-(trifluoromethyl)phenyl)ureido)methyl)phenoxy)benzamide

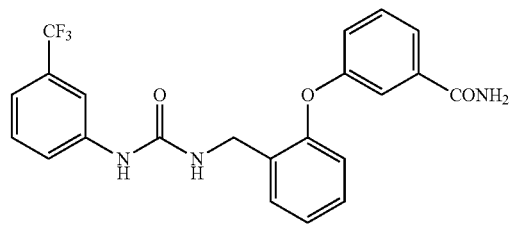 [SMILES: NC(=O)c1cccc(Oc2ccccc2CNC(=O)Nc2cccc(C(F)(F)F)c2)c1]

The title compound (16 mg) (hereinafter referred to as the compound of Example 44) was obtained as a white solid from phenyl (3-(trifluoromethyl)phenyl)carbamate (20 mg) and the compound of Reference Example 42 (22 mg) according to a method similar to that described in Example 10 (chloroform:methanol=10:1, Rf=0.52).

$^1$H-NMR (DMSO-d$_6$, 400 MHz) δ: 4.31 (2H, d, J=8.0 Hz), 6.73 (1H, t, J=8.0 Hz), 6.91 (1H, d, J=8.0 Hz), 7.13 (1H, dd, J=8.0, 2.0 Hz), 7.18-7.25 (2H, m), 7.30 (1H, td, J=8.0, 2.0 Hz), 7.41-7.51 (6H, m), 7.65 (1H, d, J=8.0 Hz), 7.96 (1H, s), 8.02 (1H, s), 9.03 (1H; s).

MS(ESI) [M+H]$^+$: 430.

Example 45

Synthesis of 3-(2-((3-(3-(oxetan-3-yloxy)-5-(trifluoromethyl)phenyl)ureido)methyl)phenoxy)benzamide

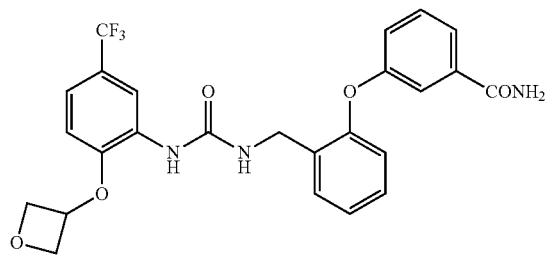 [SMILES: NC(=O)c1cccc(Oc2ccccc2CNC(=O)Nc2cc(C(F)(F)F)ccc2OC2COC2)c1]

The title compound (13 mg) (hereinafter referred to as the compound of Example 45) was obtained as a white solid from the compound of Reference Example 26 (20 mg) and the compound of Reference Example 42 (15 mg) according to a method similar to that described in Example 10 (chloroform:methanol=10:1, Rf=0.42).

$^1$H-NMR (DMSO-d$_6$, 400 MHz) δ: 4.35 (2H, d, J=8.0 Hz), 4.58-4.71 (2H, m), 4.96 (2H, t, J=8.0 Hz), 5.41 (1H, t, J=4.0 Hz), 6.76 (1H, d, J=8.0 Hz), 6.93 (1H, d, J=8.0 Hz), 7.12-7.24 (3H, m), 7.33 (1H, td, J=8.0, 2.0 Hz), 7.44-7.10 (5H, m), 7.63 (1H, d, J=8.0 Hz), 8.01 (1H, s), 8.29 (1H, s), 8.54 (1H, d, J=4.0 Hz).

MS(ESI) [M+H]$^+$: 502

Reference Example 43

Synthesis of 2,2,2-trichloroethyl (5-chloro-2-(trifluoromethyl)phenyl)carbamate

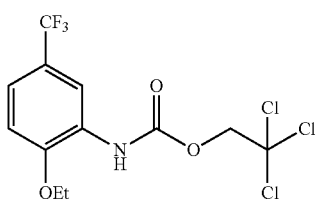 [SMILES: CCOc1ccc(C(F)(F)F)cc1NC(=O)OCC(Cl)(Cl)Cl]

An intermediate was obtained from 1-ethoxy-2-nitro-4-(trifluoromethyl)benzene (0.139 g) according to a method similar to that described in Reference Example 37. The title compound (0.14 g) (hereinafter referred to as the compound of Reference Example 43) was obtained as a white solid from the obtained crude product according to a method similar to that described in Reference Example 7 (hexane:ethyl acetate=1:1, Rf=0.63).

MS(ESI) [M+H]$^+$: 381.

Example 46

Synthesis of 4-((2-((3-(2-ethoxy-5-(trifluoromethyl)phenyl)ureido)methyl)phenoxy)benzamide

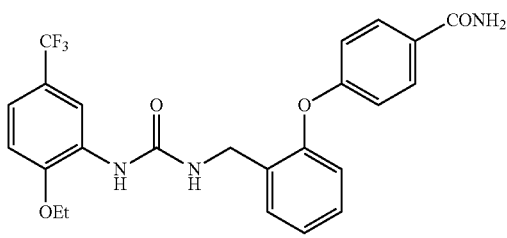 [SMILES: CCOc1ccc(C(F)(F)F)cc1NC(=O)NCc1ccccc1Oc1ccc(C(N)=O)cc1]

The title compound (28 mg) (hereinafter referred to as the compound of Example 46) was obtained as a white solid from the compound of Reference Example 25 (31 mg) and the compound of Reference Example 43 (40 mg) according to a method similar to that described in Example 10 (chloroform:methanol=10:1, Rf=0.36).

$^1$H-NMR (DMSO-d$_6$, 400 MHz) δ: 1.41 (3H, t, J=8.0 Hz), 4.18 (2H, q, J=8.0 Hz), 4.27 (2H, d, J=8.0 Hz), 6.94-7.00 (3H, m), 7.11 (1H, d, J=8.0 Hz), 7.20-7.39 (4H, m), 7.47 (1H, dd, J=8.0, 2.0 Hz), 7.56 (1H, t, J=8.0 Hz), 7.90 (3H, d, J=8.0 Hz), 8.16 (1H, s), 8.50 (1H, d, J=2.0 Hz).

MS(ESI) [M+H]$^+$: 474.

Reference Example 44

Synthesis of ethyl 6-(2-cyanophenoxy)nicotinate

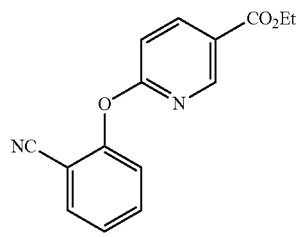 [SMILES: CCOC(=O)c1ccc(Oc2ccccc2C#N)nc1]

The title compound (200 mg) (hereinafter referred to as the compound of Reference Example 44) was obtained as an oily substance from ethyl 4-chloronicotinate (224 mg) according to a method similar to that described in Reference Example 21.

MS(ESI) [M+H]$^+$: 269.

Reference Example 45

Synthesis of ethyl 6-(2-(aminomethyl)phenoxy)nicotinate

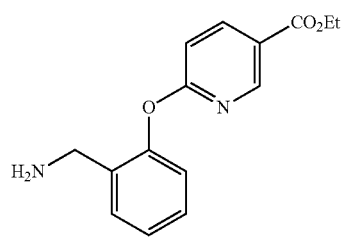 [SMILES: CCOC(=O)c1ccc(Oc2ccccc2CN)nc1]

The title compound (110 mg) (hereinafter referred to as the compound of Reference Example 45) was obtained as an oily substance from the compound of Reference Example 44 (0.8 g) according to a method similar to that described in Reference Example 22 (amino-silica gel, chloroform:methanol=10:1, Rf=0.12).

MS(ESI) [M+H]$^+$: 273.

Example 47

Synthesis of 6-(2-((3-(3-(trifluoromethyl)phenyl)ureido)methyl)phenoxy)nicotinamide

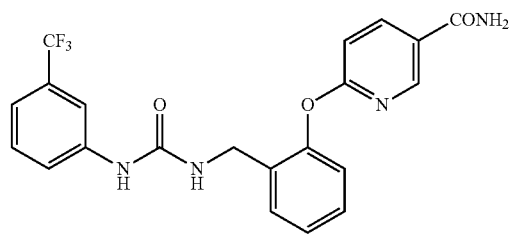 [SMILES: NC(=O)c1ccc(Oc2ccccc2CNC(=O)Nc2cccc(C(F)(F)F)c2)nc1]

To a solution of the compound of Reference Example 45 (80 mg, 0.29 mmol) and diisopropylethylamine (50 mg, 0.38 mmol) in N,N-dimethylformamide, 1-trifluoromethyl-3-isocyanatobenzene (55 mg, 0.29 mmol) was added, and the obtained solution was stirred at room temperature for three hours. A saturated aqueous solution of ammonium chloride was added to the reaction mixture to stop the reaction, and the obtained solution was subsequently extracted with ethyl acetate and washed with saturated brine. The organic layer was dried over anhydrous sodium sulfate and then concentrated under vacuum, and the obtained crude product was purified by silica gel column chromatography (chloroform:methanol=10:1, Rf=0.42) to obtain an ethyl ester as an intermediate (50 mg, 52%). The title compound (21 mg, 32%) (hereinafter referred to as the compound of Example 47) was obtained as a white solid from the obtained intermediate according to a method similar to those described in Examples 8 and 13 (chloroform:methanol=10:1, Rf=0.31).

$^1$H-NMR (DMSO-d$_6$, 400 MHz) δ: 4.20 (2H, d, J=8.0 Hz), 6.64 (1H, t, J=4.0 Hz), 7.08-7.14 (2H, m), 7.22 (1H, d, J=8.0 Hz), 7.27 (1H, td, J=8.0, 2.0 Hz), 7.34 (1H, td, J=8.0, 2.0 Hz), 7.42-7.48 (4H, m), 7.95 (1H, s), 8.03 (1H, br), 8.27 (1H, dd, J=8.0, 4.0 Hz), 8.61 (1H, d, J=2.0 Hz), 8.99 (1H, s).

MS(ESI) [M+H]$^+$: 431.

Example 48

Synthesis of N-methyl-6-(2-((3-(3-(trifluoromethyl)phenyl)ureido)methyl)phenoxy)nicotinamide

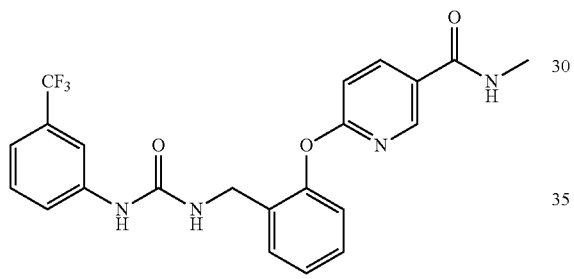

The title compound (16 mg) (hereinafter referred to as the compound of Example 48) was obtained as a white solid from the compound of Reference Example 45 (80 mg) according to a method similar to that described in Example 47 (chloroform:methanol=10:1, Rf=0.42).

$^1$H-NMR (DMSO-d$_6$, 400 MHz) δ: 2.78 (3H, d, J=8.0 Hz), 4.20 (2H, d, J=8.0 Hz), 6.62 (1H, t, J=4.0 Hz), 7.08-7.14 (2H, m), 7.22 (1H, d, J=8.0 Hz), 7.27 (1H, td, J=8.0, 2.0 Hz), 7.34 (1H, td, J=8.0, 2.0 Hz), 7.42-7.48 (4H, m), 7.94 (1H, s), 8.23 (1H, dd, J=8.0, 4.0 Hz), 8.49 (1H, d, J=8.0 Hz), 8.56 (1H, d, J=4.0 Hz), 8.98 (1H, s).

MS(ESI) [M+H]$^+$: 445.

Reference Example 46

Synthesis of 2,2,2-trichloroethyl (5-chloro-2-methoxyphenyl)carbamate

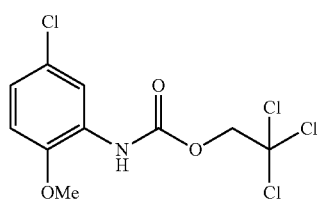

The title compound (203 mg) (hereinafter referred to as the compound of Reference Example 46) was obtained as a white solid from 5-chloro-2-methoxyaniline (120 mg) according to a method similar to that described in Reference Example 7 (hexane:ethyl acetate=1:1, Rf=0.58).

MS(ESI) [M+H]$^+$: 333.

Reference Example 47

Synthesis of 2,2,2-trichloroethyl (5-chloro-2-ethoxyphenyl)carbamate

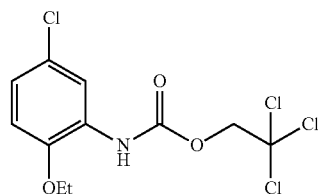 [SMILES: CCOc1ccc(Cl)cc1NC(=O)OCC(Cl)(Cl)Cl]

The title compound (0.15 g) (hereinafter referred to as the compound of Reference Example 47) was obtained as a white solid from 5-chloro-2-ethoxyaniline (160 mg) according to a method similar to that described in Reference Example 7 (hexane:ethyl acetate=1:1, Rf=0.61).

MS(ESI) [M+H]$^+$: 348.

Example 49

Synthesis of 4-(2-((3-(3-chlorophenyl)ureido)methyl)phenoxy)benzamide

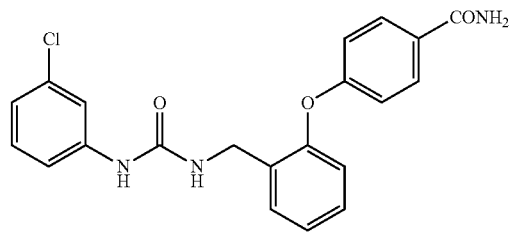 [SMILES: NC(=O)c1ccc(Oc2ccccc2CNC(=O)Nc2cccc(Cl)c2)cc1]

To a solution of the compound of Reference Example 25 (24 mg) and diisopropylethylamine (20 mg) in N,N-dimethylformamide, 1-chloro-3-isocyanatobenzene (0.012 ml) was added, and the obtained solution was stirred at room temperature for three hours. A saturated aqueous solution of ammonium chloride was added to the reaction mixture to stop the reaction, and the obtained solution was subsequently extracted with ethyl acetate and washed with saturated brine. The organic layer was dried over anhydrous sodium sulfate and then concentrated under vacuum, and the obtained crude product was purified by silica gel column chromatography (chloroform:methanol=10:1, Rf=0.30) to obtain the title compound (0.015 g, 39%) (hereinafter referred to as the compound of Example 49) as a white solid.

$^1$H-NMR (DMSO-d$_6$, 400 MHz) δ: 4.27 (2H, d, J=8.0 Hz), 6.67 (1H, d, J=8.0 Hz), 6.92-7.00 (4H, m), 7.17 (1H, d, J=8.0 Hz), 7.23 (2H, t, J=8.0 Hz), 7.31-7.34 (2H, m), 7.43 (1H, d, J=8.0 Hz), 7.66 (1H, t, J=4.0 Hz), 7.90 (3H, d, J=8.0 Hz), 8.86 (1H, s).

MS(ESI) [M+H]$^+$: 396.

Example 50

Synthesis of 4-((2-((3-(5-chloro-2-methoxyphenyl)ureido)methyl)phenoxy)benzamide

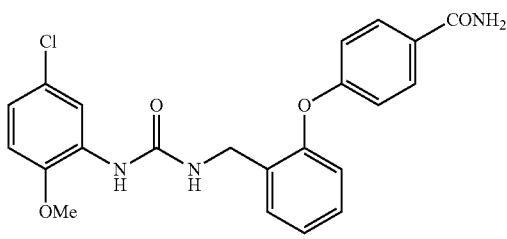 [SMILES: COc1ccc(Cl)cc1NC(=O)NCc1ccccc1Oc1ccc(C(N)=O)cc1]

The title compound (11 mg) (hereinafter referred to as the compound of Example 50) was obtained as a white solid from the compound of Reference Example 25 (17 mg) and the compound of Reference Example 46 (20 mg) according to a method similar to that described in Example 10 (chloroform:methanol=10:1, Rf=0.36).

$^1$H-NMR (DMSO-$d_6$, 400 MHz) δ: 3.83 (3H, s), 4.25 (2H, d, J=8.0 Hz), 6.90 (1H, dd, J=8.0, 4.0 Hz), 6.95-7.00 (4H, m), 7.22-7.45 (5H, m), 7.90 (3H, d, J=8.0 Hz), 8.17 (1H, d, J=2.0 Hz), 8.25 (1H, s).

MS(ESI) [M+H]$^+$: 426.

Example 51

Synthesis of 4-((2-((3-(5-chloro-2-ethoxyphenyl)ureido)methyl)phenoxy)benzamide

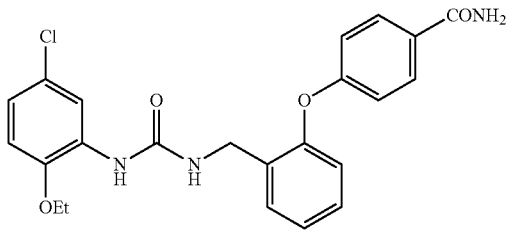 [SMILES: CCOc1ccc(Cl)cc1NC(=O)NCc1ccccc1Oc1ccc(C(N)=O)cc1]

The title compound (31 mg) (hereinafter referred to as the compound of Example 51) was obtained as a white solid from the compound of Reference Example 25 (33 mg) and the compound of Reference Example 47 (40 mg) according to a method similar to that described in Example 10 (chloroform:methanol=10:1, Rf=0.40).

$^1$H-NMR (DMSO-$d_6$, 400 MHz) δ: 1.37 (3H, t, J=8.0 Hz), 4.08 (2H, q, J=8.0 Hz), 4.27 (2H, d, J=8.0 Hz), 6.87 (1H, dd, J=8.0, 4.0 Hz), 6.94-7.00 (4H, m), 7.23-7.36 (3H, m), 7.46 (1H, dd, J=8.0, 2.0 Hz), 7.52 (1H, t, J=8.0 Hz), 7.90 (3H, d, J=8.0 Hz), 8.05 (1H, s), 8.18 (1H, d, J=2.0 Hz).

MS(ESI) [M+H]$^+$: 440.

Example 52

Evaluation of DDR1 Inhibition Activity

The DDR1 inhibition activity of the compounds of Examples 1 to 51 was evaluated with HTRF® KinEASE-TK kit (Cisbio Bioassays).

Each test substance was dissolved in dimethyl sulfoxide (hereinafter referred to as DMSO) and then used for the evaluation as described below. Moreover, each of test substances and reagents was diluted in the kinase buffer (Cisbio Bioassays) prepared by adding thereto MgCl$_2$, MnCl$_2$, DTT, and the Supplemental Enzyme buffer (Cisbio Bioassays) to concentrations of 5 mmol/L, 0.5 mmol/L, 0.25 mmol/L, and 50 nmol/L, respectively, and then used. Each test substance (in DMSO in a final concentration of 1%), the intracellular domain of DDR1 (in a final concentration of 5 ng/μL) (Carna Biosciences, Inc.), the phosphate donor ATP (in final concentration of 25 mol/L) (Sigma), and the substrate TK Substrate-biotin (in a final concentration of 1000 nmol/L) (Cisbio Bioassays) were added to a 384-well black plate (Corning) and allowed to react at room temperature for one hour. After completion of the reaction, the TK Antibody-Cryptate (Cisbio Bioassays) and the Streptavidin-XL665 (Cisbio Bioassays) were added thereto and allowed to react at room temperature for one hour. In addition, the plate was provided with a well to which a test substance was not added, and with a well to which the intracellular domain of DDR1 and a test substance were not added.

The fluorescence intensity in each well was measured using a multi-label counter (Envision, PerkinElmer; excitation wavelength: 320 nm, measurement wavelength: 665 nm and 620 nm) to calculate a Ratio (the fluorescence intensity at 665 nm/the fluorescence intensity at 620 nm). The inhibition rate (%) of a test substance at each concentration was calculated based on the formula below.

Inhibition rate (%)=([the Ratio obtained from the well containing no test substance]−[the Ratio from a well containing a test substance])/([the Ratio obtained from the well containing no test substance]−[the Ratio obtained from the well containing no intracellular domain of DDR1 and no test substance])×100

The calculated inhibition rates were fitted to a sigmoidal dose-response curve by regression analysis using the Prism 5.04 (GraphPad Software, Inc.) to calculate the IC$_{50}$ value of the test substance.

The IC$_{50}$ value of each test substance is shown in Table 2. As seen from the results in Table 2, the urea derivatives (I) or the pharmaceutically acceptable salts thereof were indicated to have high DDR1 inhibition activity.

TABLE 2

| Test Substance | IC$_{50}$ (nmol/L) |
|---|---|
| Compound of Example 1 | 52.1 |
| Compound of Example 2 | 26.1 |
| Compound of Example 3 | 838 |
| Compound of Example 4 | 51.7 |
| Compound of Example 5 | 47 |
| Compound of Example 6 | 32.5 |
| Compound of Example 7 | 585 |
| Compound of Example 8 | 172 |
| Compound of Example 9 | 137 |
| Compound of Example 10 | 156 |
| Compound of Example 11 | 150 |
| Compound of Example 12 | 38.6 |
| Compound of Example 13 | 96.4 |
| Compound of Example 14 | 156 |
| Compound of Example 15 | 308 |
| Compound of Example 16 | 163 |
| Compound of Example 17 | 185 |
| Compound of Example 18 | 23.3 |
| Compound of Example 19 | 37.4 |
| Compound of Example 20 | 13.5 |
| Compound of Example 21 | 67.4 |
| Compound of Example 22 | 28.5 |
| Compound of Example 23 | 78.7 |
| Compound of Example 24 | 42.2 |
| Compound of Example 25 | 194 |

TABLE 2-continued

| Test Substance | IC$_{50}$ (nmol/L) |
| --- | --- |
| Compound of Example 26 | 38.3 |
| Compound of Example 27 | 21 |
| Compound of Example 28 | 14.5 |
| Compound of Example 29 | 5.98 |
| Compound of Example 30 | 12.4 |
| Compound of Example 31 | 11 |
| Compound of Example 32 | 17.3 |
| Compound of Example 33 | 12.9 |
| Compound of Example 34 | 22 |
| Compound of Example 35 | 12.9 |
| Compound of Example 36 | 13.2 |
| Compound of Example 37 | 11.7 |
| Compound of Example 38 | 4.64 |
| Compound of Example 39 | 4.2 |
| Compound of Example 40 | 8.91 |
| Compound of Example 41 | 35.2 |
| Compound of Example 42 | 21.5 |
| Compound of Example 43 | 78.5 |
| Compound of Example 44 | 23.7 |
| Compound of Example 45 | 12.2 |
| Compound of Example 46 | 22.5 |
| Compound of Example 47 | 23.4 |
| Compound of Example 48 | 29.1 |
| Compound of Example 49 | 19.3 |
| Compound of Example 50 | 12.3 |
| Compound of Example 51 | 18.3 |

INDUSTRIAL APPLICABILITY

Urea derivatives (I) and pharmaceutically acceptable salts thereof have high DDR1 inhibition activity and therefore can be used as DDR1 inhibitors.

The invention claimed is:

1. A urea derivative represented by Formula (I):

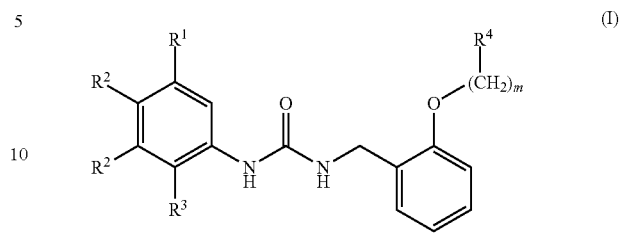

wherein
m is 0 or 1;
$R^1$ is a halogen atom, trifluoromethyl, trifluoromethoxy, or pentafluorosulfanyl;
$R^2$ is a hydrogen atom or methyl in which one hydrogen atom is replaced with hydroxyl, piperazinyl, or 4-methylpiperazinyl;
$R^3$ is a hydrogen atom or $R^5O$—;
$R^4$ is phenyl which is optionally substituted;
$R^5$ is $C_1$-$C_3$ alkyl, 3-oxetanyl, or 4-piperidyl,
or a pharmaceutically acceptable salt thereof.

2. The urea derivative according to claim 1, or a pharmaceutically acceptable salt thereof, wherein $R^4$ is 3- or 4-carbamoylphenyl, or 4-N-methylcarbamoylphenyl.

3. The urea derivative according to claim 1, or a pharmaceutically acceptable salt thereof, wherein m is 0.

4. A method of inhibiting Discoidin Domain Receptor 1, comprising, administering an effective amount of the urea derivative according to claim 1, or a pharmaceutically acceptable salt thereof.

5. The urea derivative according to claim 2, or a pharmaceutically acceptable salt thereof, wherein m is 0.

6. The method of inhibiting Discoidin Domain Receptor 1 according to claim 4, wherein $R^4$ is 3- or 4-carbamoylphenyl, or 4-N-methylcarbamoylphenyl.

7. The method of inhibiting Discoidin Domain Receptor 1, according to claim 4, wherein m is 0.

8. The method of inhibiting Discoidin Domain Receptor 1, according to claim 6, wherein m is 0.

* * * * *